United States Patent
Goetz et al.

(10) Patent No.: US 10,457,871 B2
(45) Date of Patent: *Oct. 29, 2019

(54) COMPOUNDS AND LIQUID-CRYSTALLINE MEDIUM

(71) Applicant: MERCK PATENT GMBH, Darmstadt (DE)

(72) Inventors: Achim Goetz, Alsbach-Haehnlein (DE); Rocco Fortte, Frankfurt am Main (DE); Martin Engel, Darmstadt (DE); Sabrina Maag, Pfungstadt (DE); Ingo Almeroth, Bensheim (DE); Thomas Mergner, Breuberg (DE); Thorsten Kodek, Moerfelden-Walldorf (DE); Detlef Pauluth, Ober-Ramstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 287 days.

This patent is subject to a terminal disclaimer.

(21) Appl. No.: 14/840,461

(22) Filed: Aug. 31, 2015

(65) Prior Publication Data

US 2016/0060528 A1 Mar. 3, 2016

(30) Foreign Application Priority Data

Sep. 2, 2014 (EP) .................................. 14003014

(51) Int. Cl.
| | | |
|---|---|---|
| C09K 19/54 | (2006.01) | |
| C09K 19/34 | (2006.01) | |
| C09K 19/30 | (2006.01) | |
| C07D 401/12 | (2006.01) | |
| C09K 19/44 | (2006.01) | |
| C09K 19/04 | (2006.01) | |
| C09K 19/12 | (2006.01) | |

(52) U.S. Cl.
CPC ............ *C09K 19/54* (2013.01); *C07D 401/12* (2013.01); *C09K 19/3003* (2013.01); *C09K 19/3098* (2013.01); *C09K 19/3402* (2013.01); *C09K 19/3483* (2013.01); *C09K 19/44* (2013.01); *C09K 2019/0466* (2013.01); *C09K 2019/122* (2013.01); *C09K 2019/123* (2013.01); *C09K 2019/301* (2013.01); *C09K 2019/3004* (2013.01); *C09K 2019/3009* (2013.01); *C09K 2019/3016* (2013.01); *C09K 2019/3422* (2013.01)

(58) Field of Classification Search
None
See application file for complete search history.

(56) References Cited

U.S. PATENT DOCUMENTS

| | | | |
|---|---|---|---|
| 4,279,804 A | 7/1981 | Cantatore et al. | |
| 5,536,277 A | 7/1996 | Shimode et al. | |
| 5,556,980 A * | 9/1996 | Sagawa | C07D 211/58 546/190 |
| 6,114,420 A | 9/2000 | Zedda et al. | |
| 6,958,176 B2 | 10/2005 | Li et al. | |
| 9,388,339 B2 | 7/2016 | Goebel et al. | |
| 9,434,882 B2 | 9/2016 | Goebel et al. | |
| 9,714,381 B2 * | 7/2017 | Archetti | C09K 19/32 |
| 9,873,834 B2 | 1/2018 | Goebel et al. | |
| 2004/0085490 A1 | 5/2004 | Li et al. | |
| 2006/0011886 A1 | 1/2006 | Li et al. | |
| 2011/0101270 A1 | 5/2011 | Manabe et al. | |
| 2012/0003401 A1 * | 1/2012 | Xu | C09K 19/3483 428/1.1 |
| 2013/0207038 A1 * | 8/2013 | Haensel | C09K 19/062 252/299.61 |
| 2013/0248763 A1 | 9/2013 | Goebel et al. | |
| 2013/0258268 A1 | 10/2013 | Goebel et al. | |
| 2014/0111730 A1 | 4/2014 | Goebel et al. | |
| 2016/0046863 A1 * | 2/2016 | Archetti | C09K 19/542 252/299.62 |
| 2016/0053178 A1 * | 2/2016 | Hirschmann | C09K 19/12 252/299.5 |

(Continued)

FOREIGN PATENT DOCUMENTS

| | | |
|---|---|---|
| CN | 102015963 B | 12/2014 |
| DE | 10 2011 013007 A1 | 10/2011 |
| DE | 10 2011 117937 A1 | 6/2012 |

(Continued)

OTHER PUBLICATIONS

European Search Report Corresponding to EP 15 00 2311—Dated: Jan. 28, 2016.
English Abstract of DE 10 2011 119144 A1—Publication Date: Jun. 14, 2012.
English Abstract of DE 10 2011 013007 A1—Publication Date: Oct. 6, 2011.

(Continued)

*Primary Examiner* — Cynthia H Kelly
*Assistant Examiner* — Anna Malloy
(74) *Attorney, Agent, or Firm* — Millen White Zelano & Branigan, PC

(57) ABSTRACT

Compounds of formula I,

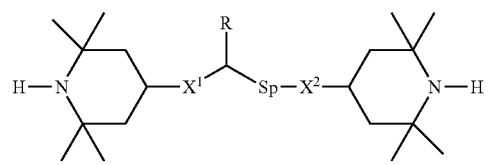

in which $X^1$, $X^2$, Sp, and R are as defined herein, are suitable for use in liquid-crystal media, such as liquid-crystal media used in liquid-crystal displays.

33 Claims, No Drawings

(56) References Cited

U.S. PATENT DOCUMENTS

2016/0208170 A1* 7/2016 Hirschmann ...... C09K 19/3491
2018/0375033 A1 12/2018 Yakushiji et al.

FOREIGN PATENT DOCUMENTS

| DE | 10 2011 119144 A1 | 6/2012 | |
|---|---|---|---|
| DE | 102011117937 A1 | 6/2012 | |
| DE | 102011119144 A1 | 6/2012 | |
| EP | 1184442 A1 | 3/2002 | |
| EP | 2 722 381 A2 | 4/2014 | |
| JP | 55022677 A | 2/1980 | |
| JP | 7070065 A2 | 3/1995 | |
| JP | 10330378 A | 12/1998 | |
| JP | 2015163349 A | 9/2015 | |
| JP | 2016041804 A | 3/2016 | |
| WO | WO 9407489 A1 * | 4/1994 | ........... A61K 31/445 |
| WO | 2009129911 A1 | 10/2009 | |
| WO | 2012/076104 A1 | 6/2012 | |
| WO | 2012076104 A1 | 6/2012 | |

OTHER PUBLICATIONS

Notification of the First Office action in corresponding CN 20150550018.3 dated Feb. 3, 2019 (pp. 1-6).
Notification of Reasons for Refusal (1st Office Action) in corresponding JP Appln. No. 2015-171792 dispatched May 23, 2019 (pp. 1-6).

* cited by examiner

COMPOUNDS AND LIQUID-CRYSTALLINE MEDIUM

The present invention relates to compounds of the formula I, in particular for use in liquid-crystal media, but also to the use of these liquid-crystal media in liquid-crystal displays, and to these liquid-crystal displays.

The liquid-crystal media according to the invention are distinguished by a particularly short response time in the displays according to the invention at the same time as a high voltage holding ratio (VHR or also just HR for short).

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a "twisted nematic" structure, STN ("super-twisted nematic") cells, SBE ("superbirefringence effect") cells and OMI ("optical mode interference") cells. The commonest display devices are based on the Schadt-Helfrich effect and have a twisted nematic structure. In addition, there are also cells which work with an electric field parallel to the substrate and liquid-crystal plane, such as, for example, IPS ("in-plane switching") cells. TN, STN, FFS (fringe field switching) and IPS cells, in particular, are currently commercially interesting areas of application for the media according to the invention.

In addition, liquid-crystal displays which use the ECB (electrically controlled birefringence) effect with dielectrically negative liquid crystals in a homeotropic starting alignment are known.

The principle of electrically controlled birefringence, the ECB effect or DAP (deformation of aligned phases) effect, was described for the first time in 1971 (M. F. Schieckel and K. Fahrenschon, "Deformation of nematic liquid crystals with vertical orientation in electrical fields", Appl. Phys. Lett. 19 (1971), 3912). Papers by J. F. Kahn (Appl. Phys. Lett. 20 (1972), 1193) and G. Labrunie and J. Robert (J. Appl. Phys. 44 (1973), 4869) followed.

The papers by J. Robert and F. Clerc (SID 80 Digest Techn. Papers (1980), 30), J. Duchene (Displays 7 (1986), 3) and H. Schad (SID 82 Digest Techn. Papers (1982), 244) have shown that liquid-crystalline phases must have high values for the ratio between the elastic constants $K_3/K_1$, high values for the optical anisotropy $\Delta n$ and values for the dielectric anisotropy $\Delta \varepsilon$ of $\leq -0.5$ in order to be suitable for use for high-information display elements based on the ECB effect. Electro-optical display elements based on the ECB effect have a homeotropic edge alignment (VA technology=vertically aligned). Dielectrically negative liquid-crystal media can also be used in displays which use the so-called IPS (in-plane switching) effect.

Industrial application of the above-mentioned effects in electro-optical display elements requires LC phases which have to meet a multiplicity of requirements. Particularly important here are chemical resistance to moisture, air and physical influences, such as heat, radiation in the infrared, visible and ultraviolet regions, and direct and alternating electric fields.

Furthermore, LC phases which can be used industrially are required to have a liquid-crystalline mesophase in a suitable temperature range and low viscosity.

None of the series of compounds having a liquid-crystalline mesophase that have been disclosed hitherto includes a single compound which meets all these requirements. Mixtures of two to 25, preferably three to 18, compounds are therefore generally prepared in order to obtain substances which can be used as LC phases.

Matrix liquid-crystal displays (MLC displays) are known. Non-linear elements which can be used for individual switching of the individual pixels are, for example, active elements (i.e. transistors). The term "active matrix" is then used, where in general use is made of thin-film transistors (TFTs), which are generally arranged on a glass plate as substrate.

A distinction is made between two technologies: TFTs comprising compound semiconductors, such as, for example, CdSe, or TFTs based on polycrystalline and, inter alia, amorphous silicon. The latter technology currently has the greatest commercial importance worldwide.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully color-capable displays, in which a mosaic of red, green and blue filters is arranged in such a way that a filter element is located opposite each switchable pixel.

The TFT displays most used hitherto usually operate with crossed polarizers in transmission and are backlit. For TV applications, IPS cells or ECB (or VAN) cells are used, whereas monitors usually use IPS cells or TN (twisted nematic) cells, and notebooks, laptops and mobile applications usually use TN cells.

The term MLC displays here encompasses any matrix display having integrated non-linear elements, i.e., besides the active matrix, also displays having passive elements, such as varistors or diodes (MIM=metal-insulator-metal).

MLC displays of this type are particularly suitable for TV applications, monitors and notebooks or for displays with a high information density, for example in automobile manufacture or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, pp. 141 ff., Paris; STROMER, M., Proc. Eurodisplay 84, September 1984: Design of Thin Film Transistors for Matrix Addressing of Television Liquid Crystal Displays, pp. 145 ff., Paris]. With decreasing resistance, the contrast of an MLC display deteriorates. Since the specific resistance of the liquid-crystal mixture generally drops over the life of an MLC display owing to interaction with the inside surfaces of the display, a high (initial) resistance is very important for displays that have to have acceptable resistance values over a long operating period.

Displays which use the ECB effect have become established as so-called VAN (vertically aligned nematic) displays, besides IPS displays (for example: Yeo, S. D., Paper 15.3: "An LC Display for the TV Application", SID 2004 International Symposium, Digest of Technical Papers, XXXV, Book II, pp. 758 and 759) and the long-known TN displays, as one of the three more recent types of liquid-crystal display that are currently the most important, in particular for television applications.

The following may be mentioned as the most important designs: MVA (multi-domain vertical alignment, for example: Yoshide, H. et al., Paper 3.1: "MVA LCD for Notebook or Mobile PCs . . . ", SID 2004 International Symposium, Digest of Technical Papers, XXXV, Book I, pp. 6 to 9, and Liu, C. T. et al., Paper 15.1: "A 46-inch TFT-LCD HDTV Technology . . . ", SID 2004 International Symposium, Digest of Technical Papers, XXXV, Book II, pp. 750 to 753), PVA (patterned vertical alignment, for example: Kim, Sang Soo, Paper 15.4: "Super PVA Sets New State-of-the-Art for LCD-TV", SID 2004 International Symposium, Digest of Technical Papers, XXXV, Book II, pp. 760 to 763) and ASV (advanced super view, for example: Shigeta, Mitzuhiro and Fukuoka, Hirofumi, Paper 15.2: "Development of High Quality LCDTV", SID 2004 International Symposium, Digest of Technical Papers, XXXV, Book II, pp. 754 to 757).

In general form, the technologies are compared, for example, in Souk, Jun, SID Seminar 2004, Seminar M-6: "Recent Advances in LCD Technology", Seminar Lecture Notes, M-6/1 to M-6/26, and Miller, Ian, SID Seminar 2004, Seminar M-7: "LCD-Television", Seminar Lecture Notes, M-7/1 to M-7/32. Although the response times of modern ECB displays have already been significantly improved by addressing methods with overdrive, for example: Kim, Hyeon Kyeong et al., Paper 9.1: "A 57-in. Wide UXGA TFT-LCD for HDTV Application", SID 2004 International Symposium, Digest of Technical Papers, XXXV, Book I, pp. 106 to 109, the achievement of video-compatible response times, in particular in the switching of grey shades, is still a problem which has not yet been solved to a satisfactory extent.

ECB displays, like ASV displays, use liquid-crystalline media having negative dielectric anisotropy ($\Delta\varepsilon$), whereas TN and to date all conventional IPS displays use liquid-crystalline media having positive dielectric anisotropy.

In all the said liquid-crystal displays, the liquid crystals are used as dielectrics, whose optical properties change reversibly on application of an electrical voltage.

Since in displays in general, i.e. also in displays in accordance with these mentioned effects, the operating voltage should be as low as possible, use is made of liquid-crystal media which are generally predominantly composed of liquid-crystal compounds, all of which have the same sign of the dielectric anisotropy and have the highest possible value of the dielectric anisotropy. In general, at most relatively small proportions of neutral compounds and if possible no compounds having a sign of the dielectric anisotropy which is opposite to that of the medium are employed.

For many practical applications in liquid-crystal displays, the known liquid-crystal media are not sufficiently stable. In particular, their stability to irradiation with UV, but also even with conventional backlighting, results in an impairment, in particular, of the electrical properties. Thus, for example, the conductivity increases significantly.

The use of so-called "hindered amine light stabilizers", HALS for short, has already been proposed for the stabilization of liquid-crystal mixtures.

DE 102011117937.6 describes liquid-crystal mixtures having positive dielectric anisotropy which comprise TINUVIN 770® for stabilization.

DE 102011119144.9 and PCT/EP2011/005692 describe liquid-crystal mixtures having negative dielectric anisotropy which comprise, inter alia, HALS N-oxides for stabilization.

Nematic liquid-crystal mixtures having negative dielectric anisotropy which comprise a small amount of TINUVIN®770, a compound of the formula

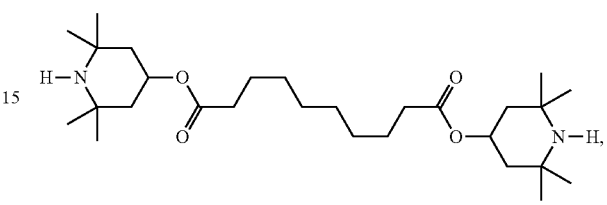

as stabilizer are proposed, for example, in WO 2009/129911 A1. However, the corresponding liquid-crystal mixtures in some cases do not have adequate properties for some practical applications. Inter alia, they are sometimes not sufficiently stable to irradiation with typical CCFL (cold cathode fluorescent lamp) backlighting and/or exhibit problems with the LTS (low-temperature stability).

The use of various stabilizers in liquid-crystalline media is described, for example, in JP (S)55-023169 (A), JP (H)05-117324 (A), WO 02/18515 A1 and JP (H) 09-291282 (A).

TINUVIN® 123, a compound of the formula

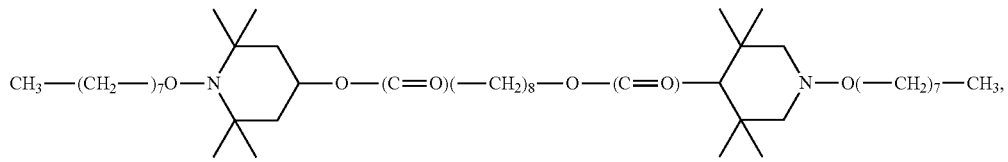

has also been proposed for stabilization purposes.

Mesogenic compounds containing one or two HALS units are disclosed in EP 1 784 442 A1.

HALS with various substituents on the nitrogen atom are compared with respect to their $pK_B$ values in Ohkatsu, Y., *J. of Japan Petroleum Institute*, 51, 2008, pages 191-204. The following types of structural formulae are disclosed here.

| Type | Active group of the stabilizer |
|---|---|
| "HALS" | RO—⟨⟩—N—H |
| "R-HALS" or "NR-HALS" | RO—⟨⟩—N—R |

| Type | Active group of the stabilizer |
|---|---|
| "NOR-HALS" | 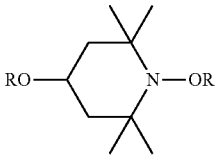 |

The compound TEMPOL, of the following formula:

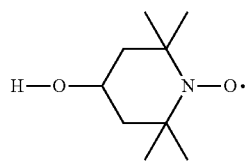

TEMPOL is known; it is mentioned, for example, in Miéville, P. et al., Angew. Chem. 2010, 122, pages 6318-6321. It is commercially available from various manufacturers and is employed, for example, as polymerization inhibitor and, in particular in combination with UV absorbers, as light or UV protection in formulations for precursors of polyolefins, polystyrenes, polyamides, coatings and PVC.

The liquid-crystal media of the prior art having correspondingly low addressing voltages have relatively low electrical resistance values or a low VHR and often result in undesired flicker and/or inadequate transmission in the displays. In addition, they are not sufficiently stable to heating and/or UV exposure, at least if they have correspondingly high polarity, as is necessary for low addressing voltages.

On the other hand, the addressing voltage of the displays of the prior art which have a high VHR is often too high, in particular for displays which are not connected directly or not continuously to the power supply network, such as, for example, displays for mobile applications.

In addition, the phase range of the liquid-crystal mixture must be sufficiently broad for the intended application of the display.

The response times of the liquid-crystal media in the displays must be improved, i.e. reduced. This is particularly important for displays for television or multimedia applications. In order to improve the response times, it has repeatedly been proposed in the past to optimize the rotational viscosity of the liquid-crystal media ($\gamma_1$), i.e. to achieve media having the lowest possible rotational viscosity. However, the results achieved here are inadequate for many applications and therefore make it appear desirable to find further optimization approaches.

Adequate stability of the media to extreme loads, in particular to UV exposure and heating, is very particularly important. In particular in the case of applications in displays in mobile equipment, such as, for example, mobile telephones, this may be crucial.

The disadvantage of the MLC displays disclosed hitherto is due to their comparatively low contrast, the relatively high viewing-angle dependence and the difficulty in producing grey shades in these displays, as well as their inadequate VHR and their inadequate lifetime.

There thus continues to be a great demand for MLC displays having very high specific resistance at the same time as a large working-temperature range, short response times and a low threshold voltage, with the aid of which various grey shades can be produced and which have, in particular, a good and stable VHR.

The invention is based on the object of providing MLC displays, not only for monitor and TV applications, but also for mobile telephones and navigation systems, which do not have the disadvantages indicated above, or only do so to a lesser extent, and at the same time have very high specific resistance values. In particular, it must be ensured for mobile telephones and navigation systems that they also work at extremely high and extremely low temperatures.

Upon further study of the specification and appended claims, other objects, aspects and advantages of the invention will become apparent.

Surprisingly, it has now been found that it is possible to achieve liquid-crystalline media having a suitable $\Delta\epsilon$, a suitable phase range and $\Delta n$ which do not have the disadvantages of the prior-art materials, or at least only do so to a considerably reduced extent.

Surprisingly, it has been found here that the compounds of the formula I, even when used alone without additional heat stabilizers, result in considerable, in many cases adequate, stabilization of liquid-crystal mixtures both to UV exposure and also to heating.

The invention thus relates to compounds of the formula I,

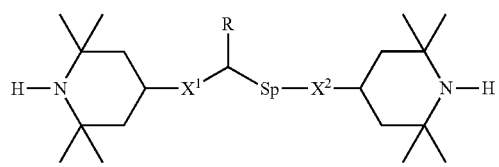

in which
$X^1$ and $X^2$ each, independently of one another, denote —O—, —(CO)—O—, —O—(CO)—, —O—(CO)—O—, —NH—, —NY$^{01}$— or —NH—(CO)—, preferably —O—, —(CO)—O— or —O—(CO)—,
$Y^{01}$ denotes alkyl having 1 to 12 C atoms,
Sp denotes straight-chain alkyl having 1 to 20 C atoms, preferably having 1 to 15 C atoms and particularly preferably having 1 to 10 C atoms, also cycloalkyl, cycloalkylalkyl or alkylcycloalkyl, where one or more —CH$_2$— groups in all these groups may each be replaced by —O— such a way that no two O atoms in the molecule are connected directly to one another, and
R denotes straight-chain or branched alkyl having 1 to 10 C atoms, also cycloalkyl, cycloalkylalkyl or alkylcycloalkyl, where one or more —CH$_2$— groups in all these groups may each be replaced by —O— in such a way that no two O atoms in the molecule are connected directly to one another, and preferably denotes straight-chain or branched alkyl having 1 to 7 C atoms and particularly preferably alkyl having 1 to 4 C atoms.

Preferred compounds of the formula I are shown below:

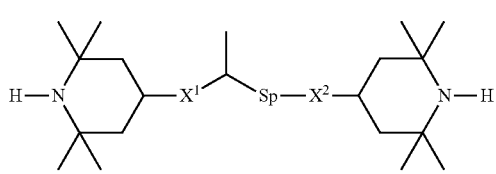

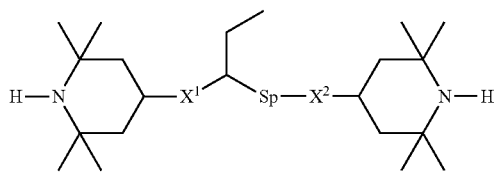

IB

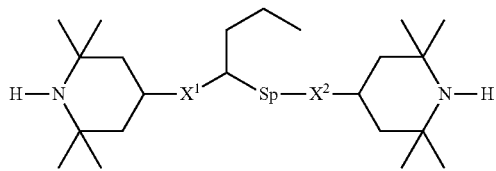

IC

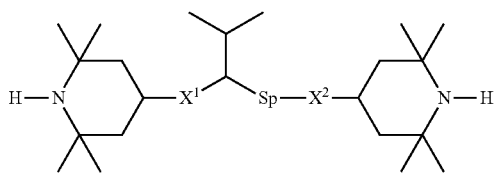

ID

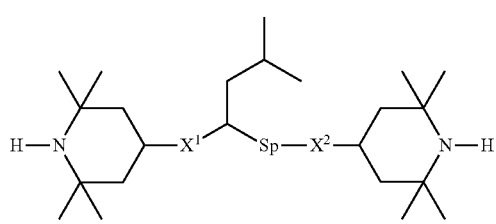

IE in which $X^1$, $X^2$ and Sp have one of the meanings indicated under formula I.

Further preferred compounds of the formula I are selected from the following compounds:

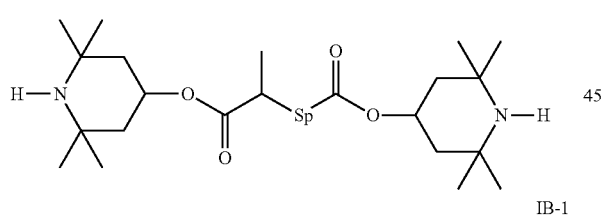

IA-1

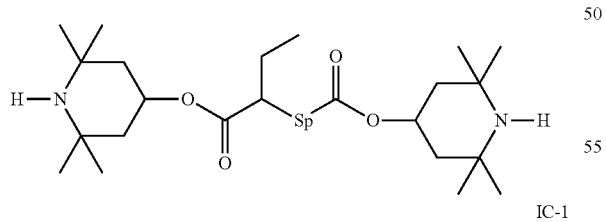

IB-1

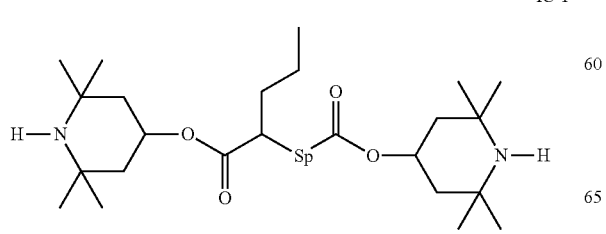

IC-1

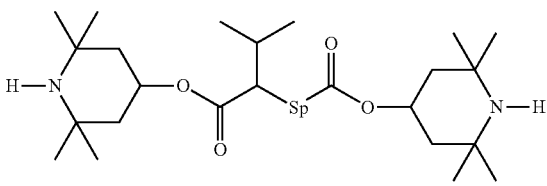

ID-1

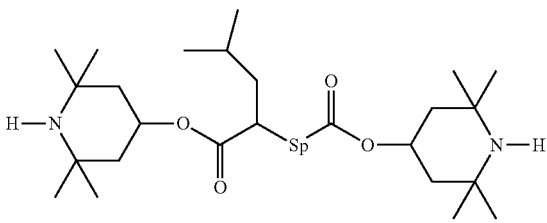

IE-1

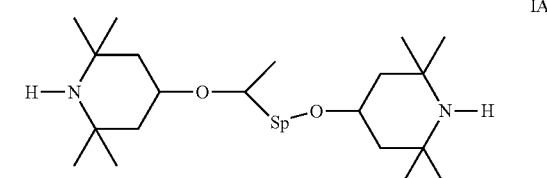

IA-2

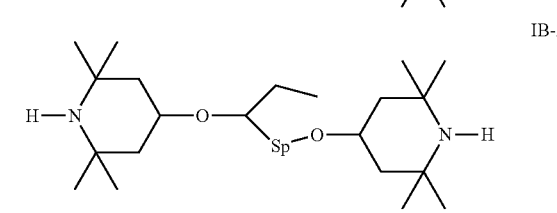

IB-2

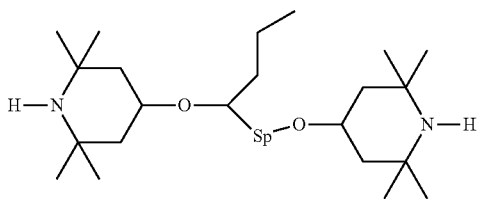

IC-2

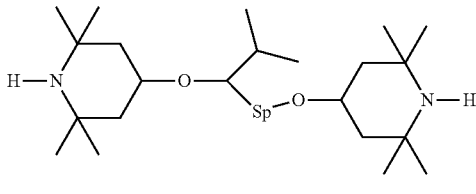

ID-2

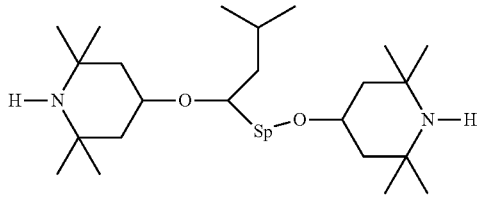

IE-2 in which Sp has one of the meanings indicated under formula I. If Sp in the above formulae denotes an alkyl radical, this may be straight-chain or branched. It is preferably straight-chain and has 1, 2, 3, 4, 5, 6, 7, 8, 9 or 10 C atom(s) and accordingly preferably denotes methyl, ethyl, propyl, butyl, pentyl, hexyl, heptyl, octyl, nonyl or decyl.

In particular, compounds of the formula I are preferably selected from the following compounds:

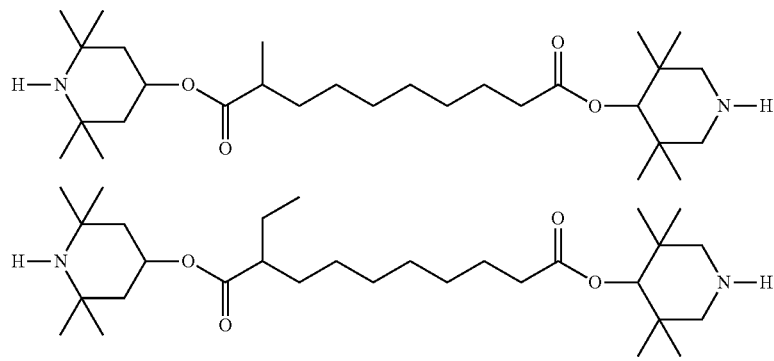

In the pure state, the compounds of the formula I are colorless and are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The present invention also relates to a liquid-crystalline medium having a nematic phase which comprises one or more compounds of the formula I, preferably in a concentration in the range from 1 ppm to 5,000 ppm, preferably in the range from 1 ppm to 2,000 ppm, particularly preferably in the range from 1 ppm to 1,000 ppm, in particular 1 ppm to 500 ppm.

The compounds of the formula I result in LC mixtures having the desired properties indicated above, in particular in LC mixtures having particularly short response times at the same time as a high voltage holding ratio (VHR or also merely HR for short). Furthermore, the compounds of the formula I have very good solubility in liquid-crystalline media.

The present invention also relates to electro-optical displays or electro-optical components which comprise liquid-crystalline media according to the invention.

Accordingly, the present invention likewise relates to the use of a liquid-crystalline medium according to the invention in an electro-optical display or in an electro-optical component, likewise to a process for the preparation of the liquid-crystalline media according to the invention, characterized in that one or more compounds of the formula I are mixed with one or more of the following compounds.

In addition, the present invention relates to a process for the stabilization of a liquid-crystalline medium having a nematic phase which comprises one or more of the following compounds, characterized in that one or more compounds of the formula I are added to the medium.

The term "have a nematic phase" here means on the one hand that no smectic phase and no crystallization are observed at low temperatures and on the other hand that no clearing occurs on heating from the nematic phase. The investigation at low temperatures is carried out in a flow viscometer at the corresponding temperature and checked by storage in test cells having a layer thickness corresponding to electro-optical use for at least 100 hours. If the storage stability at a temperature of −20° C. in a corresponding test cell is 1,000 h or more, the medium is regarded as stable at this temperature. At temperatures of −30° C. and −40° C., the corresponding times are 500 h and 250 h respectively. At high temperatures, the clearing point is measured by conventional methods in capillaries.

Preferred compounds which can be employed in a liquid-crystalline medium according to the invention are indicated below:

the medium comprises one or more neutral compounds of the formulae II and/or III,

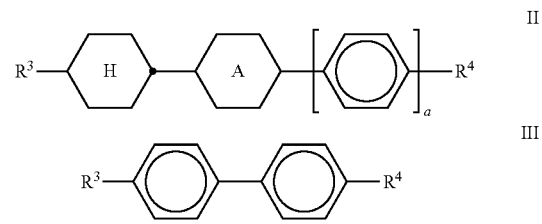

in which
A denotes 1,4-phenylene or trans-1,4-cyclohexylene,
a is 0 or 1,
$R^3$ denotes alkenyl having 2 to 9 C atoms, and
$R^4$ denotes an alkyl or alkoxy radical having 1 to 15 C atoms, where, in addition, one or more $CH_2$ groups in these radicals may each be replaced, independently of one another, by —C≡C—, —$CF_2$O—, —CH=CH—,

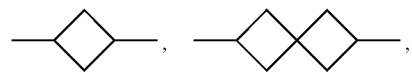

—O—, —CO—O—, or —O—CO— in such a way that O atoms are not linked directly to one another, and in which, in addition, one or more H atoms may each be replaced by halogen, preferably alkyl having 1 to 12 C atoms or alkenyl having 2 to 9 C atoms.

The compounds of the formula II are preferably selected from the following formulae:

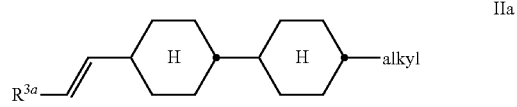

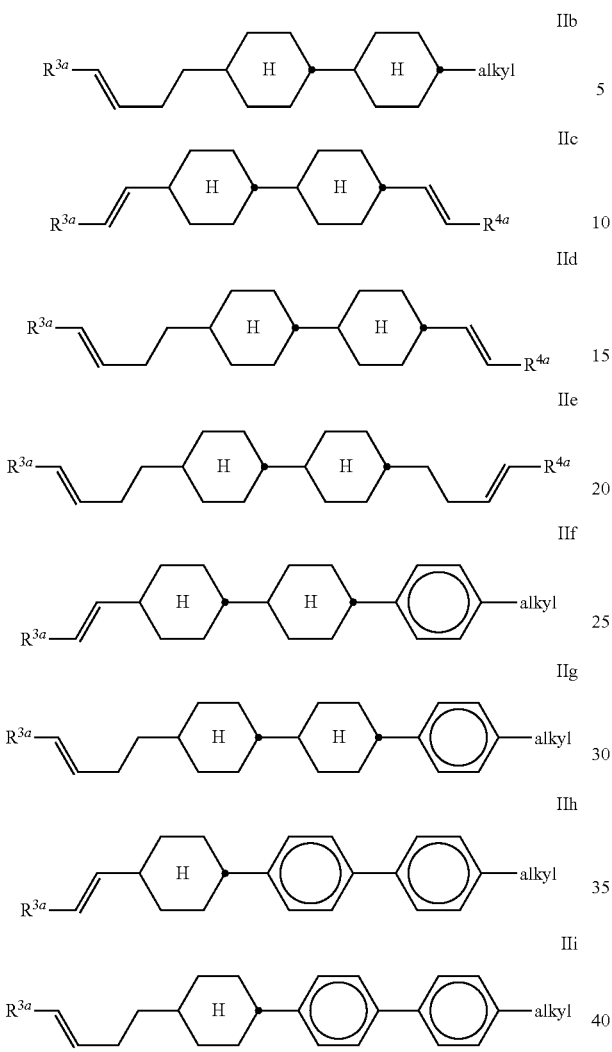

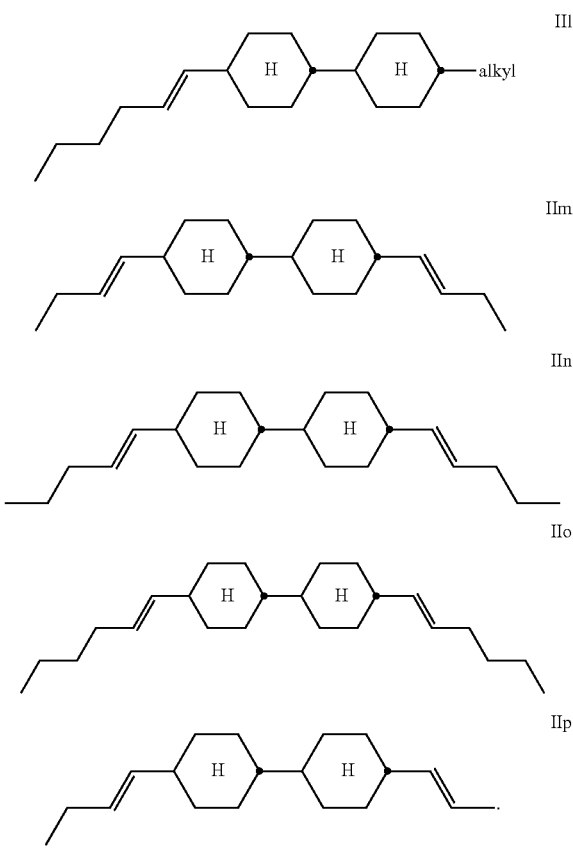

in which $R^{3a}$ and $R^{4a}$ each, independently of one another, denote H, $CH_3$, $C_2H_5$, $C_3H_7$, or $C_4H_9$, and "alkyl" denotes a straight-chain alkyl group having 1 to 8 C atoms. Particular preference is given to compounds of the formulae IIa and IIf, in particular in which $R^{3a}$ denotes H or $CH_3$, and compounds of the formula IIc, in particular in which $R^{3a}$ and $R^{4a}$ denote H, $CH_3$ or $C_2H_5$.

Preference is furthermore given to compounds of the formula II which have a non-terminal double bond in the alkenyl side chain:

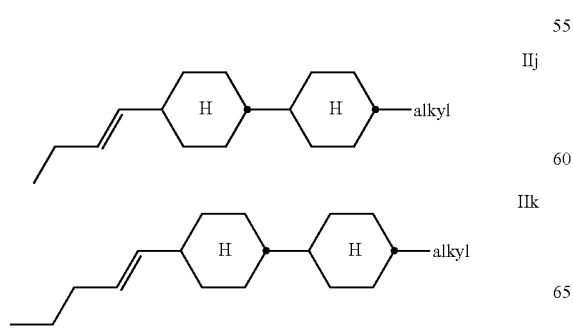

Very particularly preferred compounds of the formula II are the compounds of the formulae

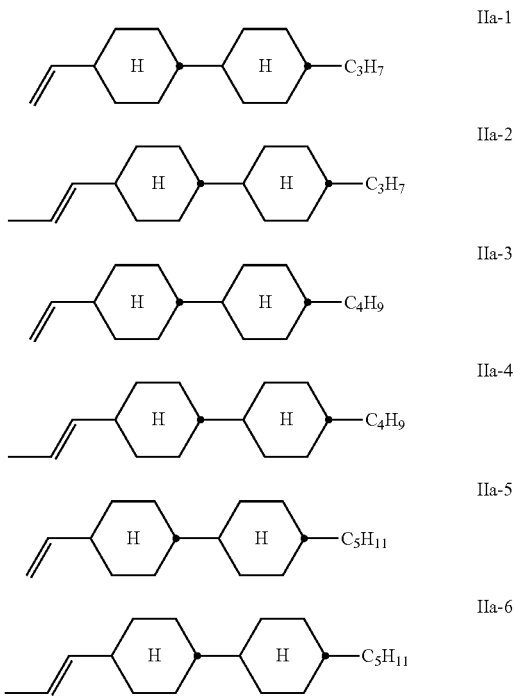

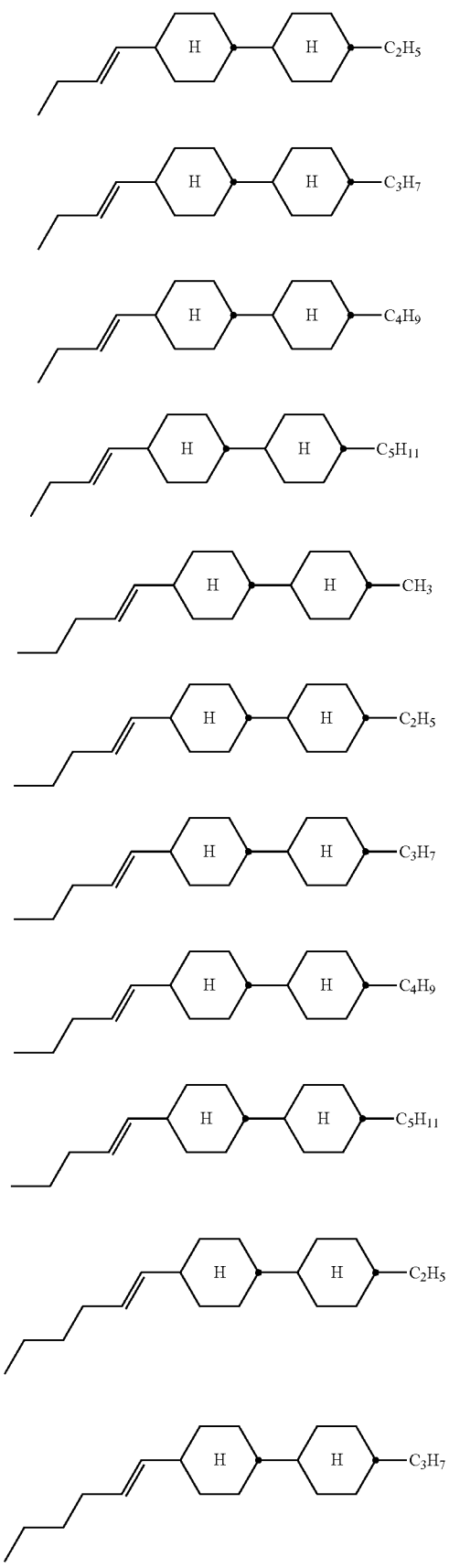

Of the compounds of the formulae IIa-1 to IIa-19, particular preference is given, in particular, to the compounds of the formulae IIa-1, IIa-2, IIa-3 and IIa-5.

Besides one or more compounds of the formula I, the liquid-crystalline media according to the invention particularly preferably comprise 5-70% by weight, in particular 10-50% by weight and very particularly preferably 15-40% by weight, of compounds of the formula IIa-1

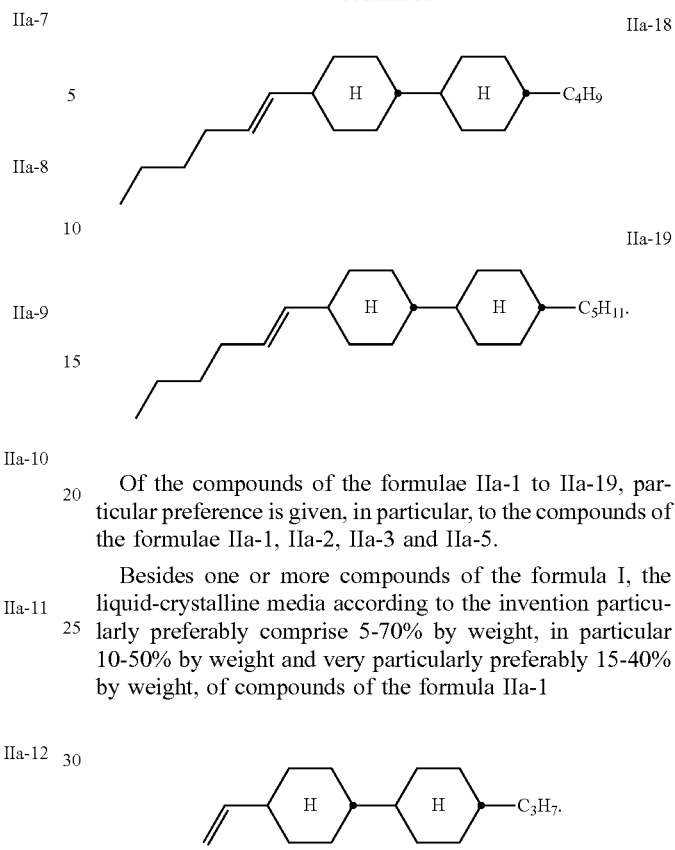

The compounds of the formula III are preferably selected from the following formulae:

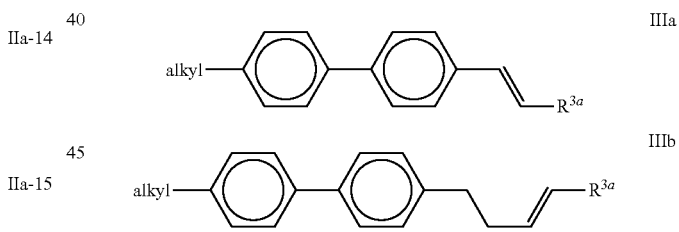

in which "alkyl" and $R^{3a}$ have the meanings indicated above, and $R^{3a}$ preferably denotes H or $CH_3$. Particular preference is given to compounds of the formula IIIb.

Very particular preference is given to the compound of the formula IIIb-1,

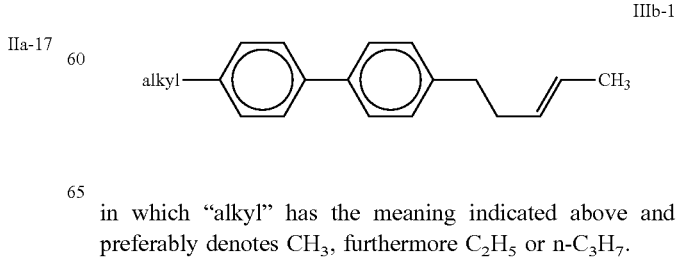

in which "alkyl" has the meaning indicated above and preferably denotes $CH_3$, furthermore $C_2H_5$ or n-$C_3H_7$.

The medium preferably comprises one or more compounds selected from the following formulae IV to VIII:

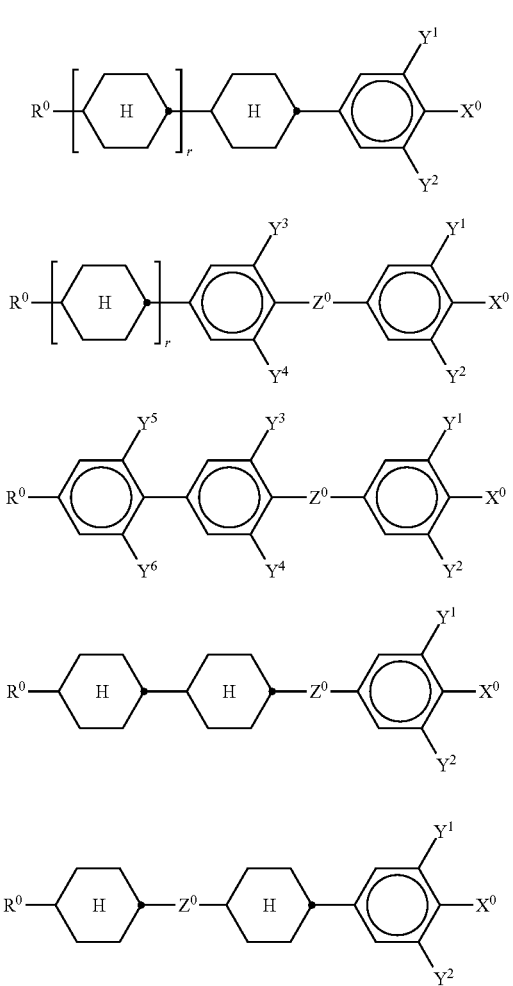

in which
R⁰ denotes an alkyl or alkoxy radical having 1 to 15 C atoms, where, in addition, one or more CH₂ groups in these radicals may each be replaced, independently of one another, by —C≡C—, —CF₂O—, —CH=CH—,

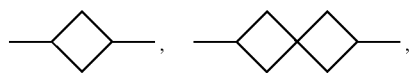

—O—, —CO—O— or —O—CO— in such a way that O atoms are not linked directly to one another, and in which, in addition, one or more H atoms may each be replaced by halogen,
X⁰ denotes F, Cl, a mono- or polyfluorinated alkyl or alkoxy radical, in each case having 1 to 6 C atoms, a mono- or polyfluorinated alkenyl or alkenyloxy radical, in each case having 2 to 6 C atoms,
Y¹⁻⁶ each, independently of one another, denote H or F,
Z⁰ denotes —C₂H₄—, —(CH₂)₄—, —CH=CH—, —CF=CF—, —C₂F₄—, —CH₂CF₂—, —CF₂CH₂—, —CH₂O—, —OCH₂—, —COO—, —CF₂O— or —OCF₂—, in the formulae V and VI also a single bond, and
r denotes 0 or 1.

In the above formulae, X⁰ is preferably F, Cl or a mono- or polyfluorinated alkyl or alkoxy radical having 1, 2 or 3 C atoms or a mono- or polyfluorinated alkenyl radical or alkenyloxy radical having 2 or 3 C atoms. X⁰ is particularly preferably F, Cl, CF₃, CHF₂, OCF₃, OCHF₂, OCHFCF₃, OCHFCHF₂, OCHFCH₂F, OCF₂CH₃, OCF₂CHF₂, OCF₂CH₂F, OCF₂CF₂CHF₂, OCF₂CF₂CH₂F, OCFHCF₂CF₃, OCFHCF₂CHF₂, OCH=CF₂, OCF=CF₂, OCF₂CHFCF₃, OCF₂CF₂CF₃, OCF₂CF₂CClF₂, OCClFCF₂CF₃, CF=CF₂, CF=CHF, OCH=CF₂, OCF=CF₂ or CH=CF₂.

In the compounds of the formulae IV to VIII, X⁰ preferably denotes F or OCF₃, furthermore OCHF₂, CF₃, CF₂H, Cl, OCH=CF₂. R⁰ is preferably straight-chain alkyl or alkenyl having up to 6 C atoms.

The compounds of the formula IV are preferably selected from the following formulae:

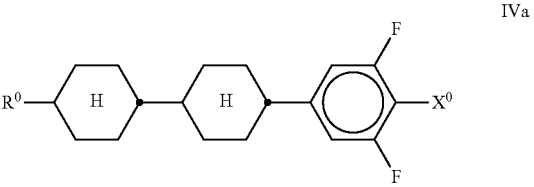

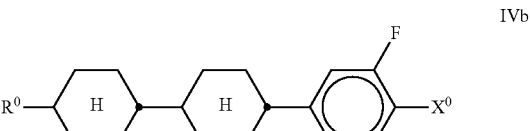

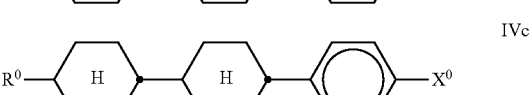

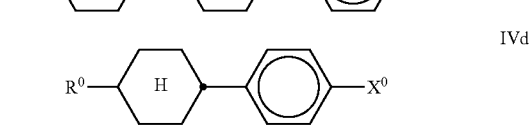

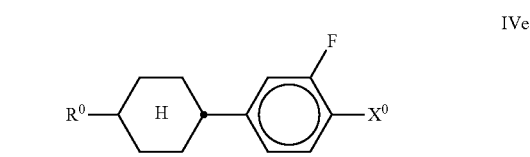

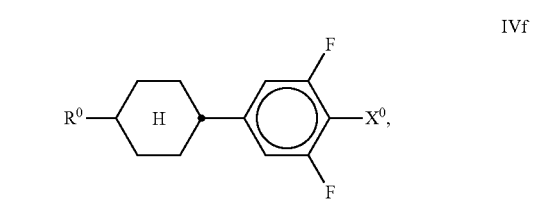

in which R⁰ and X⁰ have the meanings indicated under formula IV.

Preferably, R⁰ in formula IV and its subformulae denotes alkyl having 1 to 8 C atoms and X⁰ denotes F, Cl, OCHF₂ or OCF₃, furthermore OCH=CF₂. In the compound of the formula IVb, R⁰ preferably denotes alkyl or alkenyl. In the compound of the formula IVd, X⁰ preferably denotes Cl, furthermore F.

The compounds of the formula V are preferably selected from the formulae Va to Vj, Va
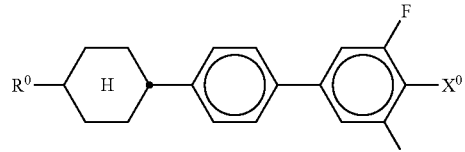

Vb
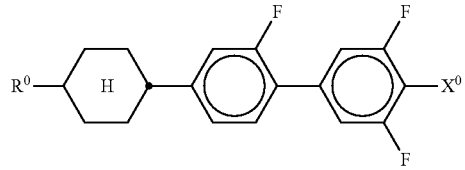

Vc
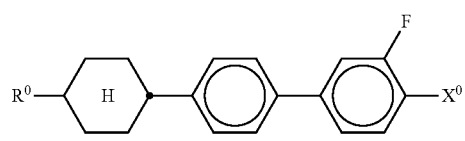

Vd
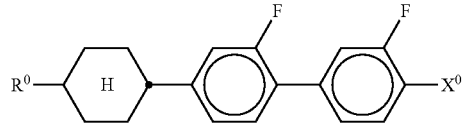

Ve
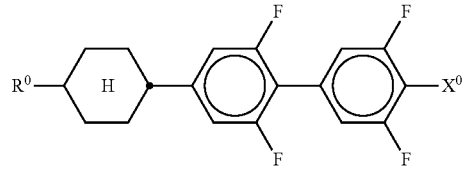

Vf
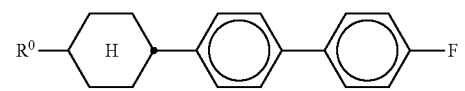

Vg
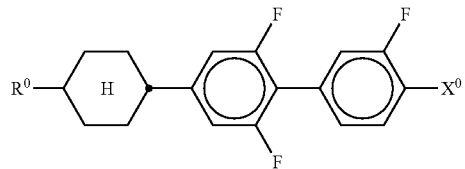

Vh
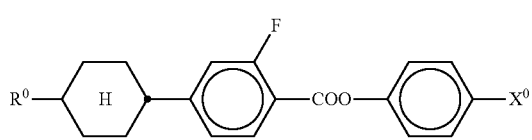

Vi
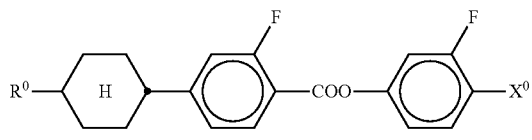

Vj
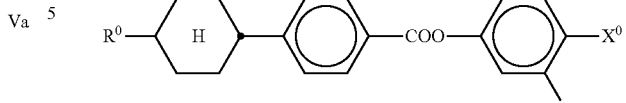

in which $R^0$ and $X^0$ have the meanings indicated under formula V. Preferably, $R^0$ in formula V and subformulae Va to Vj denotes alkyl having 1 to 8 C atoms and $X^0$ denotes F, $OCF_3$ or $OCH=CF_2$.

The medium comprises one or more compounds of the formula VI-1,

VI-1
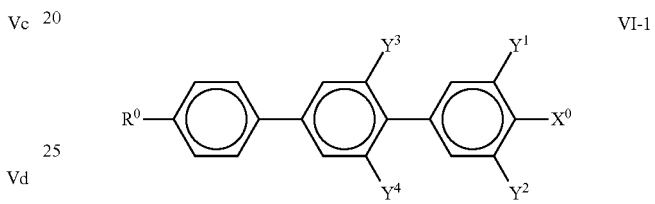

particularly preferably those selected from the following formulae:

VI-1a
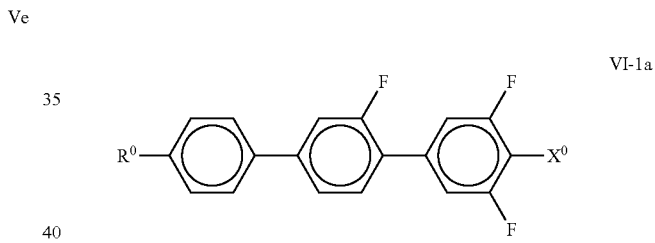

VI-1b
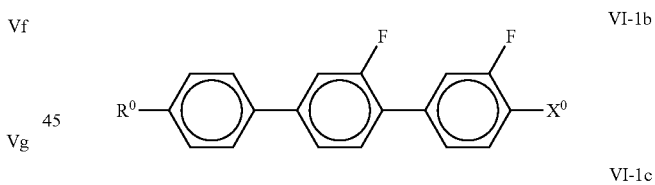

VI-1c
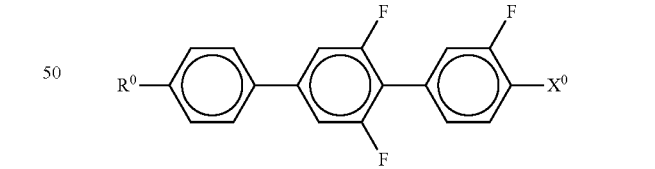

VI-1d
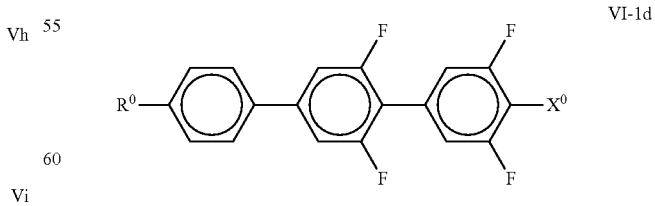

in which $R^0$ and $X^0$ have the meanings indicated under formula VI. Preferably, $R^0$ in formula VI and subformulae VI-1a to VI-1d denotes alkyl having 1 to 8 C atoms and $X^0$ denotes F, furthermore $CF_3$ and $OCF_3$.

The medium comprises one or more compounds of the formula VI-2,

VI-2
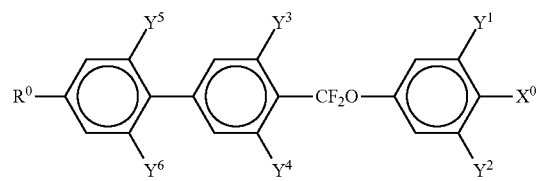

particularly preferably those selected from the following formulae:

VI-2a
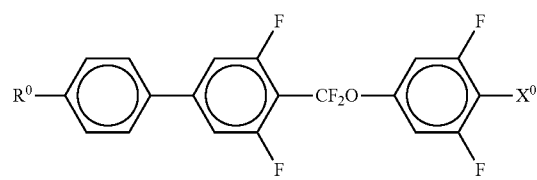

VI-2b

VI-2c
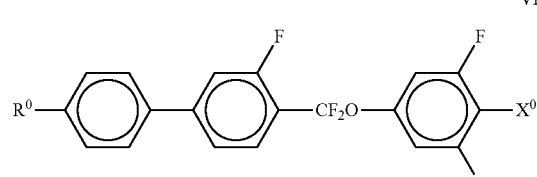

VI-2d

VI-2e
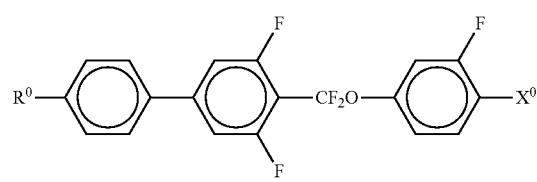

VI-2f
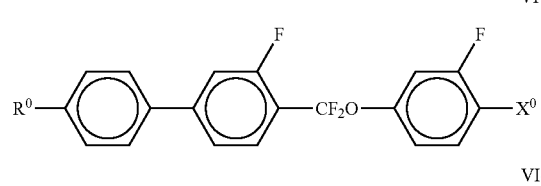

VI-2g, VI-2h
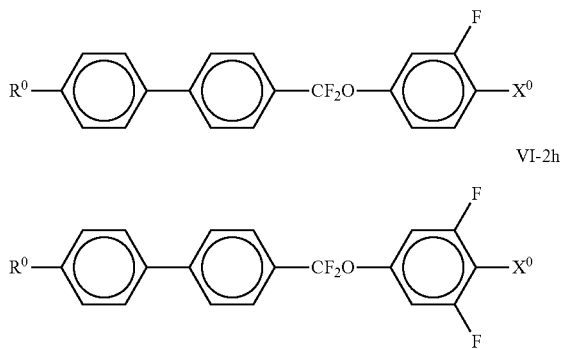

in which $R^0$ and $X^0$ have the meanings indicated under formula VI. Preferably, $R^0$ in subformulae VI-2a to VI-2h denotes alkyl having 1 to 8 C atoms and $X^0$ denotes F;

The medium preferably comprises one or more compounds of the formula VII in which $Z^0$ denotes —CF$_2$O—, —CH$_2$CH$_2$— or —COO—, particularly preferably those selected from the following formulae:

VII-1a
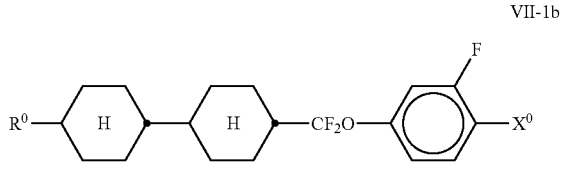

VII-1b
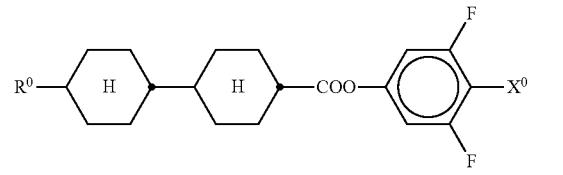

VII-1c
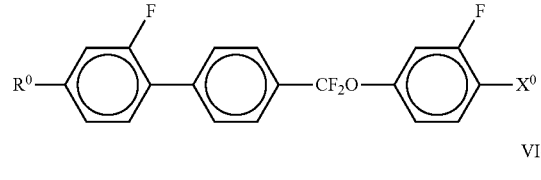

VII-1d
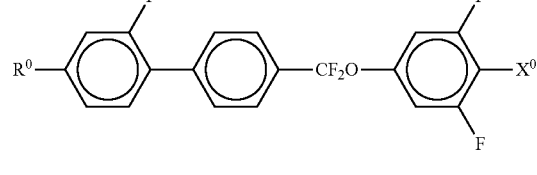

in which $R^0$ and $X^0$ have the meanings indicated under formula VII. Preferably, $R^0$ in formula VII and subformulae VII-1a to VII-1d denotes alkyl having 1 to 8 C atoms and $X^0$ denotes F, furthermore OCF$_3$ and CF$_3$.

The compounds of the formula VIII are preferably selected from the following formulae:

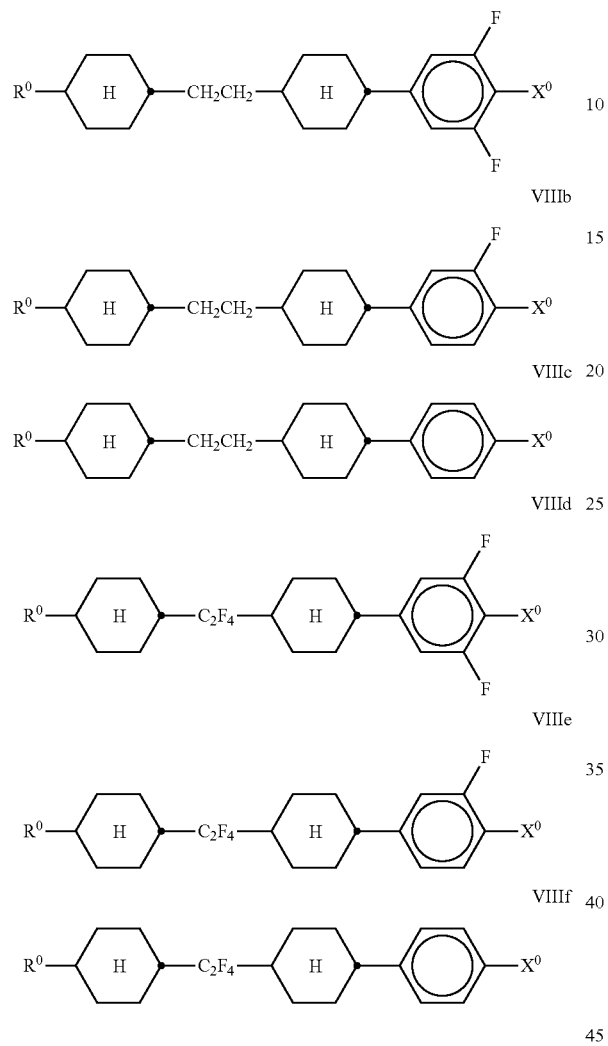

VIIIa
VIIIb
VIIIc
VIIId
VIIIe
VIIIf in which $R^0$ and $X^0$ have the meanings indicated under formula VIII. $R^0$ in formula VIII and subformulae VIIIa to VIIIf preferably denotes a straight-chain alkyl radical having 1 to 8 C atoms. $X^0$ preferably denotes F.

The medium comprises one or more compounds of the following formula:

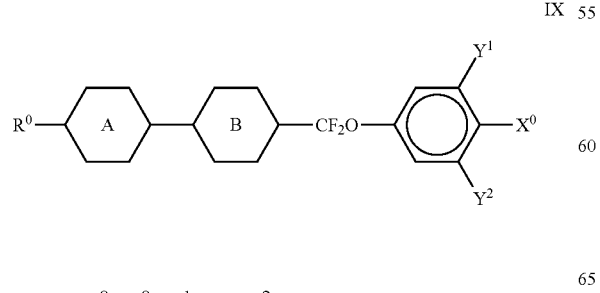

IX in which $R^0$, $X^0$, $Y^1$ and $Y^2$ have the meanings indicated under formula IV, and

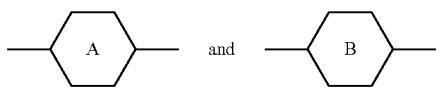

each, independently of one another, denote

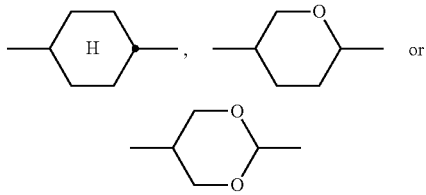

where the rings A and B do not both simultaneously denote 1,4-cyclohexylene;

The compounds of the formula IX are preferably selected from the following formulae:

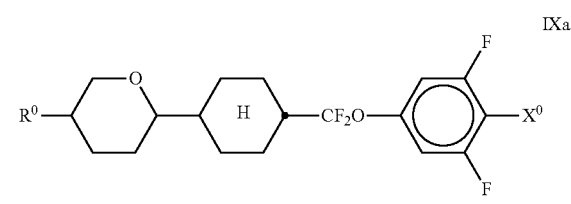

IXa
IXb
IXc

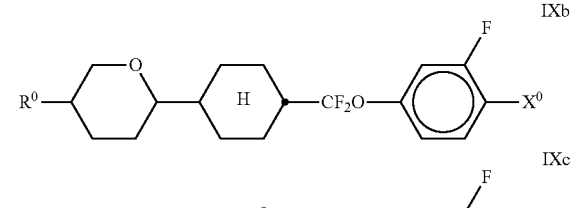

IXd
IXe

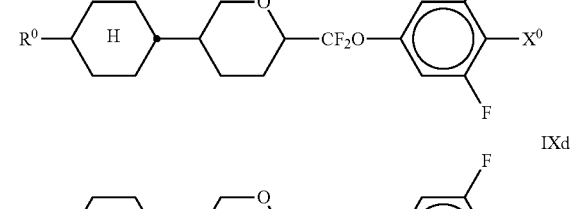

IXf

-continued

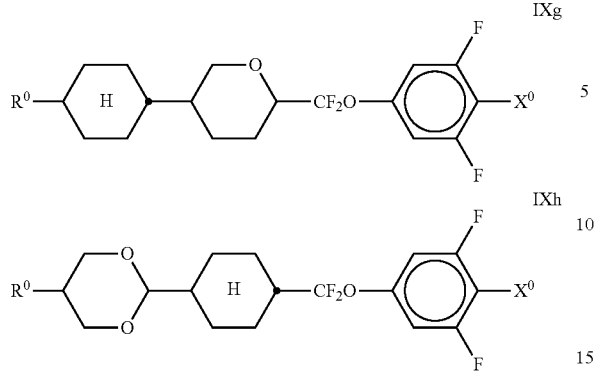

in which R⁰ and X⁰ have the meanings indicated under formula IX. Preferably, R⁰ in formula IX and subformulae IXa to IXh denotes alkyl having 1 to 8 C atoms and X⁰ denotes F. Particular preference is given to compounds of the formula IXa;

The medium comprises one or more compounds selected from the following formulae:

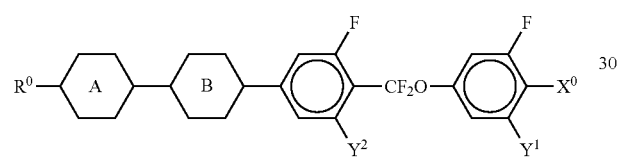

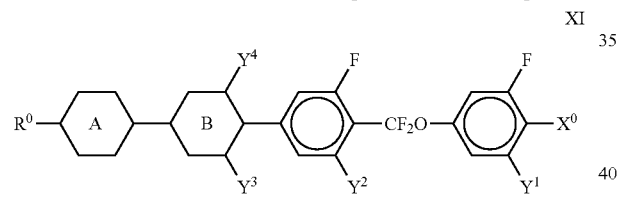

in which R⁰, X⁰ and $Y^{1-2}$ have the meanings indicated under formula IV, $Y^3$ and $Y^4$ each, independently of one another, denote H or F, and

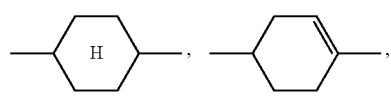

each, independently of one another, denote

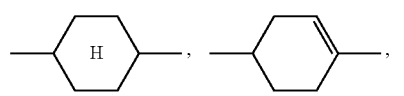

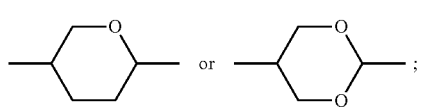

The compounds of the formulae X and XI are preferably selected from the following formulae:

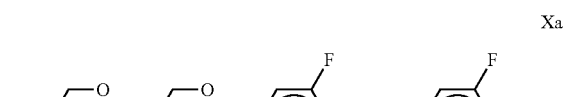

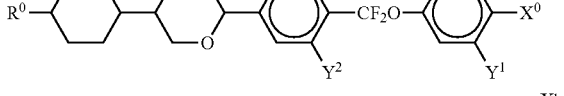

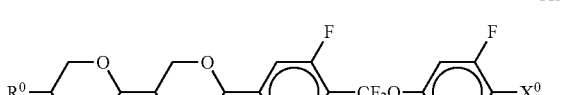

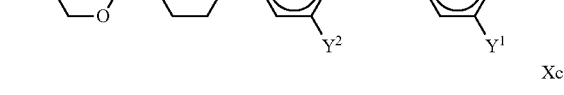

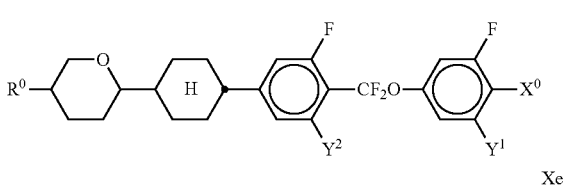

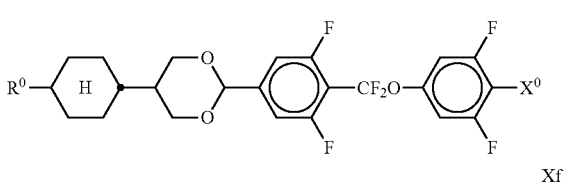

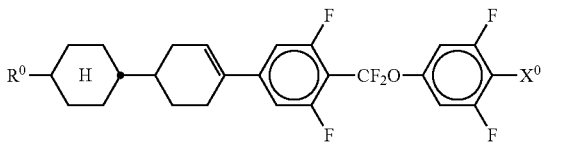

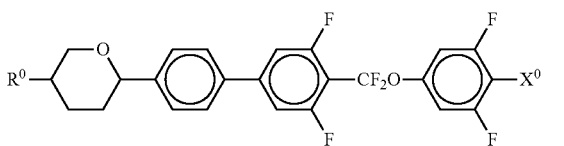

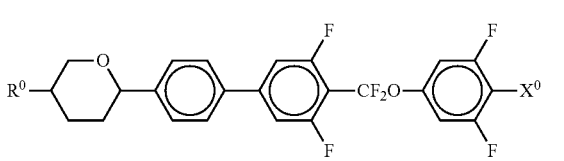

in which R⁰ and X⁰ have the meanings indicated under formulae X and XI. Preferably, R⁰ denotes alkyl having 1 to 8 C atoms and X⁰ denotes F. Particularly preferred compounds are those in which $Y^1$ denotes F and $Y^2$ denotes H or F, preferably F;

The medium comprises one or more compounds of the following formula XII:

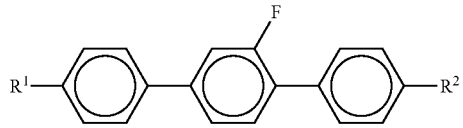

in which R¹ and R² each, independently of one another, denote alkyl, alkenyl, alkoxy, oxaalkyl, fluoroalkyl or alkenyloxy, each having up to 9 C atoms, and preferably each, independently of one another, denote alkyl or alkenyl having 1 to 8 C atoms or 2 to 8 C atoms respectively.

Preferred compounds of the formula XII are the compounds of the formulae

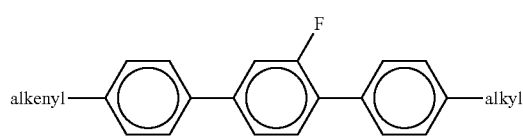

XII-1

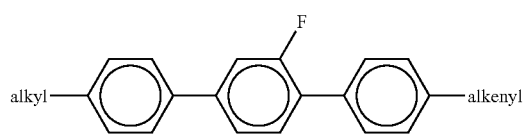

XII-2

XII-3

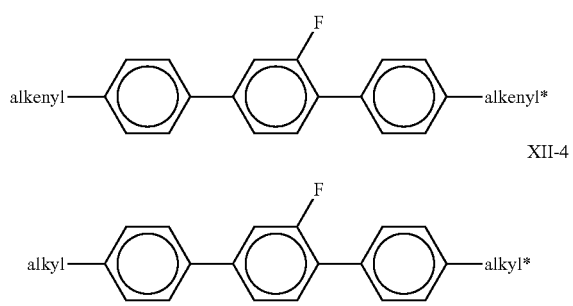

XII-4 in which
alkyl and alkyl* each, independently of one another, denote a straight-chain alkyl radical having 1 to 8 C atoms, and
alkenyl and alkenyl* each, independently of one another, denote a straight-chain alkenyl radical having 2 to 8 C atoms.

Particular preference is given to the compounds of the formulae XII-2 and XII-4.

Particularly preferred compounds of the formula XII-2 are the compounds of the formulae XII-2a, XII-2b and XII-2c:

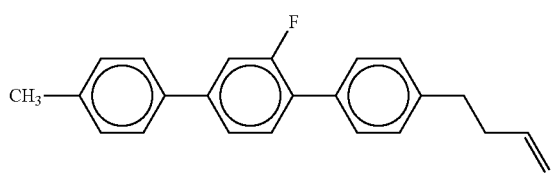

XII-2a

XII-2b

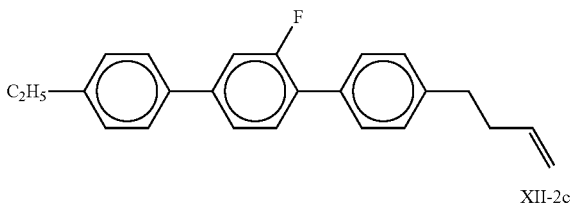

XII-2c

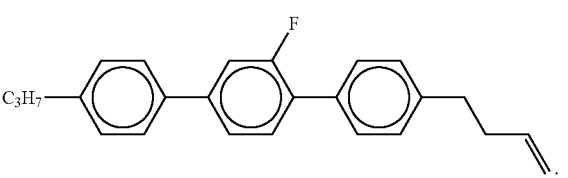

Particularly preferred compounds of the formula XII-4 are the compounds of the formulae XII-4a, XII-4b and XII-4c:

XII-4a

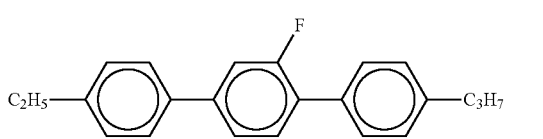

XII-4b

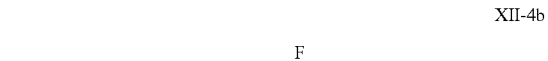

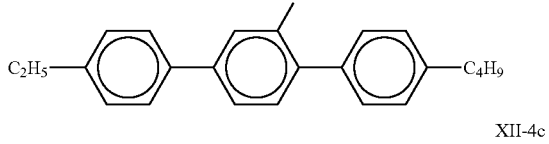

XII-4c

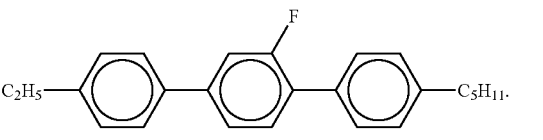

The medium comprises one or more compounds selected from the following formulae:

XIII

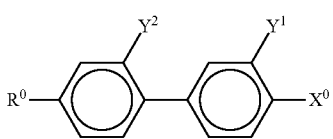

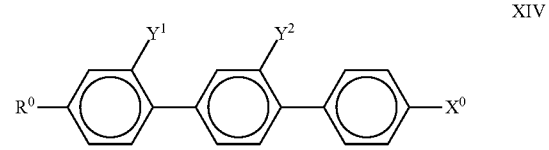

XIV

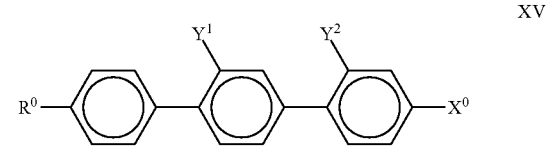

XV

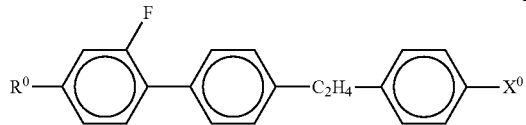
XVI in which $R^0$, $X^0$, $Y^1$ and $Y^2$ have the meanings indicated under formula IV. Preferably, $R^0$ denotes alkyl having 1 to 8 C atoms and $X^0$ denotes F or Cl;

The compounds of the formulae XIII, XIV and XV are preferably selected from the compounds of the formulae

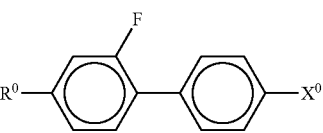
XIIIa

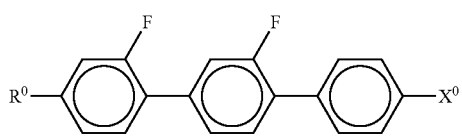
XIVa

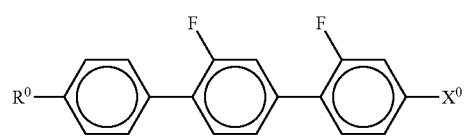
XVa in which $R^0$ and $X^0$ have the meanings indicated under formulae XII-XV. $R^0$ preferably denotes alkyl having 1 to 8 C atoms. In the compounds of the formula XIII, $X^0$ preferably denotes F or Cl.

The medium comprises one or more compounds of the formulae D1, D2, D3, D4 and/or D5,

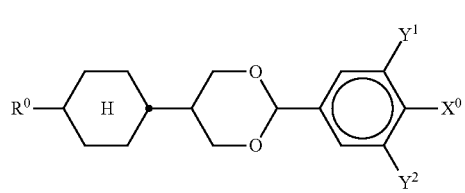
D1

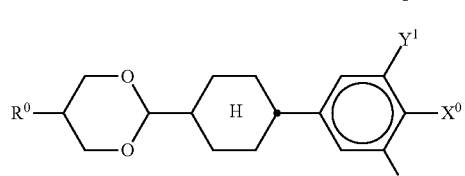
D2

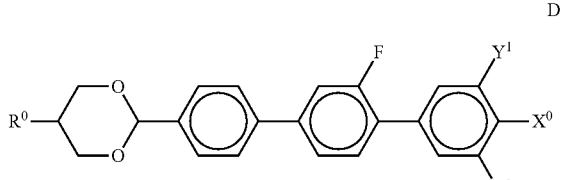
D3

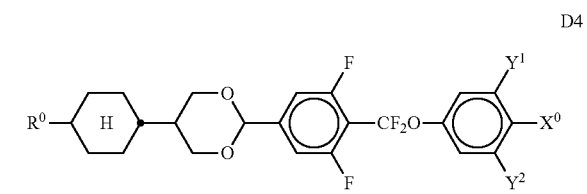
D4

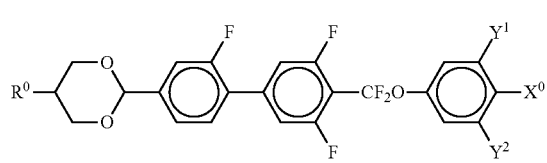
D5 in which $Y^1$, $Y^2$, $R^0$ and $X^0$ have the meanings indicated under formula IV. Preferably, $R^0$ denotes alkyl having 1 to 8 C atoms and $X^0$ denotes F. $Y^1$ and $Y^2$ preferably both denote F.

Particular preference is given to compounds of the formulae

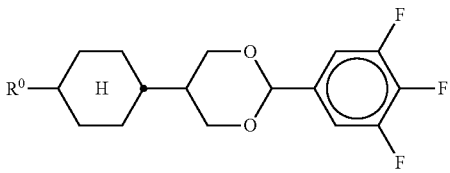
D1-1

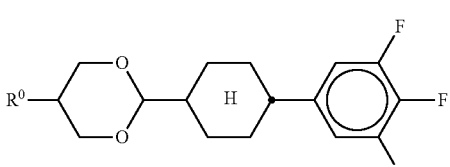
D2-1

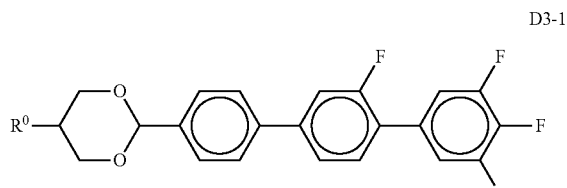
D3-1

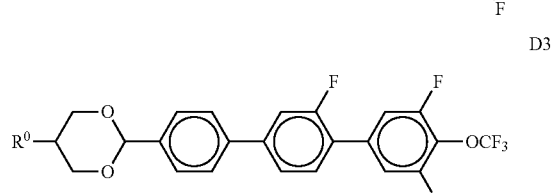
D3-2

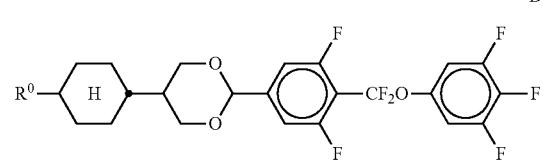
D4-1 in which R⁰ has the meaning indicated under formulae D1 to D5 and preferably denotes straight-chain alkyl having 1 to 6 C atoms, in particular $C_2H_5$, n-$C_3H_7$ or n-$C_5H_{11}$.

The medium comprises one or more compounds of the following formula XVII:

XVII in which $Y^1$, and $Y^2$ have the meanings indicated above. $R^1$ and $R^2$ each, independently of each other, denote alkyl or alkoxy radical having 1 to 15 C atoms, where, in addition, one or more CH2 groups in these radicals may each be replaced, independently of one another, by —C≡C—, —CF2O—, —CH=CH—, —O—, —CO—O— or —O—CO— in such a way that O atoms are not linked directly to one another, and in which, in addition, one or more H atoms may each be replaced by halogen. $R^1$ and $R^2$ preferably each, independently of one another, denote alkyl or alkenyl having 1 or 2 to 8 C atoms; $Y^1$ and $Y^2$ preferably both denote F.

The medium comprises one or more compounds of the following formula:

XVIII in which $X^0$, $Y^1$ and $Y^2$ have the meanings indicated under formula IV, and "alkenyl" denotes $C_{2-7}$-alkenyl. Particular preference is given to compounds of the following formula:

XVIIIa in which $R^{3a}$ has the meaning indicated under formulae IIa to IIi and preferably denotes H;

The medium additionally comprises one or more tetracyclic compounds selected from the formulae XIX to XXVIII,

XXVII

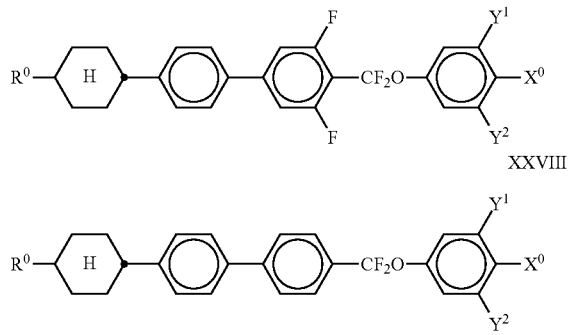

XXVIII in which $Y^{1-4}$, $R^0$ and $X^0$ each, independently of one another, have one of the meanings indicated under formula V. $X^0$ is preferably F, Cl, $CF_3$, $OCF_3$ or $OCHF_2$. $R^0$ preferably denotes alkyl, alkoxy, oxaalkyl, fluoroalkyl or alkenyl, each having up to 8 C atoms.

In the compounds of the formulae XIX to XXVIII, $R^0$ preferably denotes straight-chain alkyl. $X^0$ is preferably F or $OCF_3$, furthermore $CF_3$. $Y^1$ and $Y^2$ preferably denote $Y^1=F$ and $Y^2=H$ or $Y^1=Y^2=F$.

Particularly preferred compounds of the formulae XIX to XXVIII are the compounds of the formula XXV in which $X^0$ preferably denotes F, furthermore $OCF_3$.

Preferred mixtures comprise at least one compound from the group S-1, S-2, S-3 and S-4,

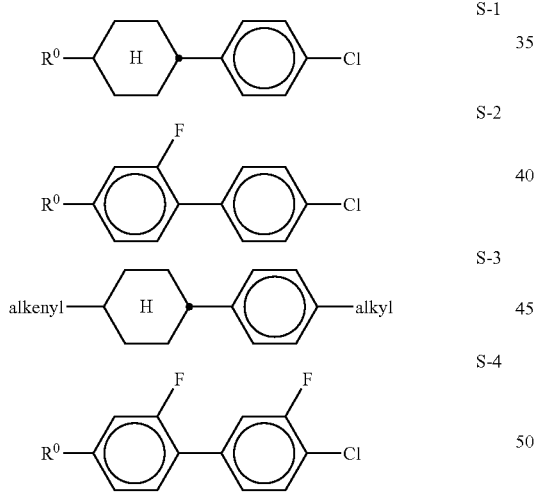

in which $R^0$ has one of the meanings indicated under formula IV, since these compounds help, inter alia, to suppress the smectic phases of the mixtures.

The medium preferably comprises one or more neutral compounds of the general formula N,

in which $R^{N1}$ and $R^{N2}$ each, independently of one another, denote an alkyl or alkoxy radical having 1 to 15 C atoms, where, in addition, one or more $CH_2$ groups in these radicals may each be replaced, independently of one another, by $-C\equiv C-$, $-CF_2O-$,

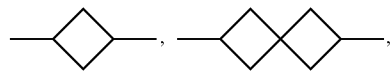

$-O-$, $-CO-O-$, or $-O-CO-$ in such a way that O atoms are not linked directly to one another, and in which, in addition, one or more H atoms may each be replaced by halogen, rings $A^{N1}$, $A^{N2}$ and $A^{N3}$ each, independently of one another, denote 1,4-phenylene, 2-fluoro-1,4-phenylene, 3-fluoro-1,4-phenylene, trans-1,4-cyclohexylene, in which, in addition, one or two $CH_2$ groups may each be replaced by $-O-$, or 1,4-cyclohexenylene, $Z^{N1}$ and $Z^{N2}$ each, independently of one another, denote a single bond, $-CH_2CH_2-$, $-COO-$, $-OCO-$, $-C\equiv C-$, $-CH_2O-$, $-OCH_2-$, $-CF_2O-$, $-OCF_2-$ or $-CH=CH-$, n denotes 0, 1 or 2.

Preferred compounds of the formula N are shown below:

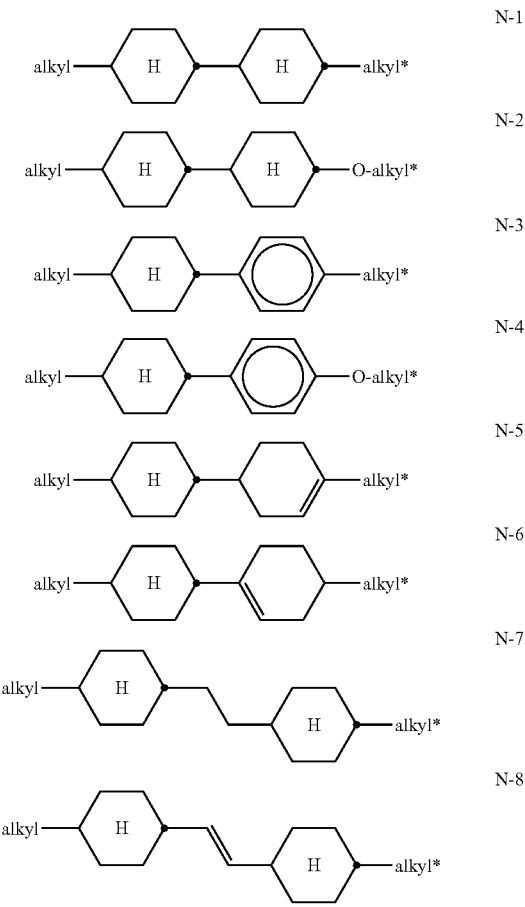

N-9
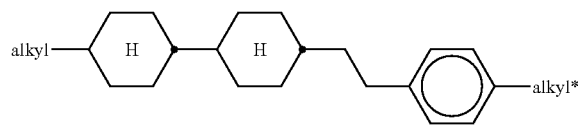
N-10
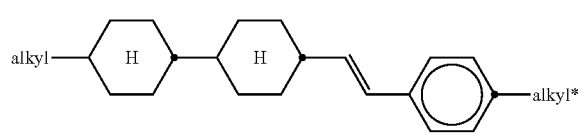
N-11
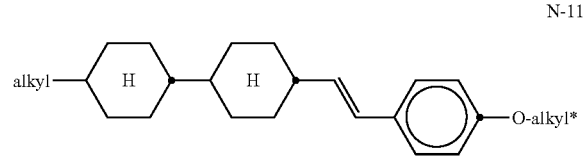
N-12
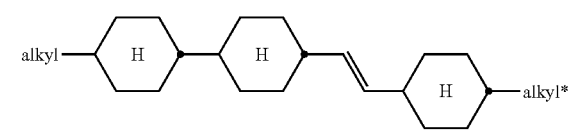
N-13
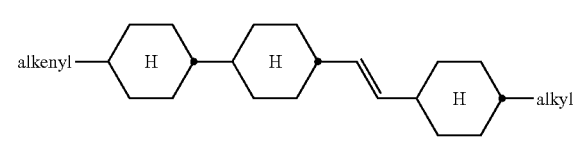
N-14
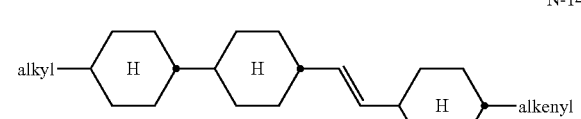
N-15
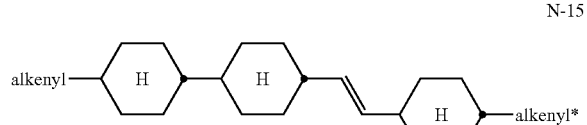
N-16
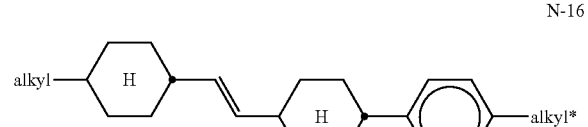
N-17
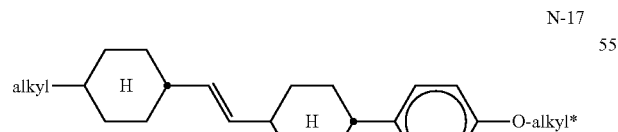
N-18
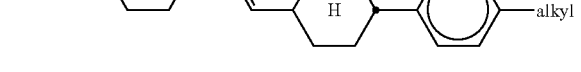
N-19
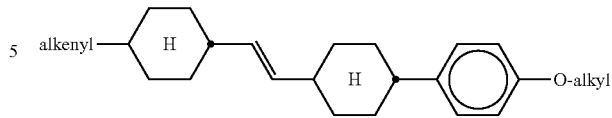
N-20
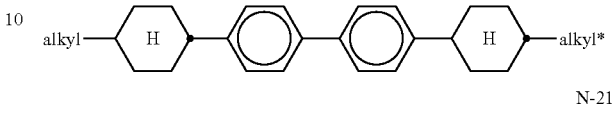
N-21
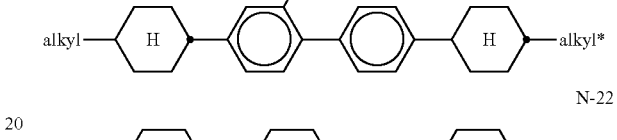
N-22
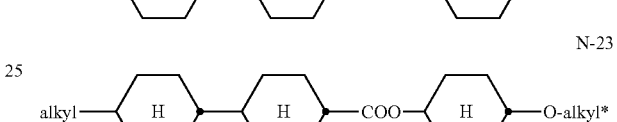
N-23
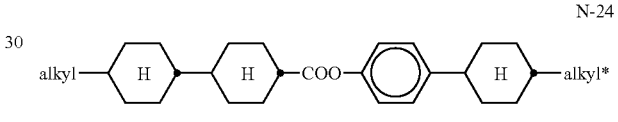
N-24
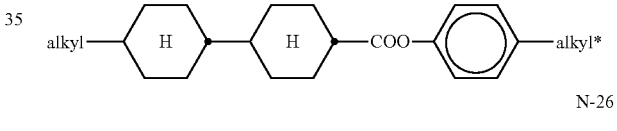
N-25
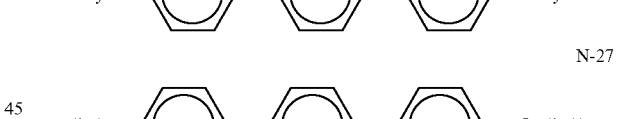
N-26
N-27
N-28
N-29
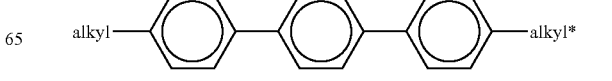
N-30

N-31

N-32
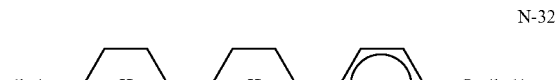

N-33

N-34
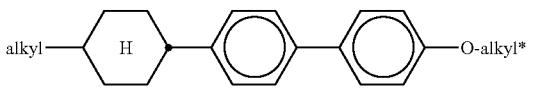

N-35

N-36
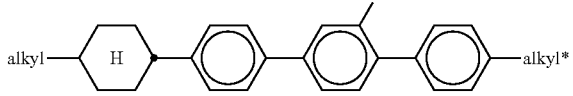

in which alkyl and alkyl* each, independently of one another, denote a straight-chain alkyl radical having 1 to 9 C atoms, preferably 2 to 6 C atoms, and alkenyl and alkenyl* each, independently of one another, denote a straight-chain alkenyl radical having 2-6 C atoms.

Of the compounds of the formula N, particular preference is given to the compounds of the formulae N-1, N-2, N-3, N-4, N-8, N-9, N-14, N-15, N-17, N-18, N-19, N-20, N-21, N-22, N-23, N-24, N-25, N-31, N-33 and N-36.

The medium additionally comprises one or more compounds of the formulae St-1 to St-3, St-1
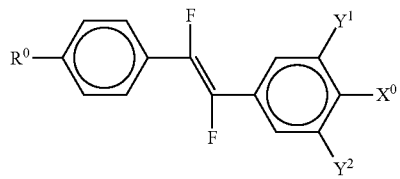

St-2
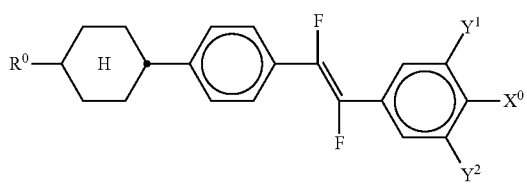

St-3
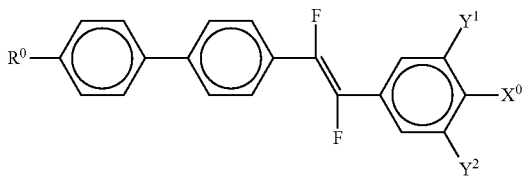

in which $R^0$, $Y^1$, $Y^2$ and $X^0$ have the meanings indicated under formula IV. $R^0$ preferably denotes straight-chain alkyl, preferably having 1-6 C atoms. $X^0$ is preferably F, $CF_3$ or $OCF_3$. $Y^1$ preferably denotes F. $Y^2$ preferably denotes F. Furthermore, preference is given to compounds in which $Y^1$=F and $Y^2$=H.

The medium comprises one or more pyrimidine or pyridine compounds of the formulae Py-1 to Py-5, Py-1

Py-2
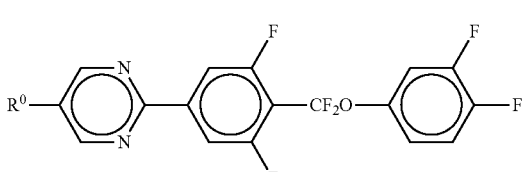

Py-3
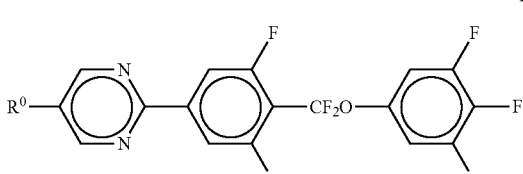

Py-4
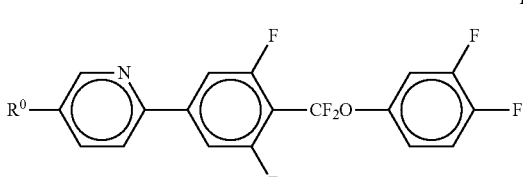

Py-5
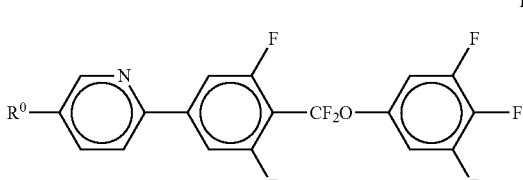

in which $R^0$ has one of the meanings indicated under formula IV, and preferably is straight-chain alkyl having 2-5 C atoms. x denotes 0 or 1, preferably x=1.

The medium comprises one or more compounds selected from the group of the compounds of the formulae Y-1, Y-2, Y-3 and Y-4,

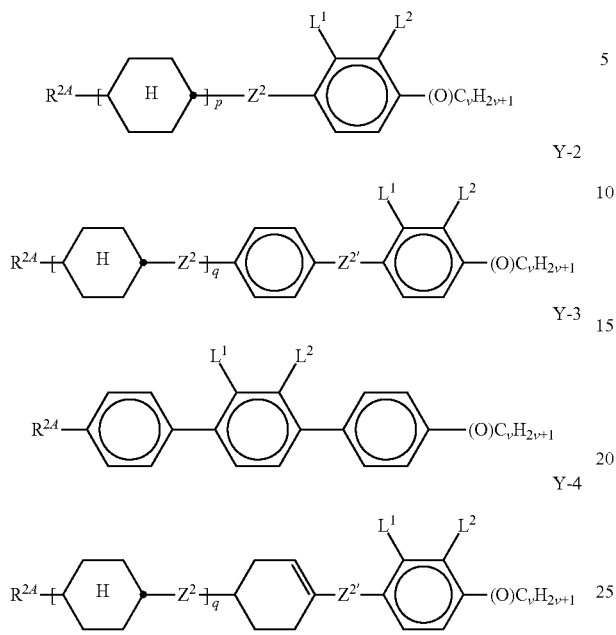

in which
R$^{2A}$ denotes H, an alkyl or alkoxy radical having 1 to 15 C atoms, where, in addition, one or more CH$_2$ groups in these radicals may each be replaced, independently of one another, by —C≡C—, —CF$_2$O—, —CH=CH—,

—O—, —CO—O— or —O—CO— in such a way that O atoms are not linked directly to one another, and in which, in addition, one or more H atoms may each be replaced by halogen, L$^1$ and L$^2$ each, independently of one another, denote F, Cl, CF$_3$ or CHF$_2$, preferably each denote F, Z$^2$ and Z$^{2\prime}$ each, independently of one another, denote a single bond, —CH$_2$CH$_2$—, —CH=CH—, —CF$_2$O—, —OCF$_2$—, —CH$_2$O—, —OCH$_2$—, —COO—, —OCO—, —C$_2$F$_4$—, —CF=CF— or —CH=CHCH$_2$O—, p denotes 0, 1 or 2,
q denotes 0 or 1,
(O)C$_\nu$H$_{2\nu+1}$ denotes OC$_\nu$H$_{2\nu+1}$ or C$_\nu$H$_{2\nu+1}$, and
v denotes 1 to 6.

Particularly preferred compounds of the formulae Y-1 to Y-4 are shown below:

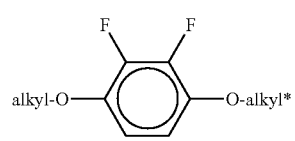

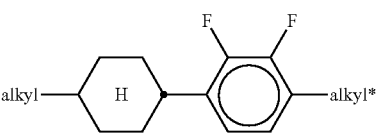

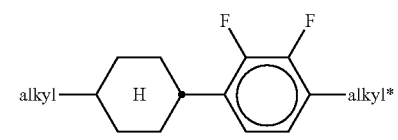

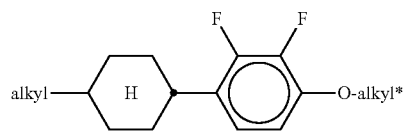

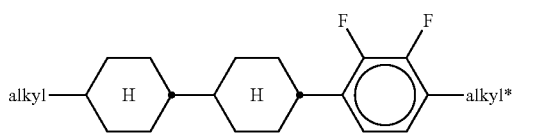

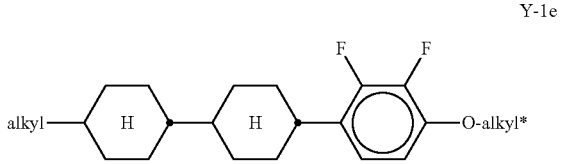

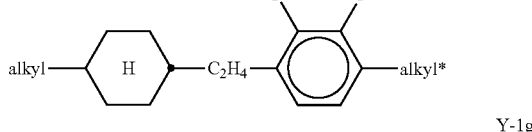

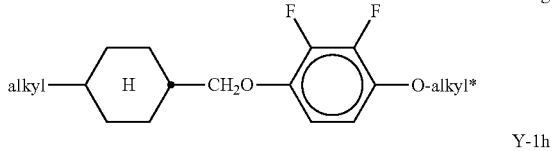

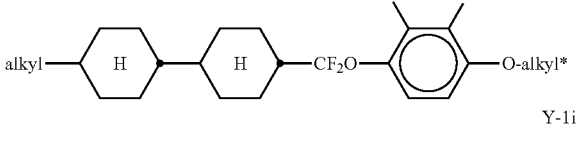

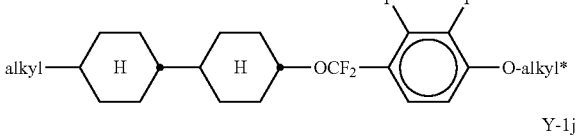

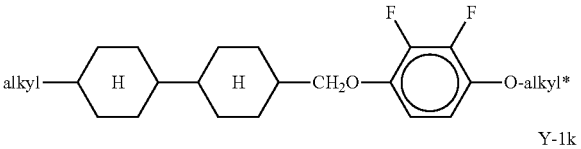

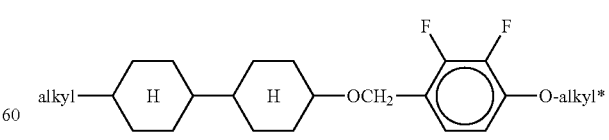

Y-1m 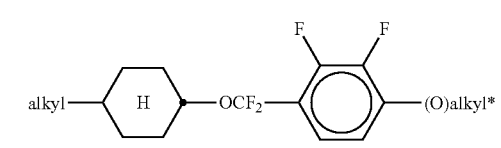
Y-1n 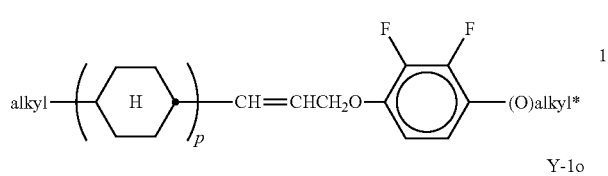
Y-1o
Y-1p 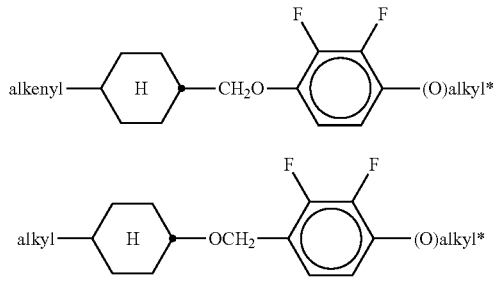
Y-1q
Y-1r 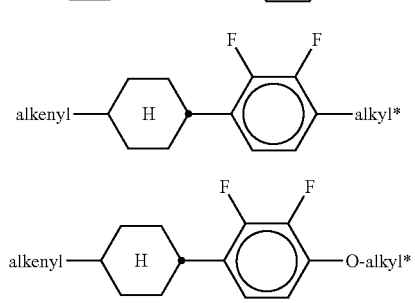
Y-1s
Y-1t 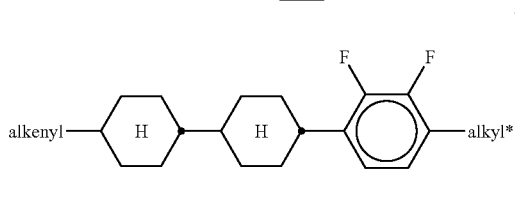
Y-1u
Y-1v 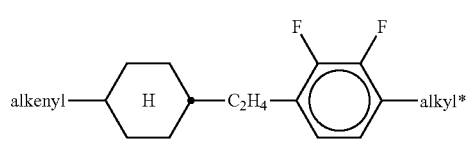
Y-2a 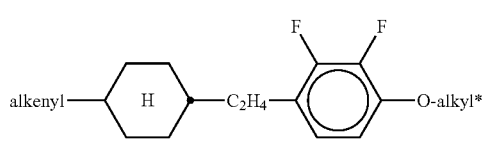
Y-2b 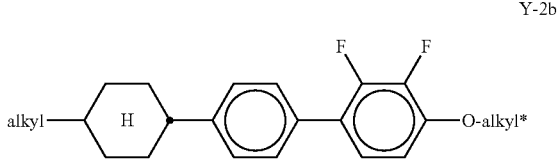
Y-2c 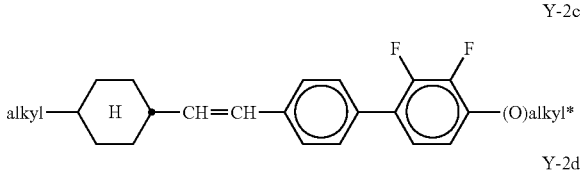
Y-2d
Y-2e 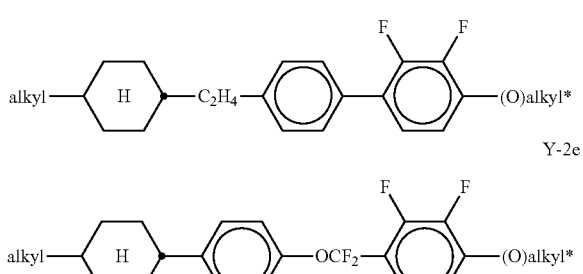
Y-2f
Y-2g 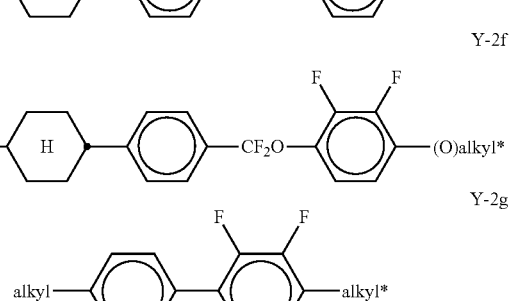
Y-2h
Y-2i 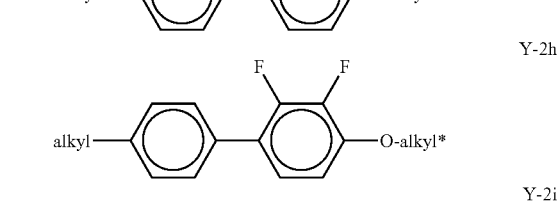
Y-2j 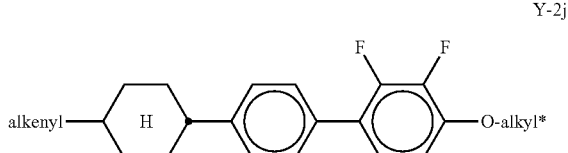
Y-3a 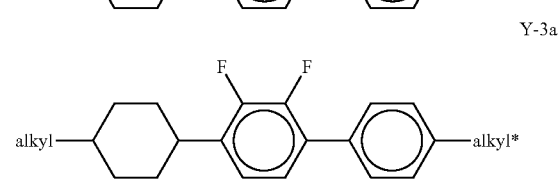
in which alkyl and alkyl* each, independently of one another, denote a straight-chain alkyl radical having 1 to 8 C atoms, alkenyl denotes a straight-chain alkenyl radical having 2 to 8 C atoms, and (O) denotes —O— or a single bond.

Of the said compounds, particular preference is given to the compounds of the formulae Y-1a, Y-1c, Y-1e, Y-1g, Y-1j, Y-1r, Y-1t, Y-2b, Y-2h, Y-2j and Y-3a.

In the formulae given above and below,

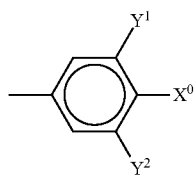

preferably denotes

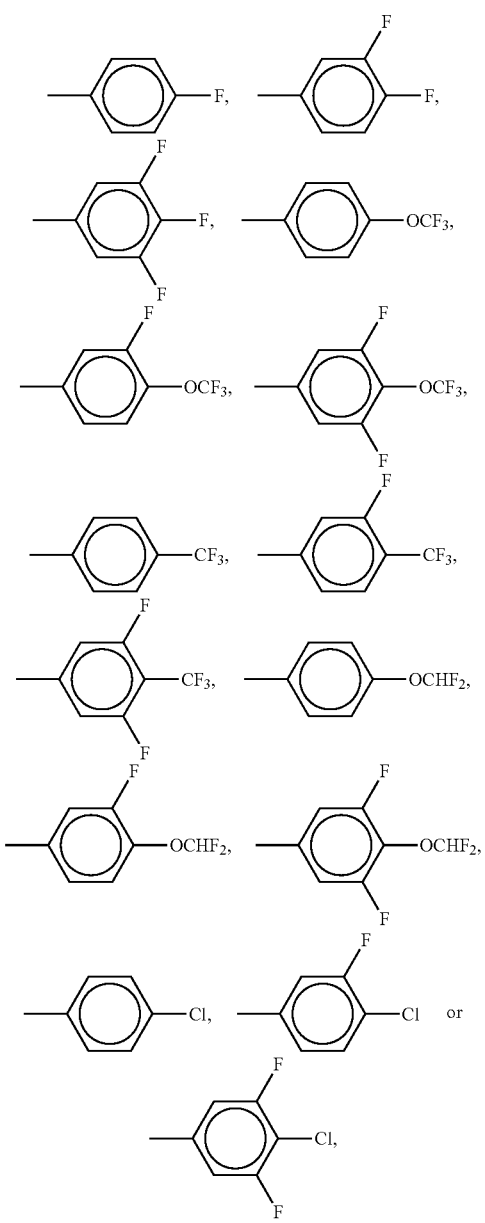

$R^0$ is preferably straight-chain alkyl or alkenyl having 2 to 7 C atoms;

$X^0$ is preferably F, furthermore $OCF_3$, $OCH=CF_2$, Cl or $CF_3$.

Other mesogenic compounds which are not mentioned explicitly above can also optionally and advantageously be used in the media in accordance with the present invention. Such compounds are known to the person skilled in the art.

The expression "alkyl" or "alkyl*" in this application encompasses straight-chain and branched alkyl groups having 1-7 carbon atoms, in particular the straight-chain groups methyl, ethyl, propyl, butyl, pentyl, hexyl and heptyl. Groups having 1-6 carbon atoms are generally preferred.

The expression "Oalkyl" in this application encompasses straight-chain and branched alkoxy groups.

The expression "alkenyl" or "alkenyl*" in this application encompasses straight-chain and branched alkenyl groups having 2-7 carbon atoms, in particular the straight-chain groups. Preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The expression "fluoroalkyl" in this application encompasses straight-chain groups having at least one fluorine atom, preferably a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The expression "oxaalkyl" or "alkoxy" in this application encompasses straight-chain radicals of the formula $C_nH_{2n+1}$—O—$(CH_2)_m$, in which n and m each, independently of one another, denote 1 to 6. m may also denote 0. Preferably, n=1 and m=1-6 or m=0 and n=1-3.

The individual compounds of the above-mentioned formulae and the subformulae thereof which can be used in the media according to the invention are either known or can be prepared analogously to the known compounds.

The liquid-crystal media in accordance with the present invention preferably have a clearing point of 70° C. or above, more preferably of 75° C. or above, particularly preferably of 80° C. or above and very particularly preferably of 85° C. or above.

The nematic phase of the media according to the invention preferably extends at least from 0° C. or below to 70° C. or above, more preferably at least from −20° C. or below to 75° C. or above, very preferably at least from −30° C. or below to 75° C. or above and in particular at least from −40° C. or below to 80° C. or above.

The optimum mixing ratio of the compounds of the above-mentioned formulae depends substantially on the desired properties, on the choice of the components of the above-mentioned formulae and on the choice of any further components that may be present.

The total amount of compounds of the above-mentioned formulae in the mixtures according to the invention is not crucial. The mixtures may therefore comprise one or more further components for the purposes of optimization of various properties. However, the observed effect on the desired improvement in the properties of the mixture is generally greater, the higher the total concentration of compounds of the above-mentioned formulae.

As already mentioned above, ECB displays, like ASV displays, use liquid-crystalline media having negative dielectric anisotropy (Δε), whereas TN and all conventional IPS displays to date use liquid-crystalline media having positive dielectric anisotropy.

In a preferred embodiment, the present invention therefore relates to a liquid-crystalline medium having positive dielectric anisotropy.

Preferred compounds which, besides one, two or more compounds of the formula I, can be employed in a liquid-crystalline medium according to the invention having positive dielectric anisotropy are indicated below:

The medium preferably comprises one or more compounds selected from the group of the compounds of the formulae I, II, III, V, VI-1, VI-2, XII, XIII, XIV, XVII, XXIII, XXV;

The medium preferably comprises one or more compounds of the formula VI-1;

The medium preferably comprises one or more compounds of the formula VI-2;

The proportion of compounds of the formulae II-XXVII in the mixture as a whole is preferably 20 to 99% by weight;

The medium preferably comprises 25-80% by weight, particularly preferably 30-70% by weight, of compounds of the formulae II and/or III, The medium preferably comprises 0-70% by weight, particularly preferably 20-60% by weight, of compounds of the formula IIa-1;

The medium preferably comprises 0-25% by weight, particularly preferably 5-25% by weight, of compounds of the formula IIa-2;

The medium preferably comprises 0-30% by weight, particularly preferably 5-25% by weight, of compounds of the formula IIa-3;

The medium preferably comprises 0-25% by weight, particularly preferably 5-25% by weight, of compounds of the formula IIa-5;

The medium preferably comprises 5-40% by weight, particularly preferably 10-30% by weight, of compounds of the formula V;

The medium preferably comprises 3-30% by weight, particularly preferably 6-25% by weight, of compounds of the formula VI-1;

The medium preferably comprises 2-30% by weight, particularly preferably 4-25% by weight, of compounds of the formula VI-2;

The medium comprises 2-40% by weight, particularly preferably 5-30% by weight, of compounds of the formula XII;

The medium preferably comprises 1-25% by weight, particularly preferably 2-15% by weight, of compounds of the formula XIII;

The medium preferably comprises 5-45% by weight, particularly preferably 10-35% by weight, of compounds of the formula XIV;

The medium preferably comprises 1-20% by weight, particularly preferably 2-15% by weight, of compounds of the formula XVI;

The medium preferably comprises 5-30% by weight, particularly preferably 8-22% by weight, of compounds of the formula Va in which $X^0$=OCH=CF$_2$.

In a particularly preferred embodiment, the media according to the invention having positive dielectric anisotropy comprise compounds of the formulae IV to VIII in which $X^0$ denotes F, OCF$_3$, OCHF$_2$, OCH=CF$_2$, OCF=CF$_2$ or OCF$_2$—CF$_2$H. A favorable synergistic action with the compounds of the formula I results in particularly advantageous properties. In particular, mixtures comprising compounds of the formulae VI, or XI, or VI and XI are distinguished by their low threshold voltages.

The invention thus also relates to electro-optical displays, such as, for example, TN, STN, TFT, OCB, IPS, PS-IPS, FFS, PS-FFS, positive VA or MLC displays, having two plane-parallel outer plates, which, together with a frame, form a cell, integrated non-linear elements for switching individual pixels on the outer plates, and a nematic liquid-crystal mixture having positive dielectric anisotropy and high specific resistance located in the cell, which contain media of this type, and to the use of these media for electro-optical purposes. The IPS and FFS displays may contain both LC mixtures having negative dielectric anisotropy and LC mixtures having positive dielectric anisotropy.

Furthermore, the mixtures according to the invention having positive dielectric anisotropy are also suitable for positive VA applications, also referred to as HT-VA applications. These are taken to mean electro-optical displays having an in-plane drive electrode configuration and homeotropic arrangement of the liquid-crystal medium having positive dielectric anisotropy.

The mixtures according to the invention having positive dielectric anisotropy are particularly preferred for TN-TFT display applications having a low operating voltage, i.e. particularly preferably for notebook applications.

The mixtures according to the invention having positive dielectric anisotropy are particularly suitable for mobile applications and high-Δn TFT applications, such as, for example, PDAs, notebooks, LCD TVs and monitors.

The liquid-crystal mixtures according to the invention having positive dielectric anisotropy, while retaining the nematic phase down to −20° C. and preferably down to −30° C., particularly preferably down to −40° C., and the clearing point ≥70° C., preferably ≥74° C., at the same time allow rotational viscosities $\gamma_1$ of ≤120 mPa·s, particularly preferably 60 mPa·s, to be achieved, enabling excellent MLC displays having fast response times to be achieved.

The dielectric anisotropy Δε of the liquid-crystal mixtures according to the invention having positive dielectric anisotropy is preferably ≥+3, particularly preferably ≥+4. In addition, the mixtures are characterized by low operating voltages. The threshold voltage of the liquid-crystal mixtures according to the invention is preferably ≤2.5 V, in particular ≤2.2 V.

The birefringence Δn of the liquid-crystal mixtures according to the invention having positive dielectric anisotropy is preferably ≥0.08, in particular ≥0.10.

If the mixtures according to the invention are used in IPS or FFS applications, the mixtures having positive dielectric anisotropy preferably have a dielectric anisotropy value of 3-20 and an optical anisotropy value of 0.07-0.13.

In an equally preferred embodiment, however, the present invention also relates to a liquid-crystalline medium having negative dielectric anisotropy.

Preferred compounds which, besides one, two or more compounds of the formula I, can be employed in a liquid-crystalline medium according to the invention having negative dielectric anisotropy are indicated below:

the medium preferably comprises one or more compounds of the formula II, preferably selected from the group of the compounds of the formulae CC-n-V and CC-n-Vm (See Table B), preferably CC-3-V, CC-3-V1, CC-4-V and CC-5-V, particularly preferably selected from the group of the compounds CC-3-V, CC-3-V1 and CC-4-

V, very particularly preferably the compound CC-3-V, and optionally additionally the compound CC-4-V and/or CC-3-V1, the medium preferably comprises the compound PP-1-2V1 (See Table B), the medium preferably comprises one or more compounds of the formula Y-1, preferably of the formula Y-1c, selected from the group of the compounds of the formulae CY-3-O2, CY-3-O4, CY-5-O2 and CY-5-O4 (See Table B), the medium preferably comprises one or more compounds of the formula Y-1, preferably selected from the group of the compounds of the formulae Y-1e and Y-1 d, preferably of the formula CCY-n-Om (See Table B), preferably selected from the group of the compounds of the formulae CCY-3-O2, CCY-2-O2, CCY-3-O1, CCY-3-O3, CCY-4-O2, CCY-3-O2 and CCY-5-O2, the medium preferably comprises one or more compounds of the formula Y-2, preferably of the formula Y-2b, preferably selected from the group of the compounds of the formulae CPY-2-O2, CPY-3-O2, CPY-4-O2 and CPY-5-O2 (See Table B), the medium preferably comprises one or more compounds of the formula Y-2h, preferably selected from the group of the compounds of the formulae PY-3-O2, PY-1-O4 and PY-4-O2 (See Table B), the medium preferably comprises one or more compounds of the formula Y-3, preferably selected from the group of the compounds of the formulae PYP-2-3 and PYP-2-4 (See Table B), the medium preferably optionally comprises one or more compounds of the formula Y-4, preferably of the formula CLY-n-Om, preferably selected from the group of the compounds of the formulae CLY-2-O4, CLY-3-O2 and CLY-3-O3 (See Table B), the medium preferably comprises compounds of the formulae II and Y-1 to Y-4 in an amount of 20 to 99% by weight in the mixture as a whole, the medium preferably comprises 10% by weight or more to 60% by weight or less, preferably 15% by weight or more to 50% by weight or less, particularly preferably 20% by weight or more to 45% by weight or less, of compounds of the formulae II and/or III, the medium preferably comprises 45% by weight or more to 80% by weight or less of compounds of the formulae Y-1 to Y-4, the medium preferably comprises 10% by weight or more to 40% by weight or less of compounds of the formula Y-1, the medium preferably comprises 10% by weight or more to 40% by weight or less of compounds of the formula Y-2, the medium preferably comprises 10% by weight or more to 40% by weight or less of compounds of the formula Y-3, the medium preferably comprises 0% by weight or more to 40% by weight or less of compounds of the formula Y-4.

In a preferred embodiment, the liquid-crystal media according to the invention having negative dielectric anisotropy are characterized by optical anisotropy values in the moderate to low region. The birefringence values are preferably in the range from 0.065 or more to 0.140 or less, particularly preferably in the range from 0.090 or more to 0.130 or less and very particularly preferably in the range from 0.095 or more to 0.120 or less.

In this embodiment, the liquid-crystal media according to the invention having negative dielectric anisotropy have relatively high values of the modulus of the dielectric anisotropy ($|\Delta\varepsilon|$), which are preferably in the range from 2.7 or more to 6.0 or less, preferably up to 5.0 or less, preferably from 2.9 or more to 5.0 or less, particularly preferably from 3.0 or more to 4.5 or less and very particularly preferably from 3.5 or more to 4.3 or less.

The liquid-crystal media according to the invention having negative dielectric anisotropy have relatively low values for the threshold voltage ($V_0$) in the range from 1.7 V or more to 2.5 V or less, preferably from 1.8 V or more to 2.4 V or less, particularly preferably from 1.9 V or more to 2.3 V or less and very particularly preferably from 1.95 V or more to 2.1 V or less.

The mixtures according to the invention having negative dielectric anisotropy are suitable for all VA-TFT applications, such as, for example, VAN, MVA, (S)-PVA and ASV. They are furthermore suitable for IPS (in plane switching), FFS (fringe field switching) and PALC applications having negative $\Delta\varepsilon$.

The invention thus also relates to electro-optical displays which are based on the VA or ECB effect and in particular those which are addressed by means of an active-matrix addressing device.

It goes without saying that, through a suitable choice of the components of the mixtures according to the invention, it is also possible for higher clearing points (for example above 100° C.) to be achieved at higher threshold voltages or lower clearing points to be achieved at lower threshold voltages with retention of the other advantageous properties. At viscosities correspondingly increased only slightly, it is likewise possible to obtain mixtures having greater absolute $\Delta\varepsilon$ and thus low thresholds.

The construction of the MLC display according to the invention from polarizers, electrode base plates and surface-treated electrodes corresponds to the usual design for displays of this type. The term usual design is broadly drawn here and also encompasses all derivatives and modifications of the MLC display, in particular including matrix display elements based on poly-Si TFTs or MIM.

The liquid-crystal mixtures which can be used in accordance with the invention are prepared in a manner conventional per se, for example by mixing one or more compounds of the formula I with at least one further mesogenic compound and optionally with one or more additive(s) and/or one or more polymerizable compounds.

In general, the desired amount of the components used in the smaller amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature, such as, for example, UV stabilizers, such as Tinuvin® from Ciba Chemicals, in particular Tinuvin® 770, antioxidants, free-radical scavengers, nanoparticles, etc. For example, 0-15% of pleochroic dyes or chiral dopants can be added. Suitable stabilizers and dopants are mentioned below in Tables C and D.

Polymerizable compounds, so-called "reactive mesogens", are also additionally added to the mixtures according to the invention. Preferred polymerizable compounds are listed in Table E.

For the present invention, "≤" means less than or equal to, preferably less than, and "≥" means greater than or equal to, preferably greater than.

For the present invention,

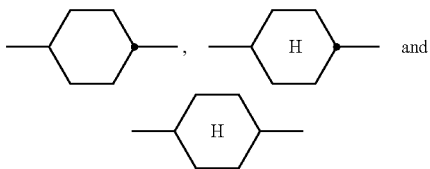

denote trans-1,4-cyclohexylene, and

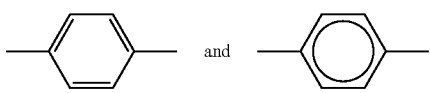

denote 1,4-phenylene.

For the present invention, the term "dielectrically positive compounds" means compounds having a Δε of >1.5, the term "dielectrically neutral compounds" means those where −1.5≤Δε≤1.5 and the term "dielectrically negative compounds" means those where Δε<−1.5. The dielectric anisotropy of the compounds is determined here by dissolving 10% of the compounds in a liquid-crystalline host and determining the capacitance of the resultant mixture in each case in at least one test cell having a cell thickness of 20 μm with homeotropic and with homogeneous surface alignment at 1 kHz. The measurement voltage is typically 0.5 V to 1.0 V, but is always lower than the capacitive threshold of the respective liquid-crystal mixture investigated.

The host mixture used for dielectrically positive and dielectrically neutral compounds is ZLI-4792 and that used for dielectrically negative compounds is ZLI-2857, both from Merck KGaA, Germany. The values for the respective compounds to be investigated are obtained from the change in the dielectric constant of the host mixture after addition of the compound to be investigated and extrapolation to 100% of the compound employed. The compound to be investigated is dissolved in the host mixture in an amount of 10%. If the solubility of the substance is too low for this purpose, the concentration is halved in steps until the investigation can be carried out at the desired temperature.

For the purposes of the present invention, all concentrations are, unless explicitly noted otherwise, indicated in percent by weight and relate to the corresponding mixture or mixture component, unless explicitly indicated otherwise.

All temperature values indicated in the present application, such as, for example, the melting point T(C,N), the smectic (S) to nematic (N) phase transition T(S,N) and the clearing point T(N,I), are indicated in degrees Celsius (° C.) and all temperature differences are correspondingly indicated in differential degrees (° or degrees), unless explicitly indicated otherwise.

For the present invention, the term "threshold voltage" relates to the capacitive threshold ($V_0$), also known as the Freedericks threshold, unless explicitly indicated otherwise.

All physical properties are and have been determined in accordance with "Merck Liquid Crystals, Physical Properties of Liquid Crystals", status November 1997, Merck KGaA, Germany, and apply for a temperature of 20° C., and Δn is determined at 589 nm and Δε at 1 kHz, unless explicitly indicated otherwise in each case.

Unless indicated otherwise, a chiral dopant is not added to the liquid-crystal mixtures used, but the latter are also particularly suitable for applications in which doping of this type is necessary.

The VHR is determined in test cells produced at Merck Japan. The measurement cells have substrates made from soda-lime glass and are designed with polyimide alignment layers (AL-16301 from Japan Synthetic Rubber, Japan) having a layer thickness of 50 nm, which have been rubbed perpendicularly to one another. The layer thickness is a uniform 6.0 μm. The area of the transparent ITO electrodes is 1 cm$^2$.

The VHR is determined at 20° C. (VHR$_{20}$) and after 5 minutes in an oven at 100° C. (VHR$_{100}$) in a commercially available instrument from Autronic Melchers, Germany. The voltage used has a frequency of 60 Hz.

The accuracy of the VHR measurement values depends on the respective value of the VHR. The accuracy decreases with decreasing values. The deviations generally observed in the case of values in the various magnitude ranges are compiled in their order of magnitude in the following table.

| VHR range VHR values | | Deviation (relative) $\Delta_G$VHR/VHR/% |
|---|---|---|
| from | to | approx. |
| 99.6% | 100% | +/−0.1 |
| 99.0% | 99.6% | +/−0.2 |
| 98% | 99% | +/−0.3 |
| 95% | 98% | +/−0.5 |
| 90% | 95% | +/−1 |
| 80% | 90% | +/−2 |
| 60% | 80% | +/−4 |
| 40% | 60% | +/−8 |
| 20% | 40% | +/−10 |
| 10% | 20% | +/−20 |

The stability to UV irradiation is investigated in a "Suntest CPS", a commercial instrument from Heraeus, Germany. The sealed test cells are irradiated for 2.0 hours without additional heating. The irradiation power in the wavelength range from 300 nm to 800 nm is 765 W/m$^2$ V.

A further characteristic quantity which, besides the VHR, can characterize the conductivity of the liquid-crystal mixtures is the ion density. High values of the ion density often result in the occurrence of display faults, such as image sticking and flickering. The ion density is preferably determined in test cells produced at Merck Japan Ltd. The test cells have substrates made from soda-lime glass and are designed with polyimide alignment layers (AL-3046 from Japan Synthetic Rubber, Japan) having a polyimide layer thickness of 40 nm. The layer thickness of the liquid-crystal mixture is a uniform 5.8 μm. The area of the circular, transparent ITO electrodes, which are additionally fitted with a guard ring, is 1 cm$^2$. The accuracy of the measurement method is about ±15%. The cells are dried overnight in an oven at 120° C. before filling with the relevant liquid-crystal mixture.

The ion density is measured using a commercially available instrument from TOYO, Japan. The measurement method is essentially a measurement method which is analogous to cyclic voltammetry, as described in M. Inoue, "Recent Measurement of Liquid Crystal Material Characteristics", Proceedings IDW 2006, LCT-7-1,647. In this method, an applied direct voltage is varied between a positive and negative maximum value in accordance with a pre-specified triangular profile. A complete run through the profile thus forms one measurement cycle. If the applied voltage is sufficiently large that the ions in the field are able to move to the respective electrode, an ion current forms due to discharge of the ions. The amount of charge transferred here is typically in the range from a few pC to a few nC. This makes highly sensitive detection necessary, which is ensured by the above-mentioned instrument. The results are depicted in a current/voltage curve. The ion current here is evident from the occurrence of a peak at voltages which are smaller than the threshold voltage of the liquid-crystal mixture. Integration of the peak area gives the value for the ion density of the mixture investigated. Four test cells are measured per mixture. The repetition frequency of the triangular voltage is 0.033 Hz, the measurement temperature is 60° C., the maximum voltage is ±3 V to ±10 V, depending on the magnitude of the dielectric anisotropy of the relevant mixture.

The rotational viscosity is determined using the rotating permanent magnet method and the flow viscosity in a modified Ubbelohde viscometer. For liquid-crystal mixtures ZLI-2293, ZLI-4792 and MLC-6608, all products from Merck KGaA, Darmstadt, Germany, the rotational viscosity values determined at 20° C. are 161 mPa·s, 133 mPa·s and 186 mPa·s respectively, and the flow viscosity values (v) are 21 mm$^2$·s$^{-1}$, 14 mm$^2$·s$^{-1}$ and 27 mm$^2$·s$^{-1}$ respectively.

The following symbols are used, unless explicitly indicated otherwise:

$V_0$ threshold voltage, capacitive [V] at 20° C.,
$n_e$ extraordinary refractive index measured at 20° C. and 589 nm,
$n_o$ ordinary refractive index measured at 20° C. and 589 nm,
Δn optical anisotropy measured at 20° C. and 589 nm,
$\varepsilon_\perp$ dielectric susceptibility perpendicular to the director at 20° C. and 1 kHz,
$\varepsilon_\parallel$ dielectric susceptibility parallel to the director at 20° C. and 1 kHz,
Δε dielectric anisotropy at 20° C. and 1 kHz,
cl.p. or T(N,I) clearing point [° C.],
v flow viscosity measured at 20° C. [mm$^2$·s$^{-1}$],
$\gamma_1$ rotational viscosity measured at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN], and
LTS low-temperature stability of the phase, determined in test cells,
VHR voltage holding ratio.

The following examples explain the present invention without limiting it. However, they show the person skilled in the art preferred mixture concepts with compounds preferably to be employed and the respective concentrations thereof and combinations thereof with one another. In addition, the examples illustrate the properties and property combinations that are accessible.

In the present application and in the examples below, the structures of the liquid-crystal compounds are indicated by means of acronyms, the transformation into chemical formulae taking place in accordance with Table A. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF.F | $C_nH_{2n+1}$ | F | F | H |
| nF.F.F | $C_nH_{2n+1}$ | F | F | F |
| nOCF$_3$ | $C_nH_{2n+1}$ | OCF$_3$ | H | H |
| nOCF$_3$.F | $C_nH_{2n+1}$ | OCF$_3$ | F | H |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |

Preferred mixture components are shown in Tables A and B.

TABLE A

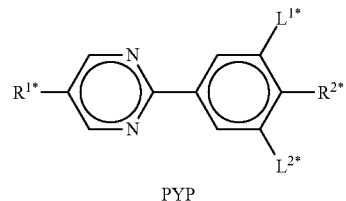

PYP

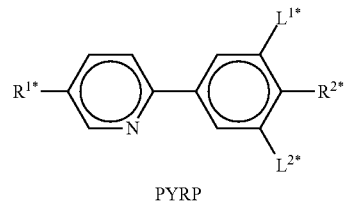

PYRP

TABLE A-continued
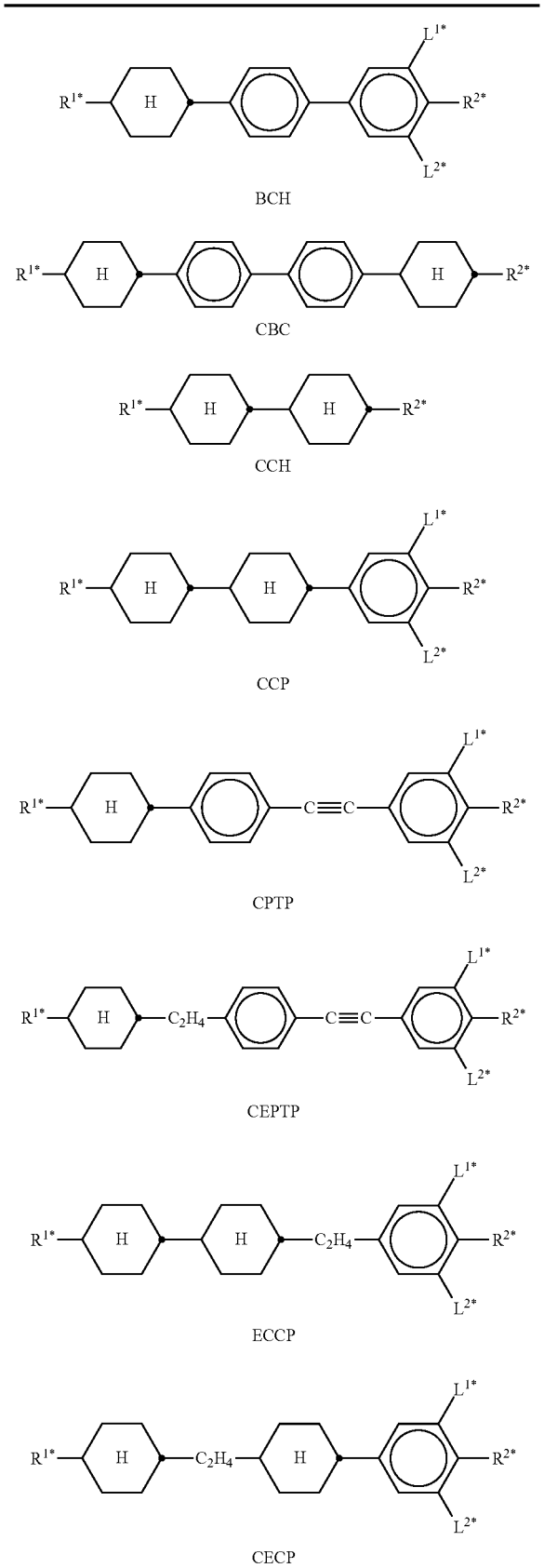
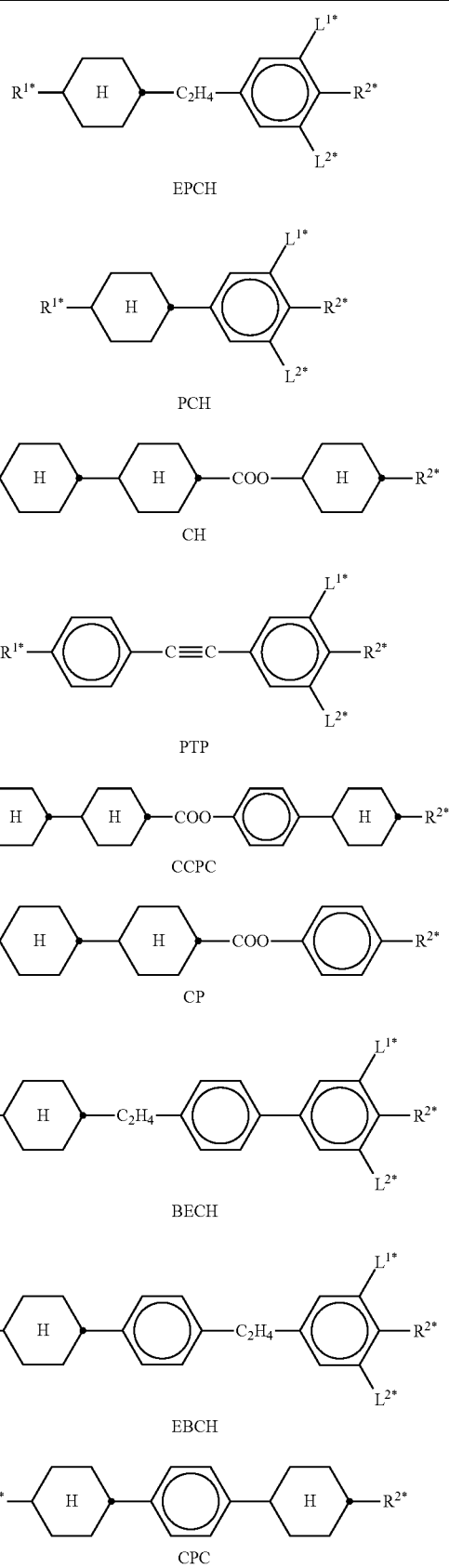

TABLE A-continued
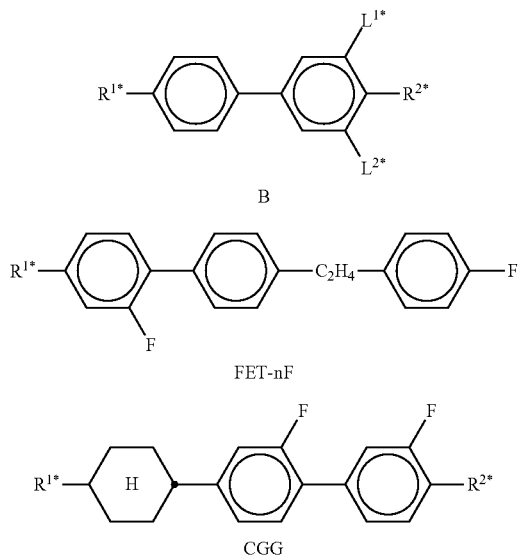
B
FET-nF
CGG
TABLE A-continued
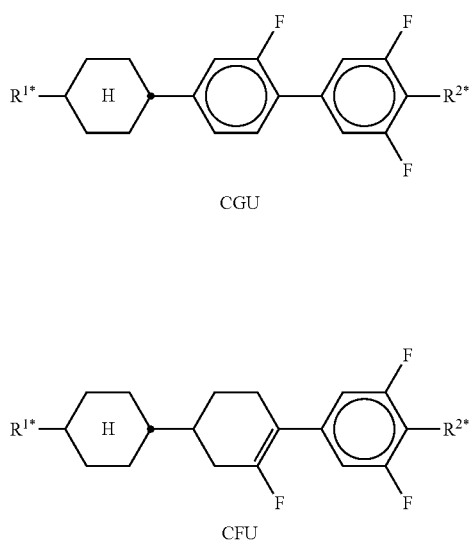
CGU
CFU
TABLE B
(n, m, l = 1-15; (O)$C_nH_{2n+1}$ denotes $C_nH_{2n+1}$ or $OC_nH_{2n+1}$)
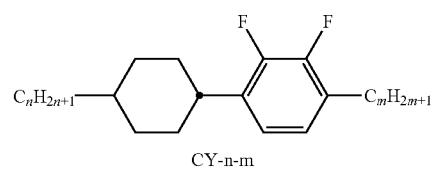
CY-n-m
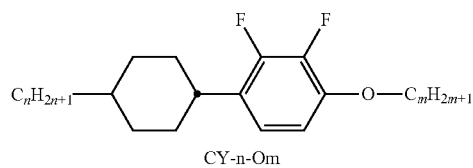
CY-n-Om
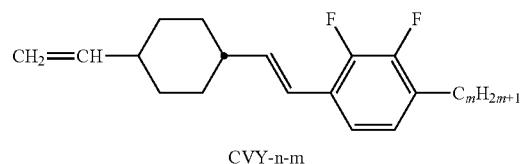
CVY-n-m
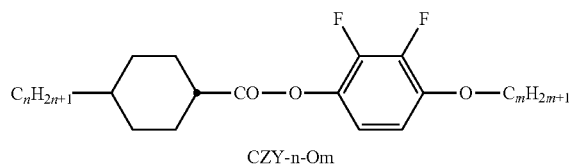
CZY-n-Om
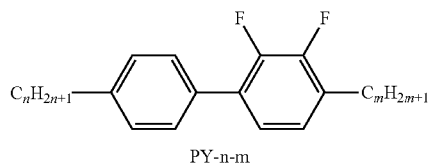
PY-n-m TABLE B-continued
(n, m, l = 1-15; (O)$C_nH_{2n+1}$ denotes $C_nH_{2n+1}$ or $OC_nH_{2n+1}$)
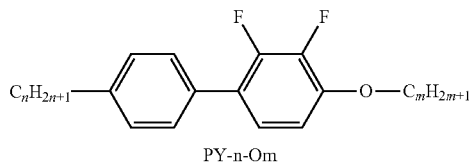
PY-n-Om
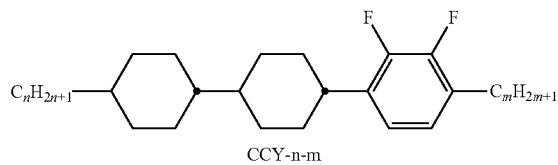
CCY-n-m
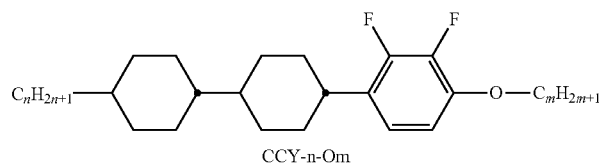
CCY-n-Om
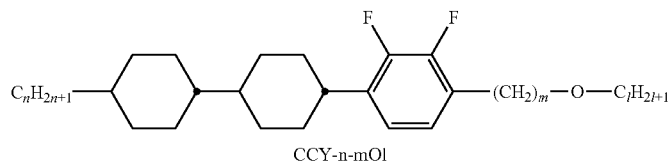
CCY-n-mOl
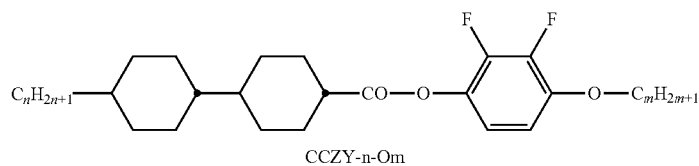
CCZY-n-Om
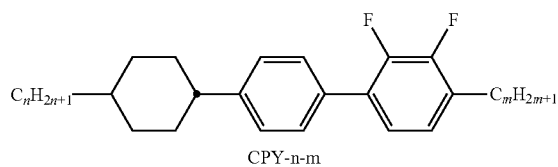
CPY-n-m
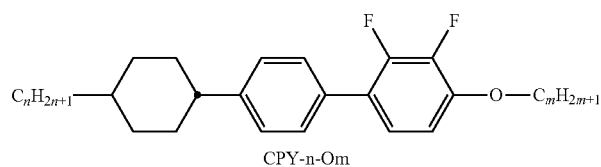
CPY-n-Om
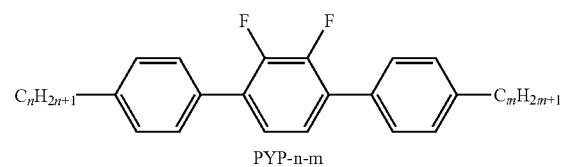
PYP-n-m
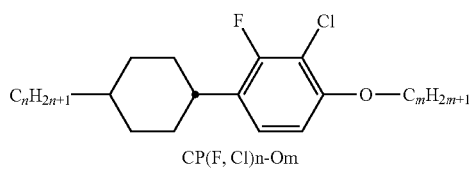
CP(F, Cl)n-Om TABLE B-continued
(n, m, l = 1-15; (O)$C_nH_{2n+1}$ denotes $C_nH_{2n+1}$ or $OC_nH_{2n+1}$)
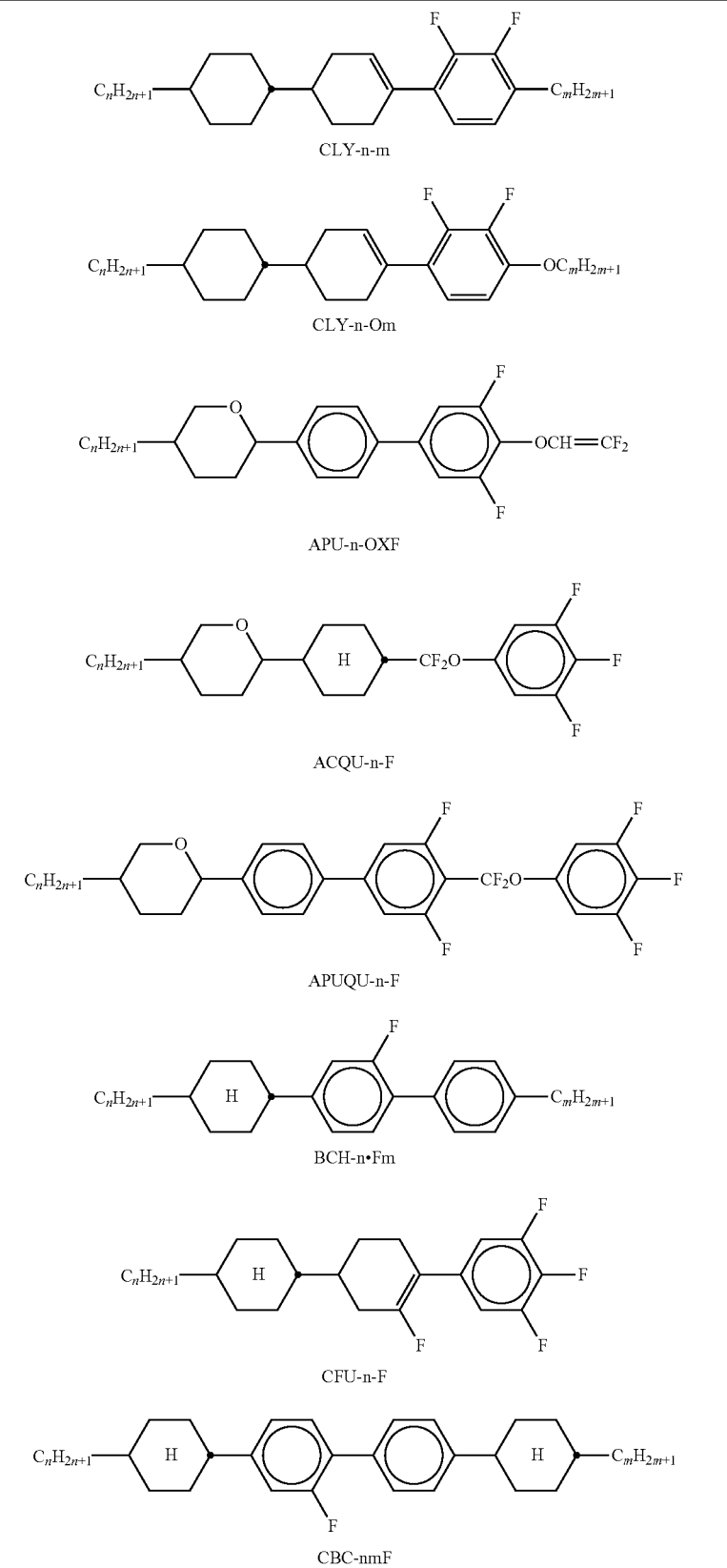

TABLE B-continued
(n, m, l = 1-15; (O)C$_n$H$_{2n+1}$ denotes C$_n$H$_{2n+1}$ or OC$_n$H$_{2n+1}$)
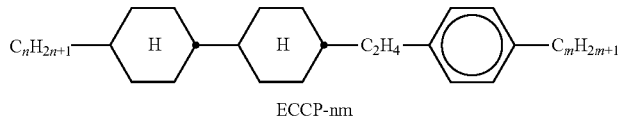
ECCP-nm
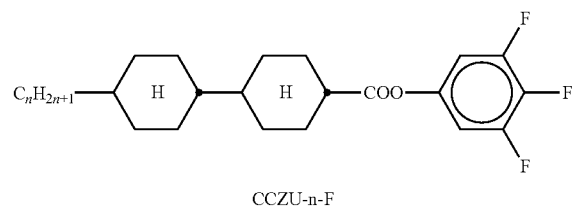
CCZU-n-F
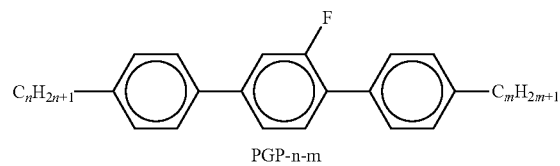
PGP-n-m
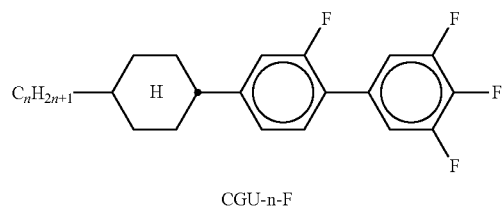
CGU-n-F
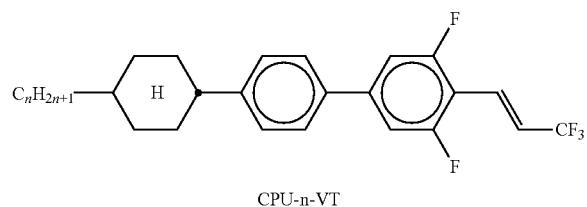
CPU-n-VT
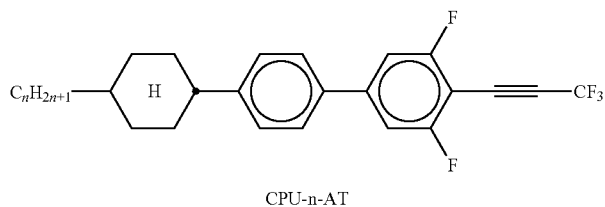
CPU-n-AT
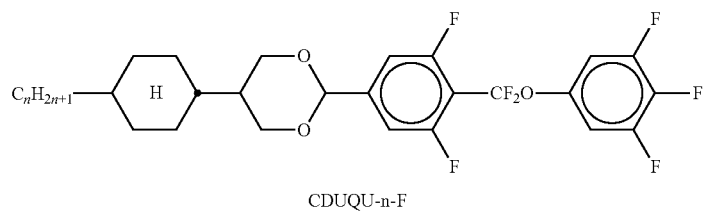
CDUQU-n-F TABLE B-continued
(n, m, l = 1-15; (O)$C_nH_{2n+1}$ denotes $C_nH_{2n+1}$ or $OC_nH_{2n+1}$)
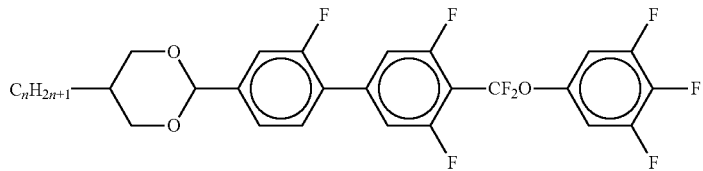
DGUQU-n-F
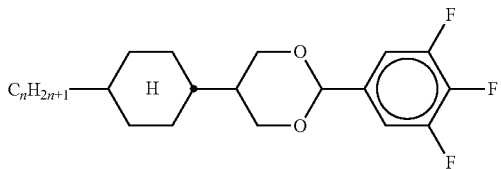
CDU-n-F
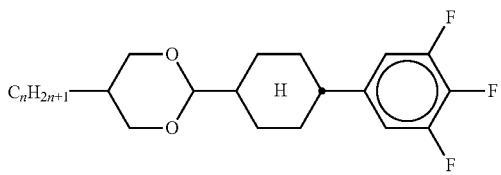
DCU-n-F
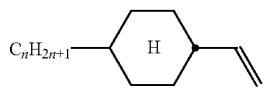
C-n-V
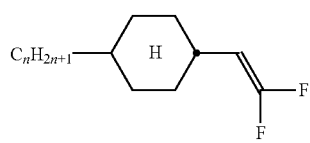
C-n-XF
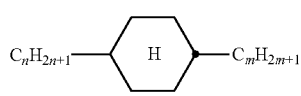
C-n-m
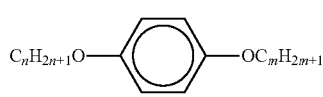
Y-nO—Om
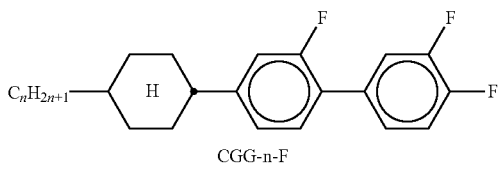
CGG-n-F
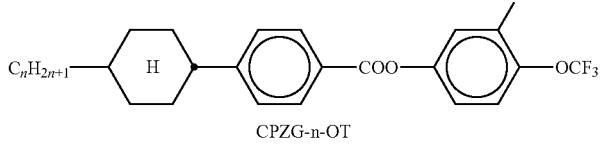
CPZG-n-OT TABLE B-continued
(n, m, l = 1-15; (O)$C_nH_{2n+1}$ denotes $C_nH_{2n+1}$ or $OC_nH_{2n+1}$)
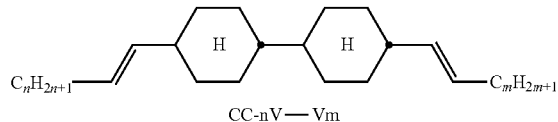
CC-nV—Vm
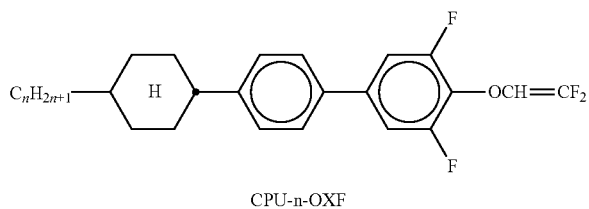
CPU-n-OXF
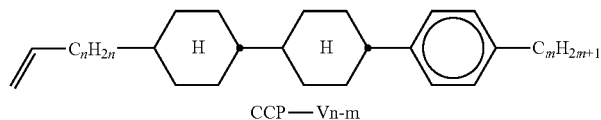
CCP—Vn-m
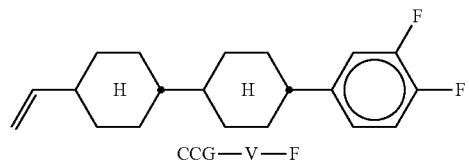
CCG—V—F
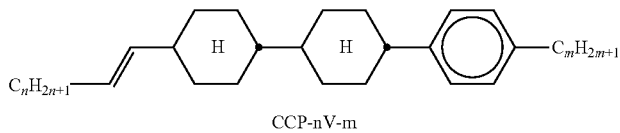
CCP-nV-m
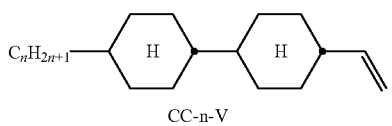
CC-n-V
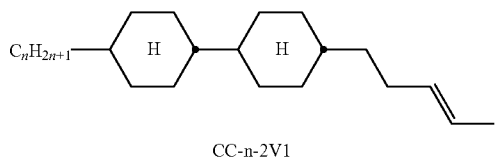
CC-n-2V1
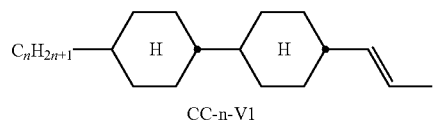
CC-n-V1
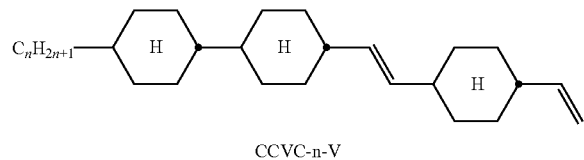
CCVC-n-V TABLE B-continued
(n, m, l = 1-15; (O)$C_nH_{2n+1}$ denotes $C_nH_{2n+1}$ or $OC_nH_{2n+1}$)
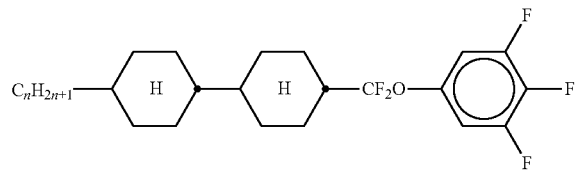
CCQU-n-F
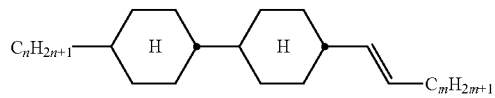
CC-n-Vm
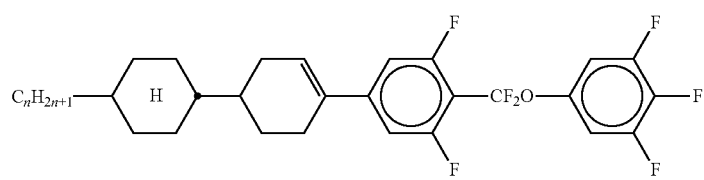
CLUQU-n-F
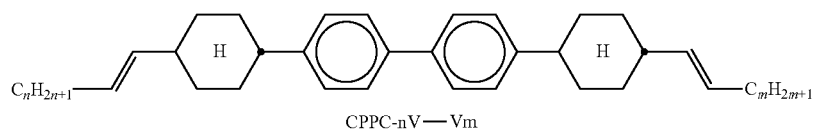
CPPC-nV—Vm
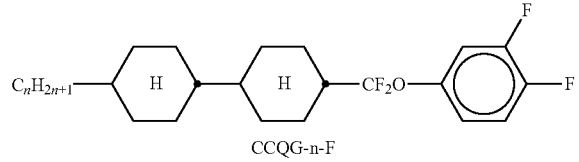
CCQG-n-F
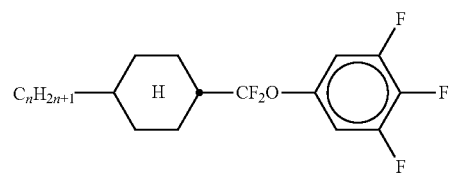
CQU-n-F
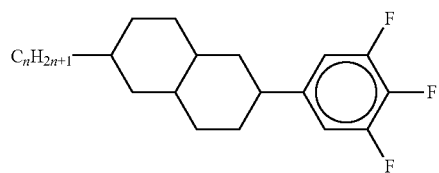
Dec-U-n-F
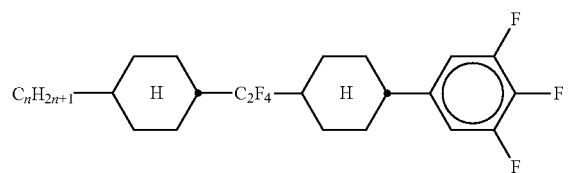
CWCU-n-F TABLE B-continued
(n, m, l = 1-15; (O)$C_nH_{2n+1}$ denotes $C_nH_{2n+1}$ or $OC_nH_{2n+1}$)
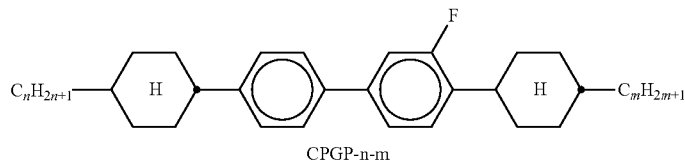
CPGP-n-m
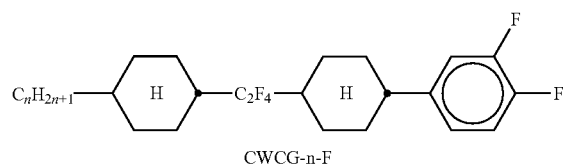
CWCG-n-F
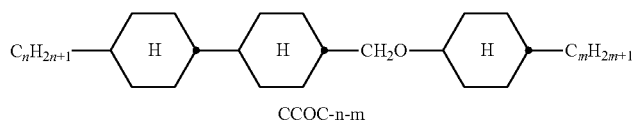
CCOC-n-m
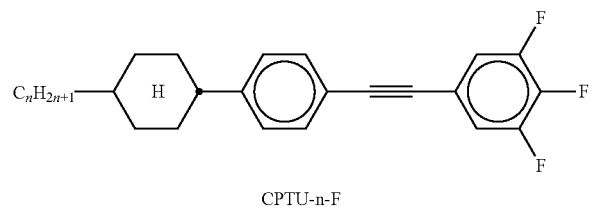
CPTU-n-F
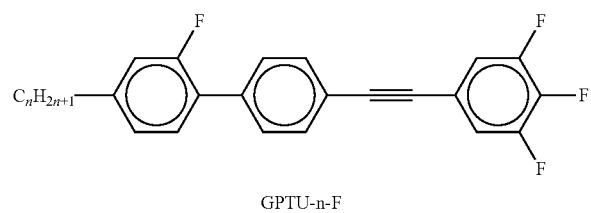
GPTU-n-F
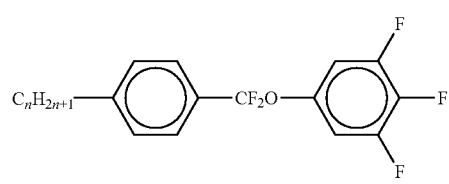
PQU-n-F
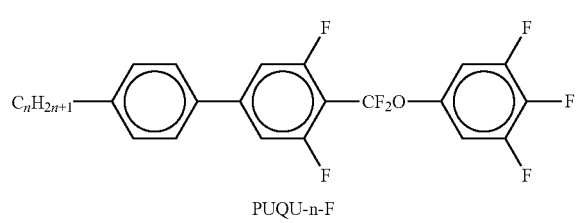
PUQU-n-F
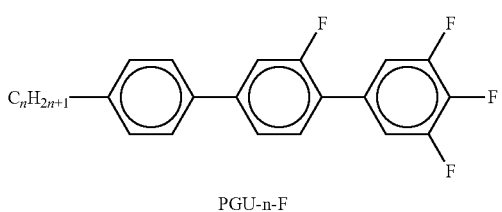
PGU-n-F TABLE B-continued
(n, m, l = 1-15; (O)$C_nH_{2n+1}$ denotes $C_nH_{2n+1}$ or $OC_nH_{2n+1}$)
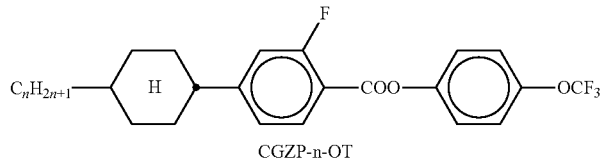
CGZP-n-OT
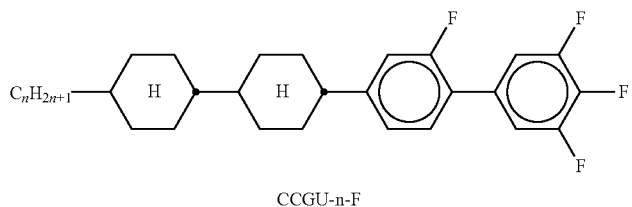
CCGU-n-F
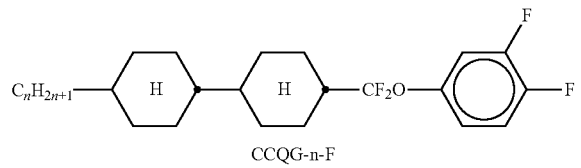
CCQG-n-F
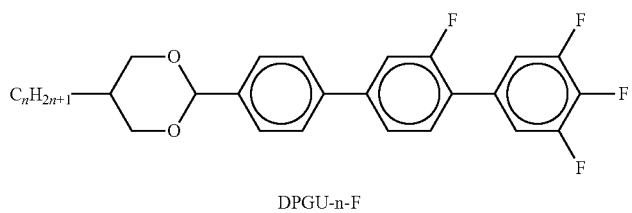
DPGU-n-F
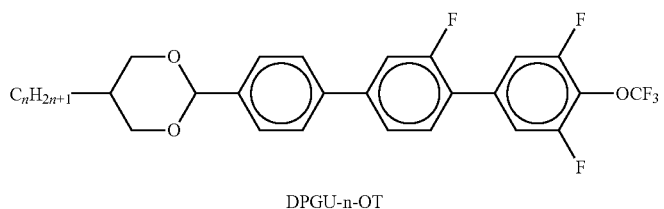
DPGU-n-OT
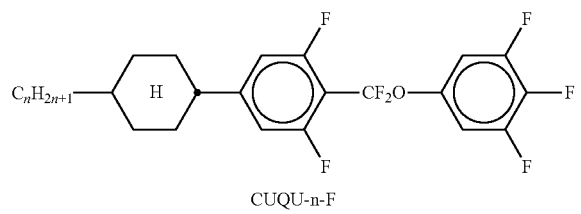
CUQU-n-F
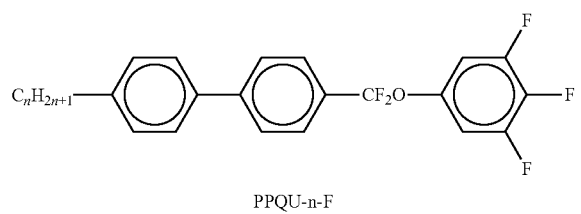
PPQU-n-F TABLE B-continued
(n, m, l = 1-15; (O)$C_nH_{2n+1}$ denotes $C_nH_{2n+1}$ or $OC_nH_{2n+1}$)
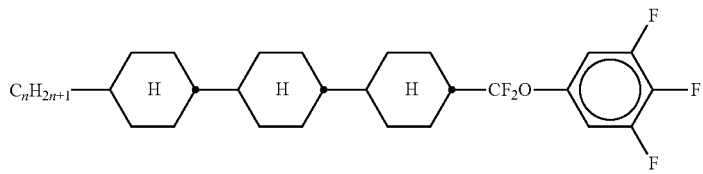
CCCQU-n-F
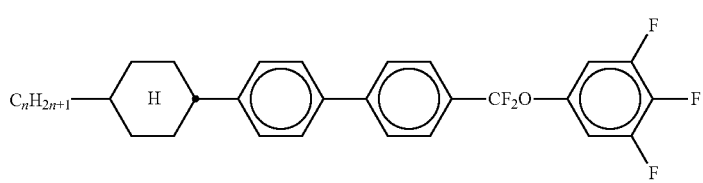
CPPQU-n-F
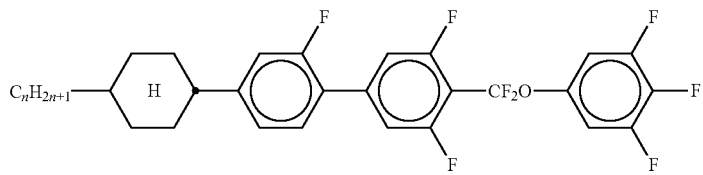
CGUQU-n-F
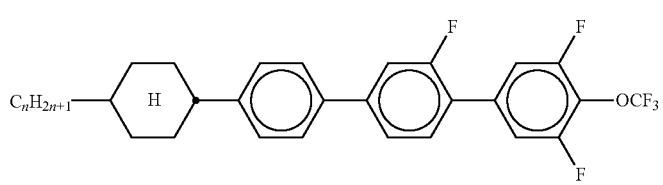
CPGU-n-OT
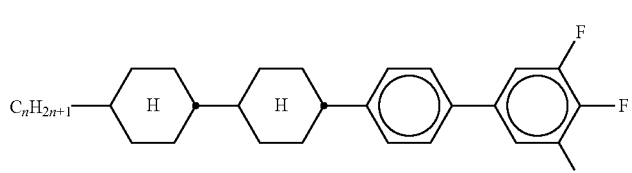
CCPU-n-F
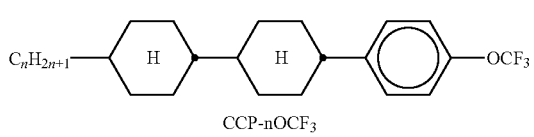
CCP-nOCF$_3$
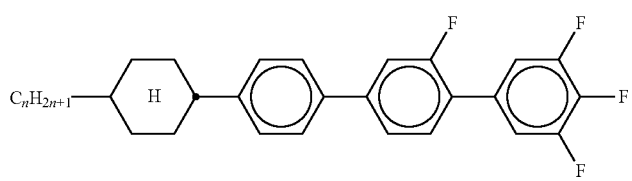
CPGU-n-F TABLE B-continued
(n, m, l = 1-15; $(O)C_nH_{2n+1}$ denotes $C_nH_{2n+1}$ or $OC_nH_{2n+1}$)
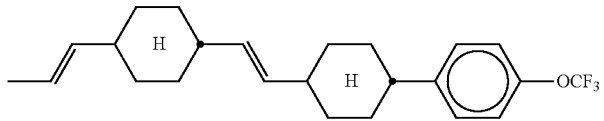
CVCP-1V-OT
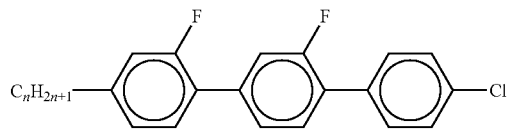
GGP-n-Cl
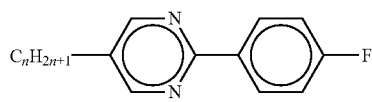
PYP-nF
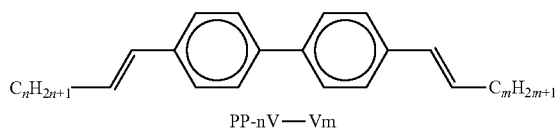
PP-nV—Vm
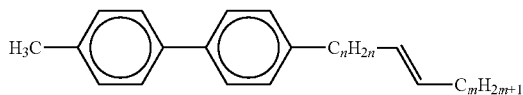
PP-1-nVm
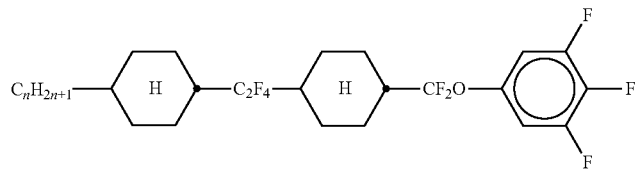
CWCQU-n-F
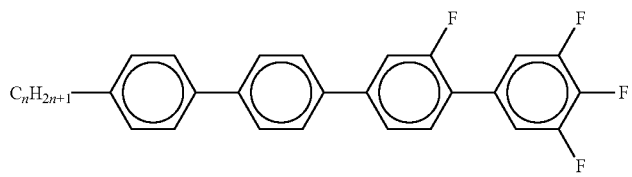
PPGU-n-F
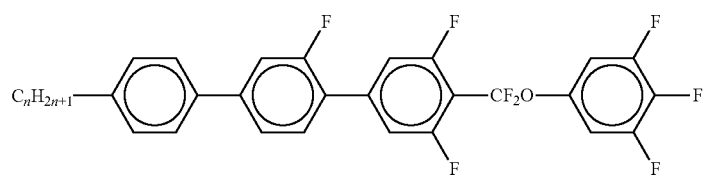
PGUQU-n-F TABLE B-continued
(n, m, l = 1-15; (O)$C_nH_{2n+1}$ denotes $C_nH_{2n+1}$ or $OC_nH_{2n+1}$)
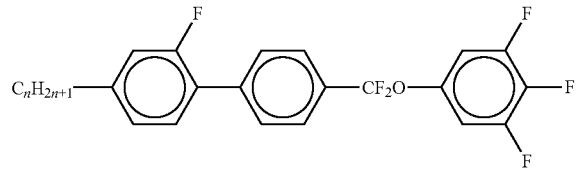
GPQU-n-F
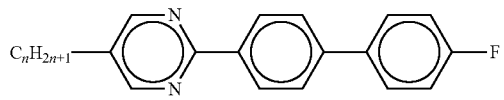
MPP-n-F
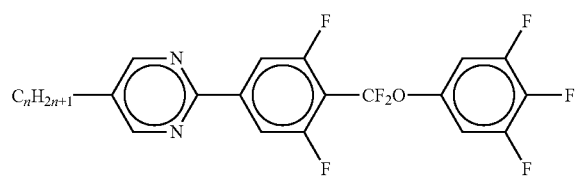
MUQU-n-F
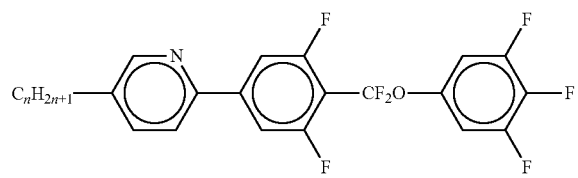
NUQU-n-F
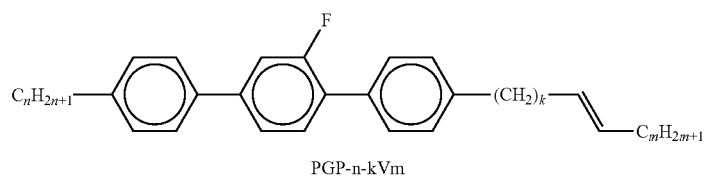
PGP-n-kVm
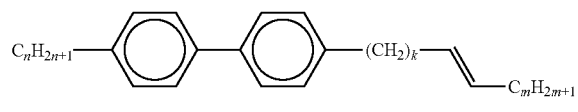
PP-n-kVm
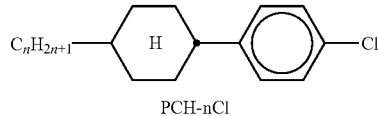
PCH-nCl
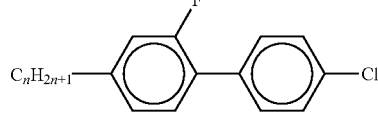
GP-n-Cl TABLE B-continued (n, m, l = 1-15; (O)C$_n$H$_{2n+1}$ denotes C$_n$H$_{2n+1}$ or OC$_n$H$_{2n+1}$)

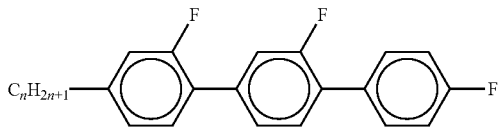

GGP-n-F

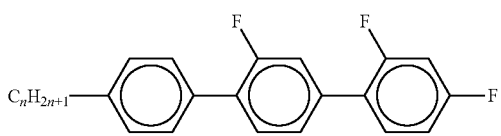

PGIGI-n-F

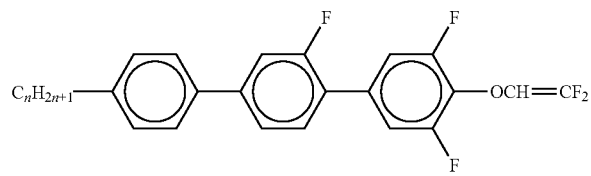

PGU-n-OXF

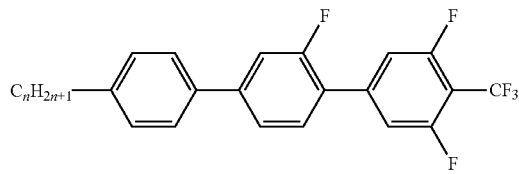

PGU-n-T

Particular preference is given to liquid-crystalline mixtures which, besides the compounds of the formula I, comprise at least one, two, three, four or more compounds from Table B.

TABLE C

Table C indicates possible dopants which are generally added to the mixtures according to the invention. The mixtures preferably comprise 0-10% by weight, in particular 0.01-5% by weight and particularly preferably 0.01-3% by weight, of dopants.

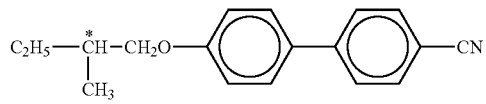

C 15

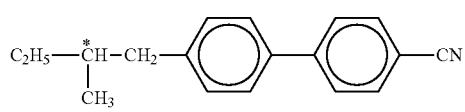

CB 15

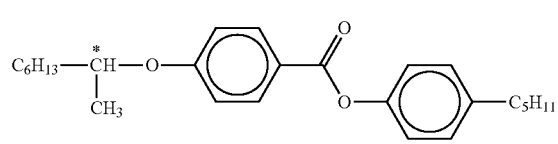

CM 21

TABLE C-continued
Table C indicates possible dopants which are generally added to the mixtures according to the invention. The mixtures preferably comprise 0-10% by weight, in particular 0.01-5% by weight and particularly preferably 0.01-3% by weight, of dopants.
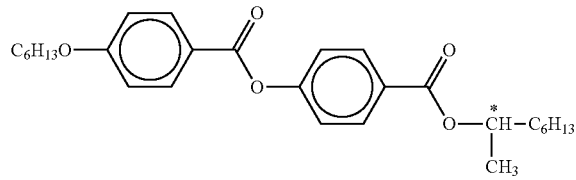
R/S-811
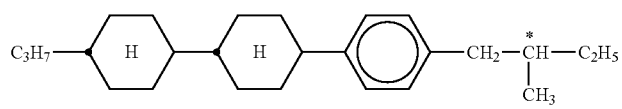
CM 44
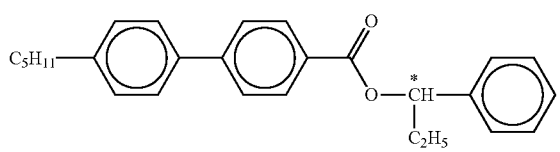
CM 45
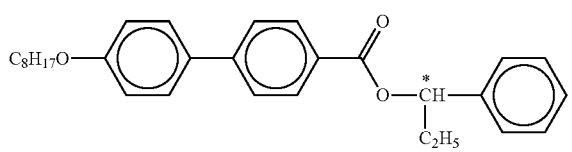
CM 47
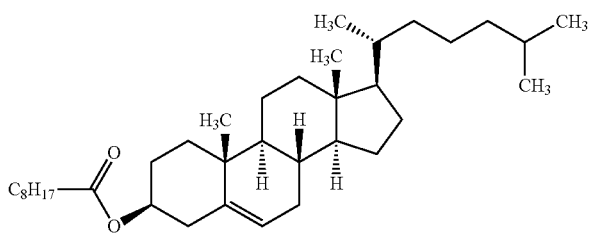
CN
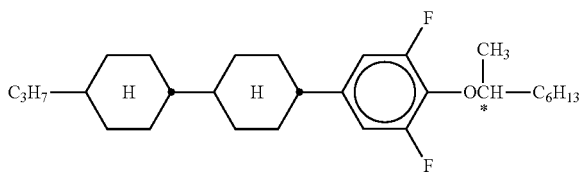
R/S-2011
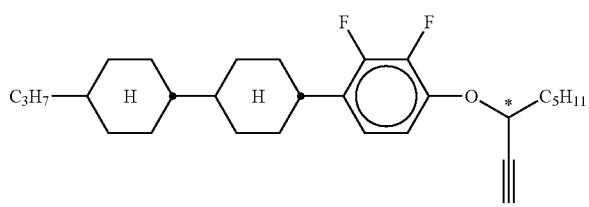
R/S-3011
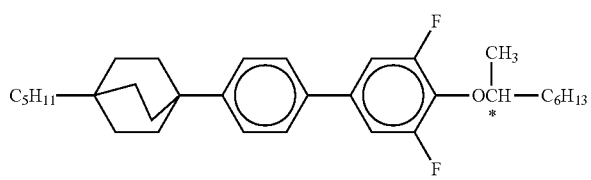
R/S-4011

TABLE C-continued

Table C indicates possible dopants which are generally added to the mixtures according to the invention. The mixtures preferably comprise 0-10% by weight, in particular 0.01-5% by weight and particularly preferably 0.01-3% by weight, of dopants.

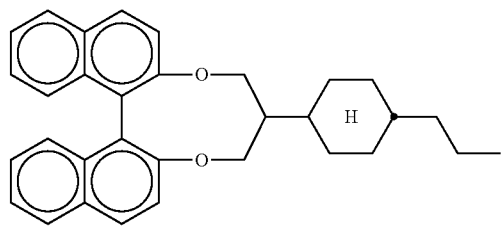

R/S-5011

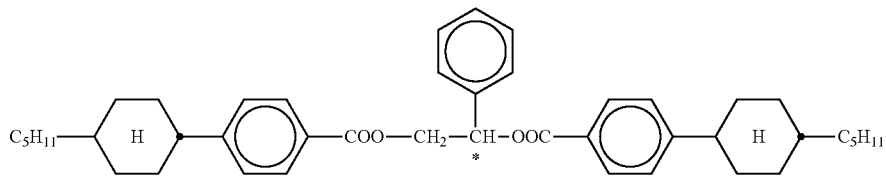

R/S-1011

TABLE D

Stabilizers which can be added, for example, to the mixtures according to the invention in amounts of 0-10% by weight are indicated below.

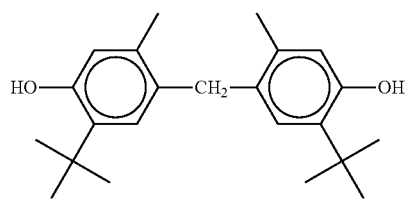

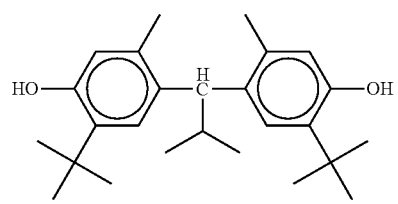

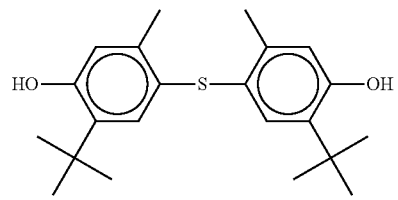

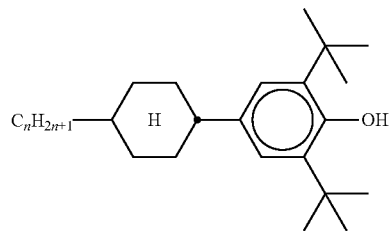

n = 1, 2, 3, 4, 5, 6 or 7

TABLE D-continued
Stabilizers which can be added, for example, to the mixtures according to the invention in amounts of 0-10% by weight are indicated below.
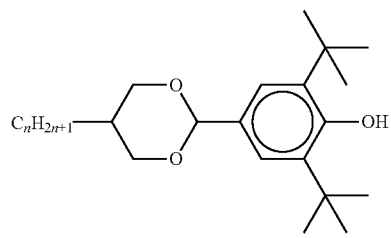
n = 1, 2, 3, 4, 5, 6 or 7
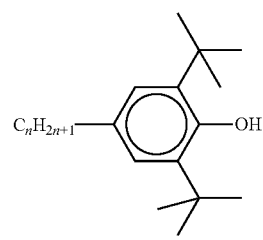
n = 1, 2, 3, 4, 5, 6 or 7
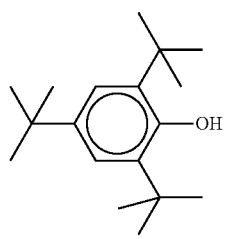
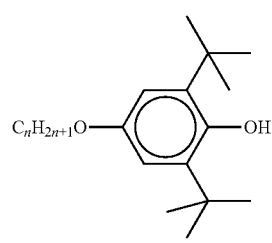
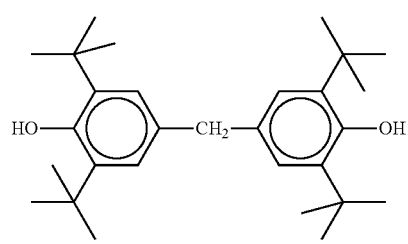
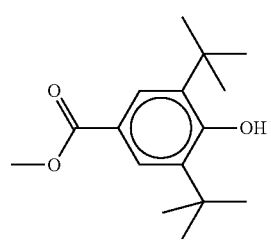

TABLE D-continued
Stabilizers which can be added, for example, to the mixtures according to the invention in amounts of 0-10% by weight are indicated below.
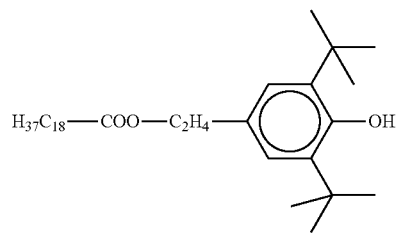
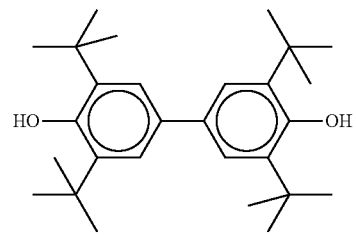
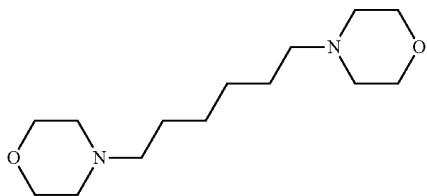 [SMILES: C(CCCN1CCOCC1)CCN1CCOCC1]
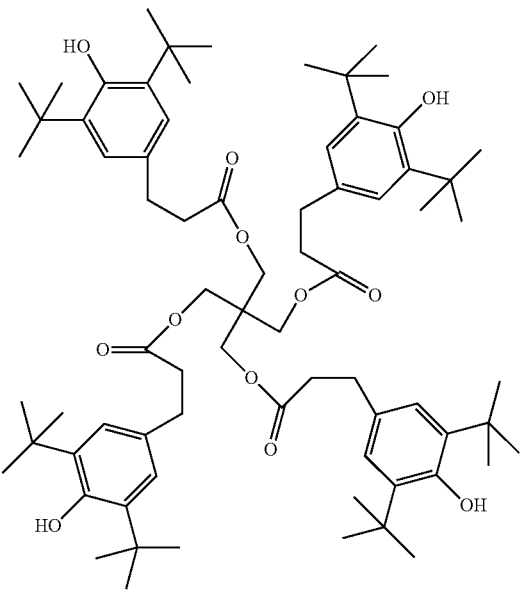 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
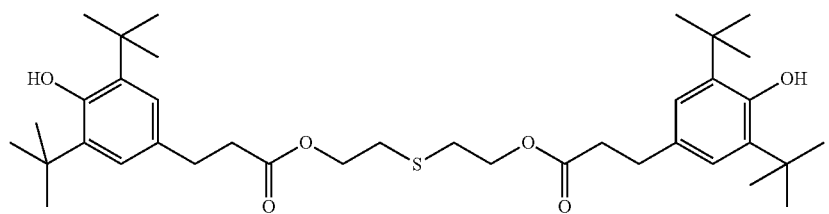 [SMILES: CC(C)(C)c1cc(CCC(=O)OCCSCCOC(=O)CCc2cc(C(C)(C)C)c(O)c(C(C)(C)C)c2)cc(C(C)(C)C)c1O]

TABLE D-continued
Stabilizers which can be added, for example, to the mixtures according to the invention in amounts of 0-10% by weight are indicated below.
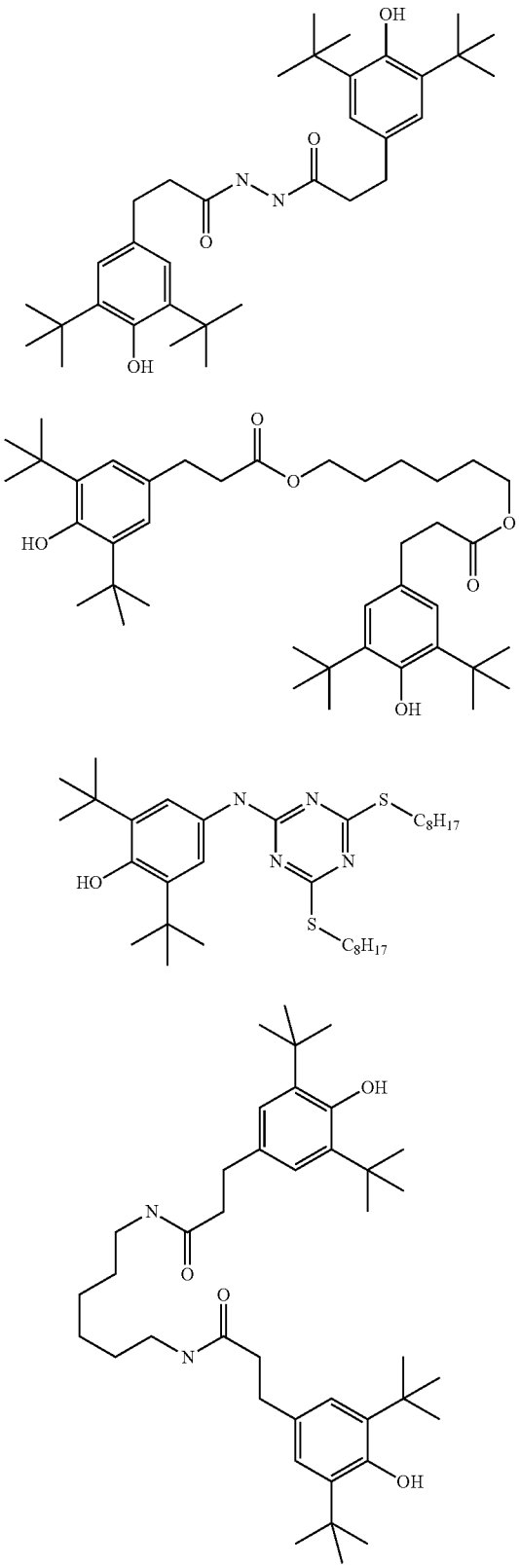

TABLE D-continued
Stabilizers which can be added, for example, to the mixtures according to the invention in amounts of 0-10% by weight are indicated below.
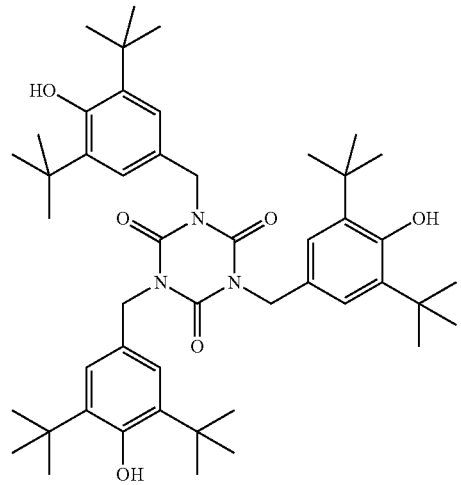 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
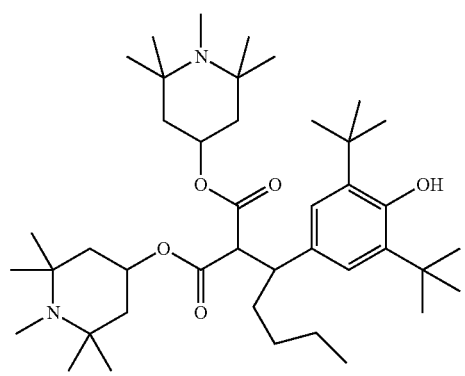 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]
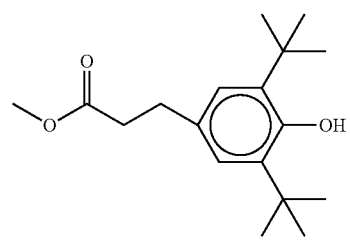
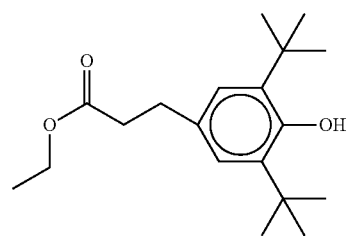

TABLE D-continued
Stabilizers which can be added, for example, to the mixtures according to the invention in amounts of 0-10% by weight are indicated below.
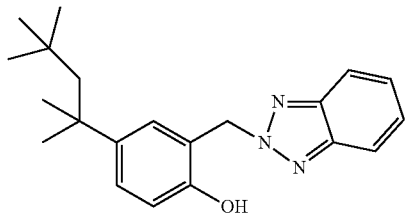 [SMILES: CC(C)(C)CC(C)(C)c1ccc(O)c(Cn2nc3ccccc3n2)c1]
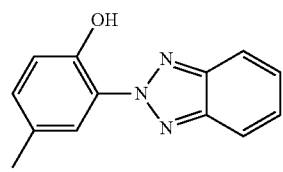 [SMILES: Cc1ccc(O)c(-n2nc3ccccc3n2)c1]
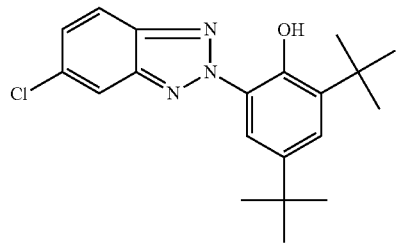 [SMILES: CC(C)(C)c1cc(-n2nc3ccc(Cl)cc3n2)c(O)c(C(C)(C)C)c1]
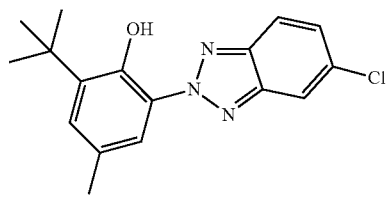 [SMILES: Cc1cc(-n2nc3ccc(Cl)cc3n2)c(O)c(C(C)(C)C)c1]
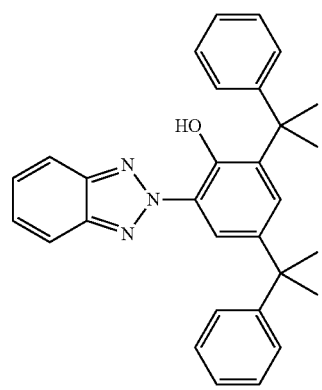 [SMILES: CC(C)(c1ccccc1)c1cc(-n2nc3ccccc3n2)c(O)c(C(C)(C)c2ccccc2)c1]
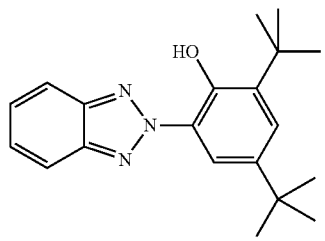 [SMILES: CC(C)(C)c1cc(-n2nc3ccccc3n2)c(O)c(C(C)(C)C)c1]

TABLE D-continued
Stabilizers which can be added, for example, to the mixtures according to the invention in amounts of 0-10% by weight are indicated below.
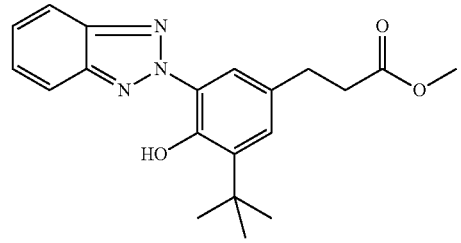 [SMILES: COC(=O)CCc1cc(-n2nc3ccccc3n2)c(O)c(C(C)(C)C)c1]
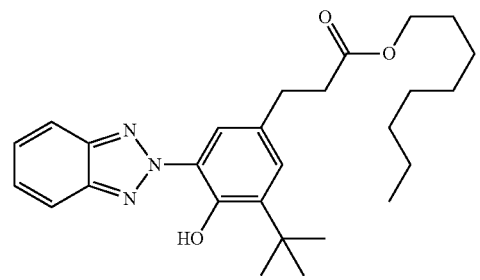 [SMILES: CCCCCCCCOC(=O)CCc1cc(-n2nc3ccccc3n2)c(O)c(C(C)(C)C)c1]
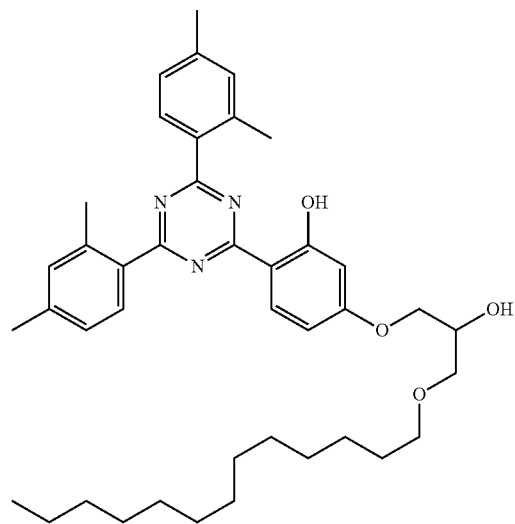 [SMILES: CCCCCCCCCCCCCOCC(O)COc1ccc(-c2nc(-c3ccc(C)cc3C)nc(-c3ccc(C)cc3C)n2)c(O)c1]

TABLE D-continued
Stabilizers which can be added, for example, to the mixtures according to the invention in amounts of 0-10% by weight are indicated below.
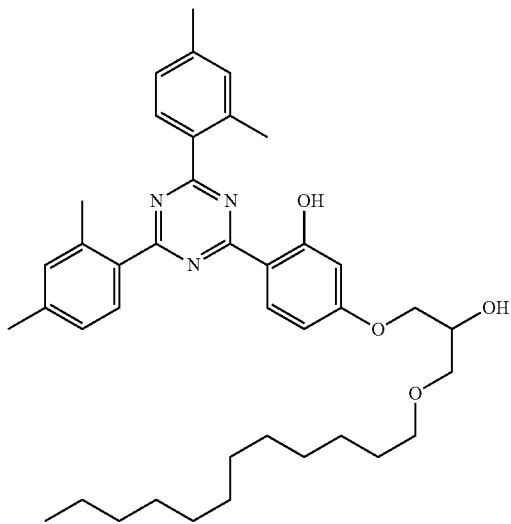 [SMILES: CCCCCCCCCCCCOCC(O)COc1ccc(-c2nc(-c3ccc(C)cc3C)nc(-c3ccc(C)cc3C)n2)c(O)c1]
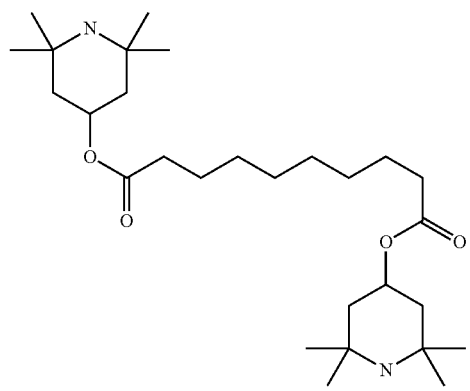
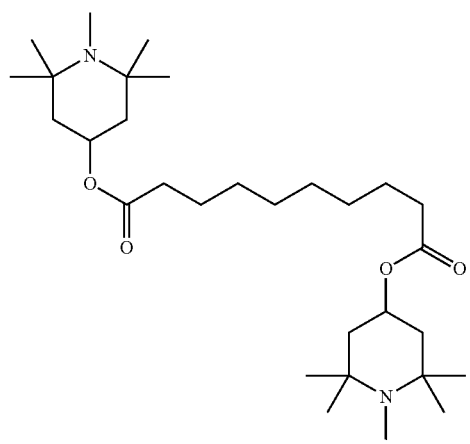

TABLE D-continued

Stabilizers which can be added, for example, to the mixtures according to the invention in amounts of 0-10% by weight are indicated below.

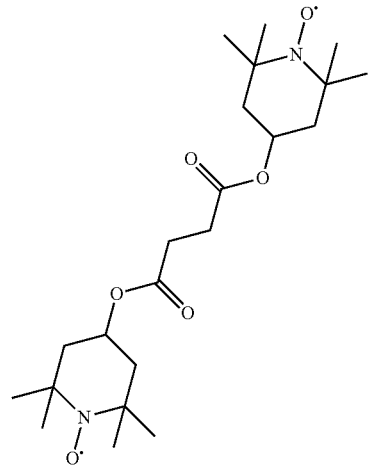

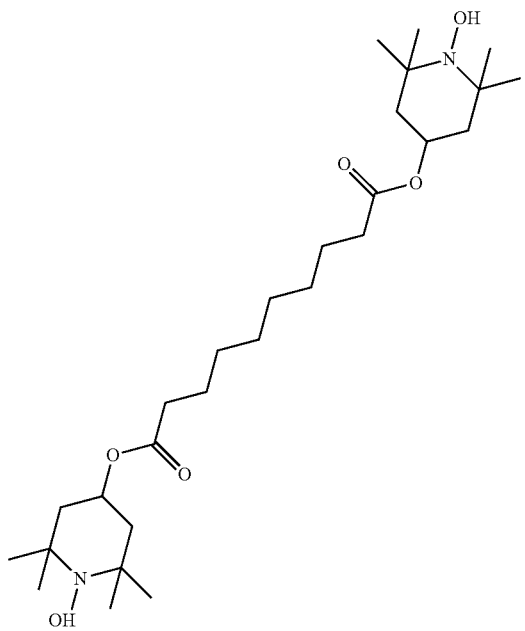

TABLE E

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

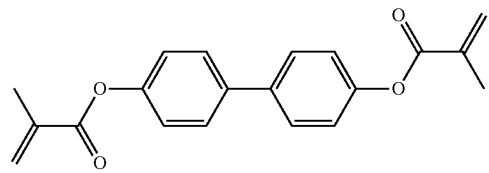 [SMILES: C=C(C)C(=O)Oc1ccc(-c2ccc(OC(=O)C(=C)C)cc2)cc1]

RM-1

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

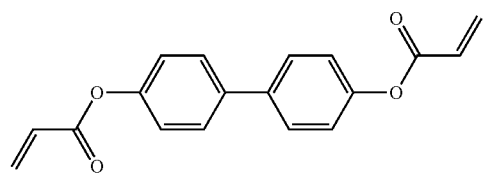

RM-2

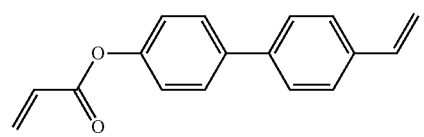 [SMILES: C=CC(=O)Oc1ccc(-c2ccc(C=C)cc2)cc1]

RM-3

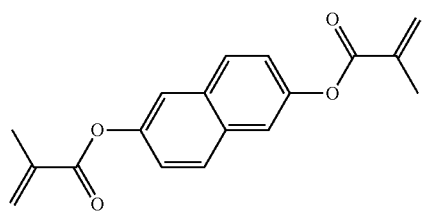 [SMILES: C=C(C)C(=O)Oc1ccc2cc(OC(=O)C(=C)C)ccc2c1]

RM-4

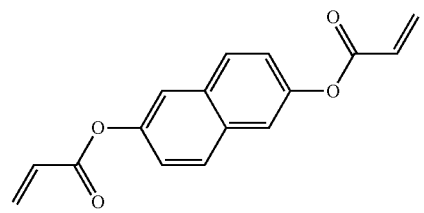 [SMILES: C=CC(=O)Oc1ccc2cc(OC(=O)C=C)ccc2c1]

RM-5

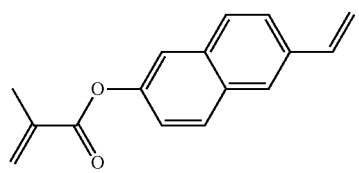 [SMILES: C=Cc1ccc2cc(OC(=O)C(=C)C)ccc2c1]

RM-6

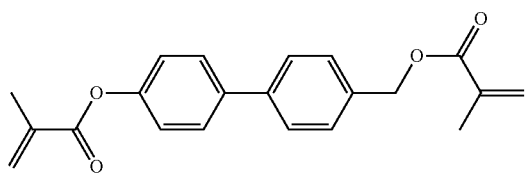 [SMILES: C=C(C)C(=O)OCc1ccc(-c2ccc(OC(=O)C(=C)C)cc2)cc1]

RM-7

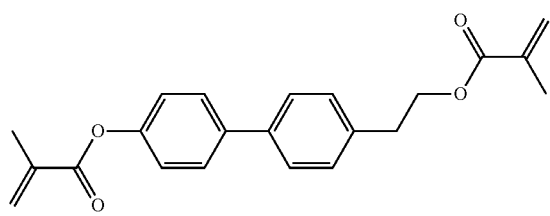 [SMILES: C=C(C)C(=O)OCCc1ccc(-c2ccc(OC(=O)C(=C)C)cc2)cc1]

RM-8

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

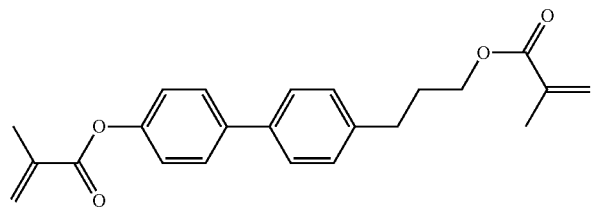 [SMILES: C=C(C)C(=O)OCCCc1ccc(-c2ccc(OC(=O)C(=C)C)cc2)cc1]

RM-9

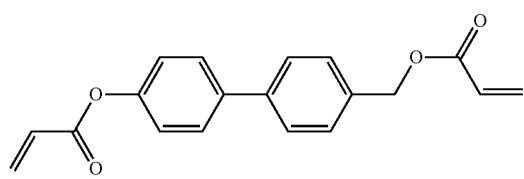 [SMILES: C=CC(=O)OCc1ccc(-c2ccc(OC(=O)C=C)cc2)cc1]

RM-10

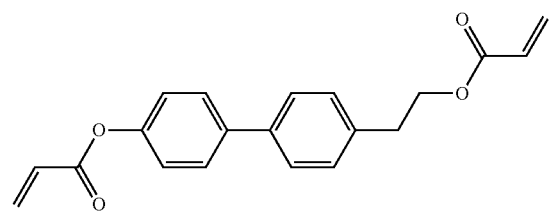 [SMILES: C=CC(=O)OCCc1ccc(-c2ccc(OC(=O)C=C)cc2)cc1]

RM-11

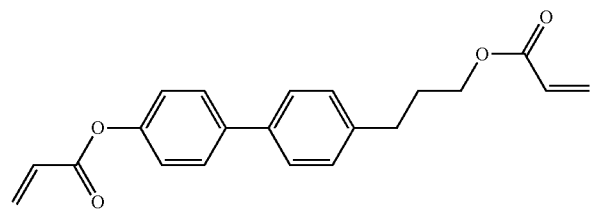 [SMILES: C=CC(=O)OCCCc1ccc(-c2ccc(OC(=O)C=C)cc2)cc1]

RM-12

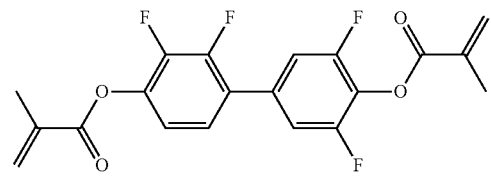 [SMILES: C=C(C)C(=O)Oc1ccc(-c2cc(F)c(OC(=O)C(=C)C)c(F)c2)c(F)c1F]

RM-13

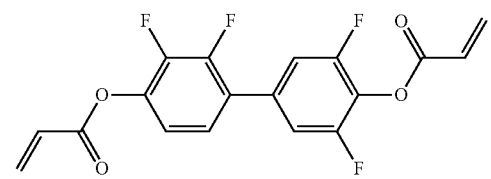 [SMILES: C=CC(=O)Oc1ccc(-c2cc(F)c(OC(=O)C=C)c(F)c2)c(F)c1F]

RM-14

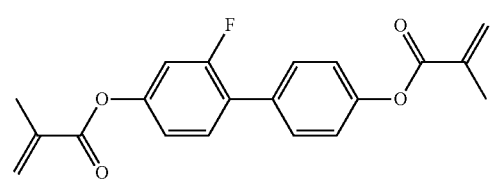

RM-15

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

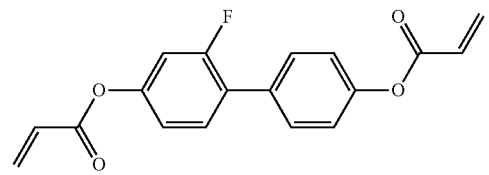 [SMILES: C=CC(=O)Oc1ccc(-c2ccc(OC(=O)C=C)cc2F)cc1]

RM-16

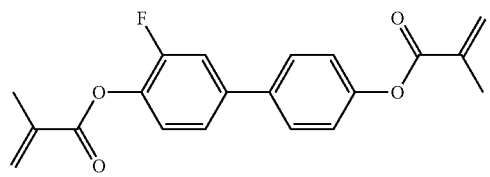 [SMILES: C=C(C)C(=O)Oc1ccc(-c2ccc(OC(=O)C(=C)C)c(F)c2)cc1]

RM-17

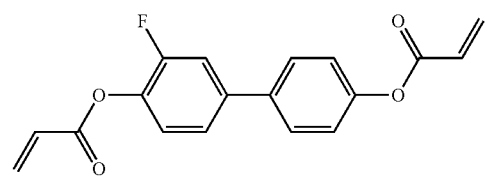

RM-18

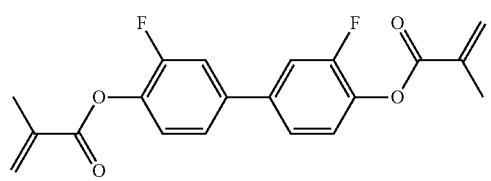

RM-19

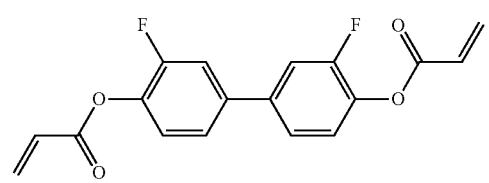

RM-20

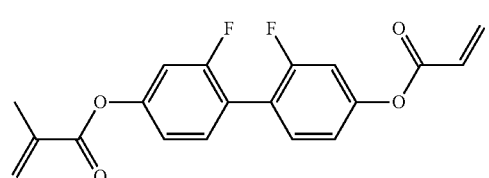

RM-21

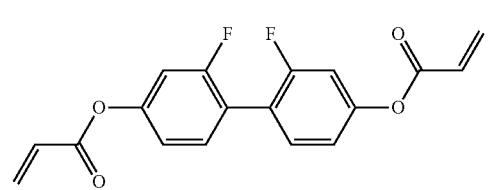 [SMILES: C=CC(=O)Oc1ccc(-c2ccc(OC(=O)C=C)cc2F)c(F)c1]

RM-22

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

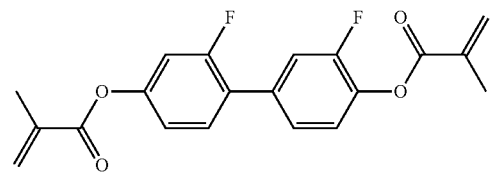

RM-23

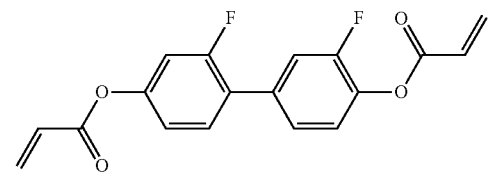

RM-24

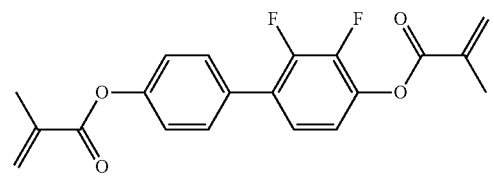 [SMILES: C=C(C)C(=O)Oc1ccc(-c2ccc(OC(=O)C(=C)C)c(F)c2F)cc1]

RM-25

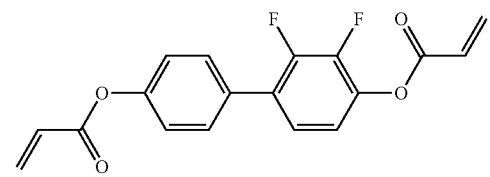

RM-26

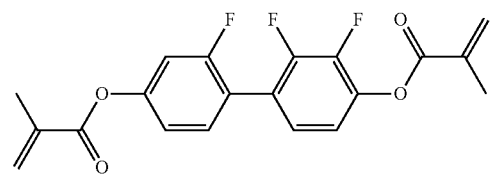

RM-27

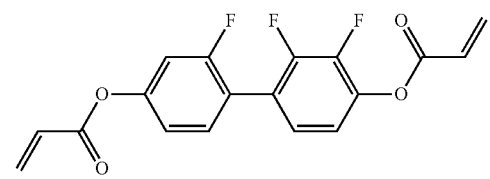 [SMILES: C=CC(=O)Oc1ccc(-c2ccc(OC(=O)C=C)c(F)c2F)c(F)c1]

RM-28

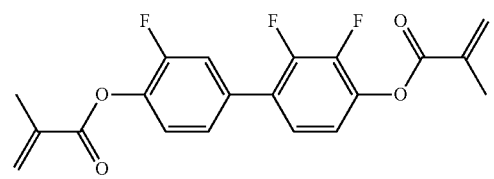 [SMILES: C=C(C)C(=O)Oc1ccc(-c2ccc(OC(=O)C(=C)C)c(F)c2F)cc1F]

RM-29

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

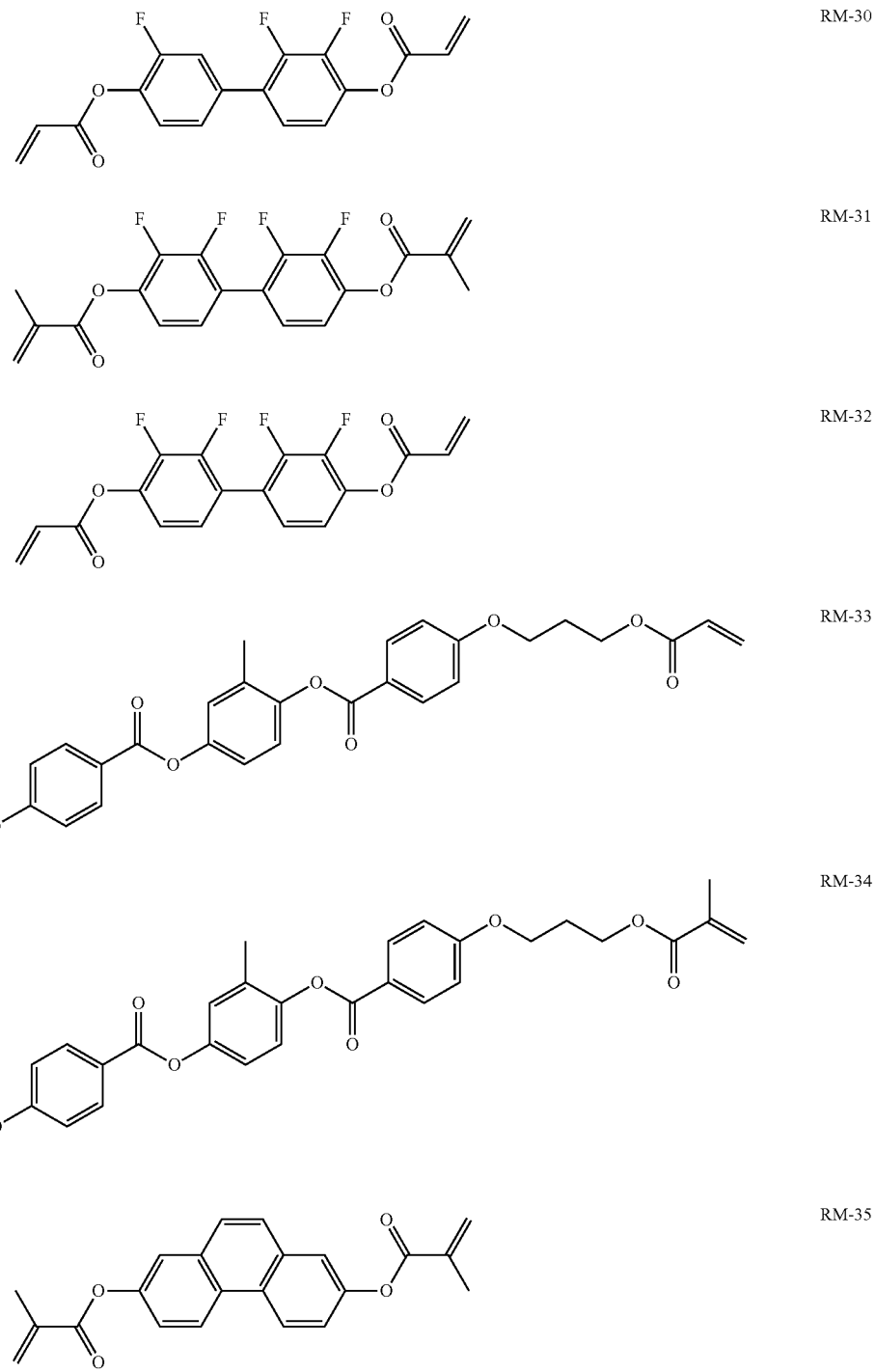

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

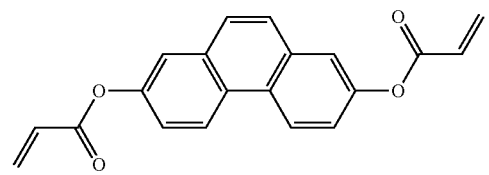 [SMILES: C=CC(=O)Oc1ccc2c(ccc3cc(OC(=O)C=C)ccc32)c1]
RM-36

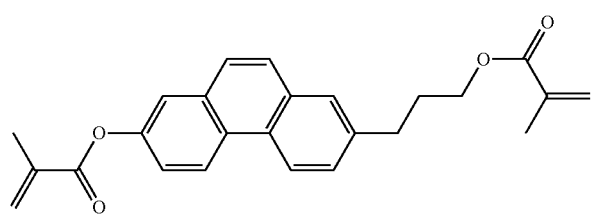 [SMILES: C=C(C)C(=O)OCCCc1ccc2c(ccc3cc(OC(=O)C(=C)C)ccc32)c1]
RM-37

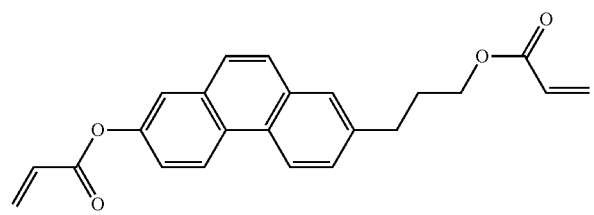 [SMILES: C=CC(=O)OCCCc1ccc2c(ccc3cc(OC(=O)C=C)ccc32)c1]
RM-38

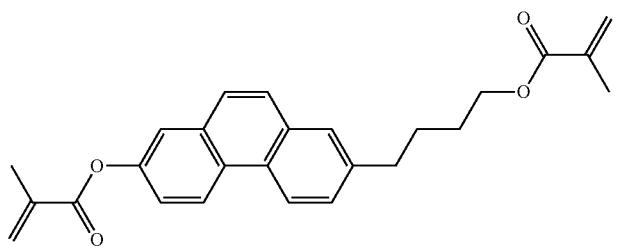 [SMILES: C=C(C)C(=O)OCCCCc1ccc2c(ccc3cc(OC(=O)C(=C)C)ccc32)c1]
RM-39

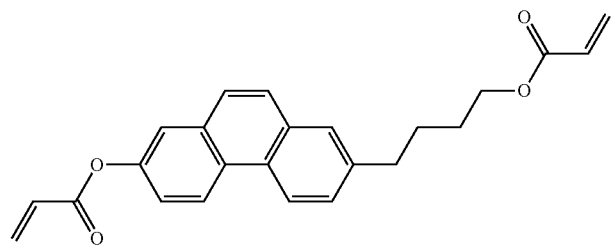
RM-40

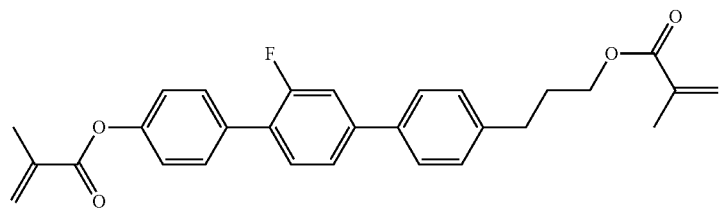 [SMILES: C=C(C)C(=O)OCCCc1ccc(-c2ccc(-c3ccc(OC(=O)C(=C)C)cc3)c(F)c2)cc1]
RM-41

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

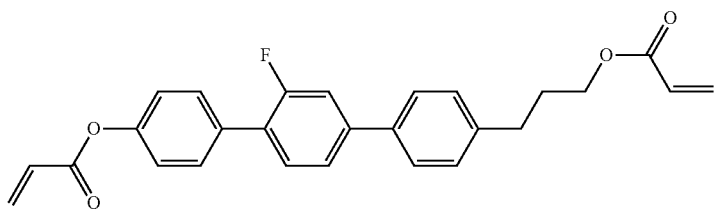 [SMILES: C=CC(=O)OCCCc1ccc(-c2ccc(-c3ccc(OC(=O)C=C)cc3)c(F)c2)cc1]

RM-42

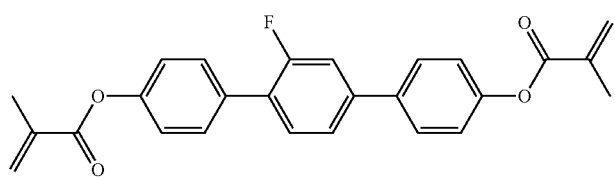 [SMILES: C=C(C)C(=O)Oc1ccc(-c2ccc(-c3ccc(OC(=O)C(=C)C)cc3)c(F)c2)cc1]

RM-43

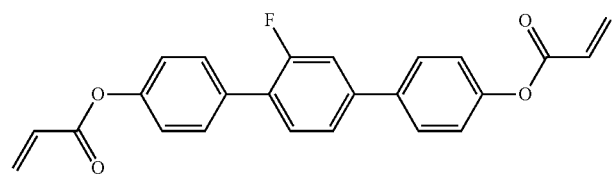 [SMILES: C=CC(=O)Oc1ccc(-c2ccc(-c3ccc(OC(=O)C=C)cc3)c(F)c2)cc1]

RM-44

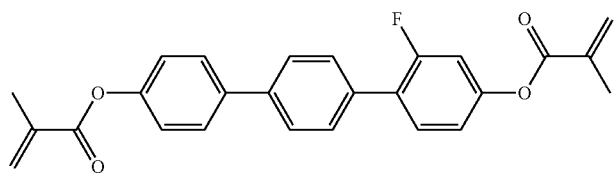 [SMILES: C=C(C)C(=O)Oc1ccc(-c2ccc(-c3ccc(OC(=O)C(=C)C)cc3F)cc2)cc1]

RM-45

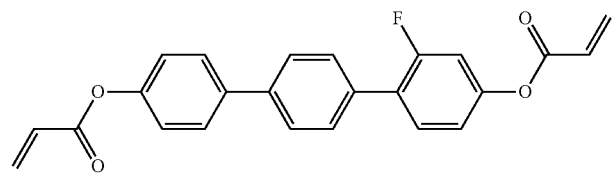 [SMILES: C=CC(=O)Oc1ccc(-c2ccc(-c3ccc(OC(=O)C=C)cc3F)cc2)cc1]

RM-46

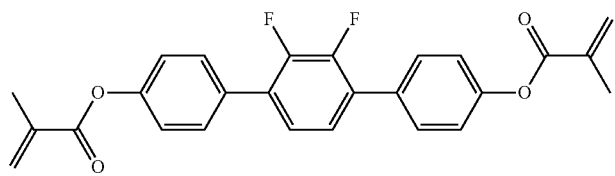 [SMILES: C=C(C)C(=O)Oc1ccc(-c2ccc(-c3ccc(OC(=O)C(=C)C)cc3)c(F)c2F)cc1]

RM-47

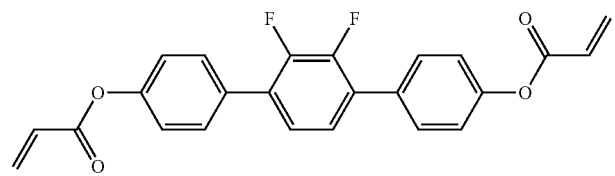

RM-48

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

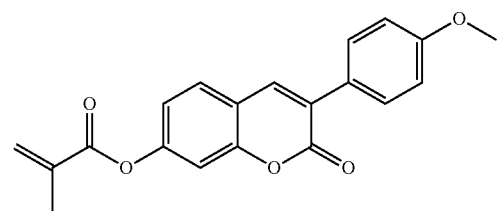 [SMILES: C=C(C)C(=O)Oc1ccc2cc(-c3ccc(OC)cc3)c(=O)oc2c1]

RM-49

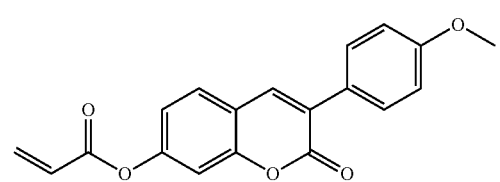 [SMILES: C=CC(=O)Oc1ccc2cc(-c3ccc(OC)cc3)c(=O)oc2c1]

RM-50

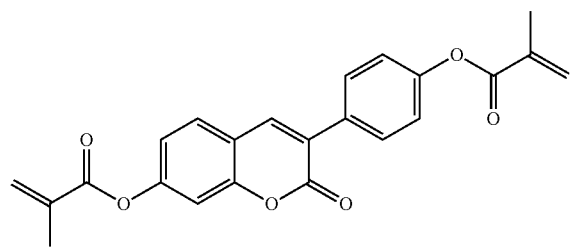 [SMILES: C=C(C)C(=O)Oc1ccc(-c2cc3ccc(OC(=O)C(=C)C)cc3oc2=O)cc1]

RM-51

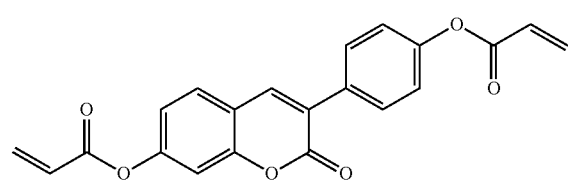 [SMILES: C=CC(=O)Oc1ccc(-c2cc3ccc(OC(=O)C=C)cc3oc2=O)cc1]

RM-52

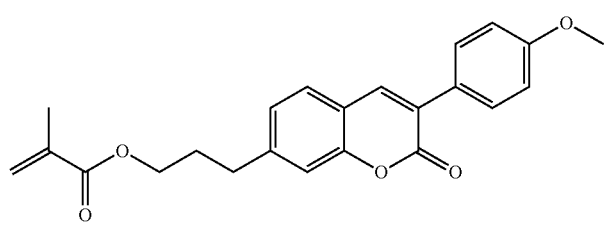 [SMILES: C=C(C)C(=O)OCCCc1ccc2cc(-c3ccc(OC)cc3)c(=O)oc2c1]

RM-53

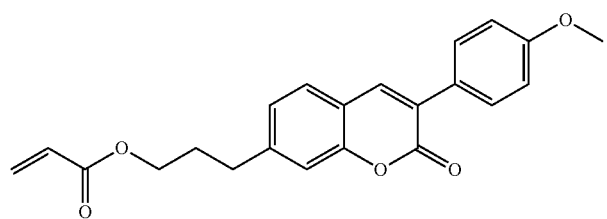 [SMILES: C=CC(=O)OCCCc1ccc2cc(-c3ccc(OC)cc3)c(=O)oc2c1]

RM-54

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

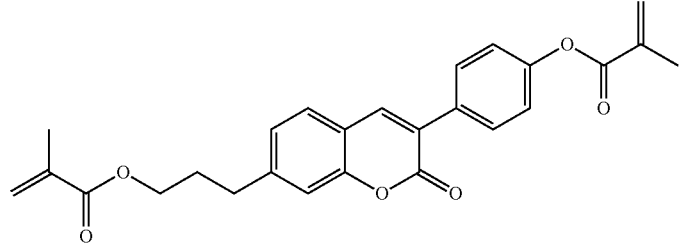 [SMILES: C=C(C)C(=O)OCCCc1ccc2cc(-c3ccc(OC(=O)C(=C)C)cc3)c(=O)oc2c1]

RM-55

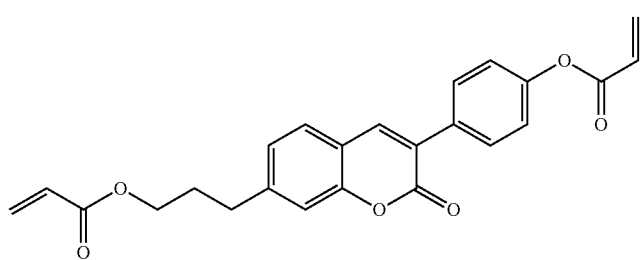 [SMILES: C=CC(=O)OCCCc1ccc2cc(-c3ccc(OC(=O)C=C)cc3)c(=O)oc2c1]

RM-56

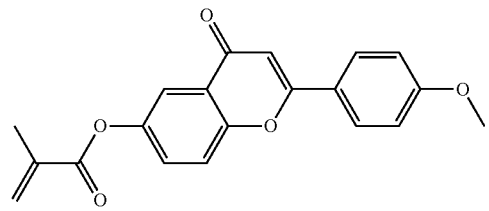 [SMILES: C=C(C)C(=O)Oc1ccc2oc(-c3ccc(OC)cc3)cc(=O)c2c1]

RM-57

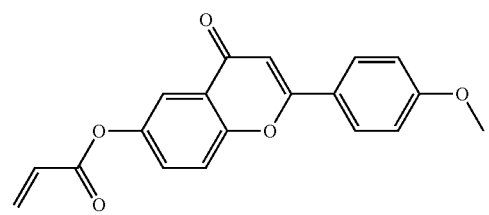 [SMILES: C=CC(=O)Oc1ccc2oc(-c3ccc(OC)cc3)cc(=O)c2c1]

RM-58

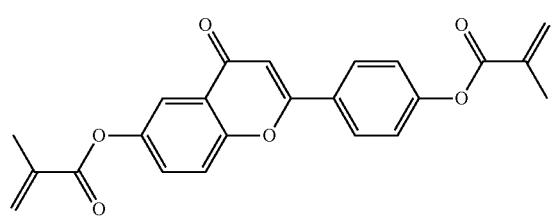 [SMILES: C=C(C)C(=O)Oc1ccc(-c2cc(=O)c3cc(OC(=O)C(=C)C)ccc3o2)cc1]

RM-59

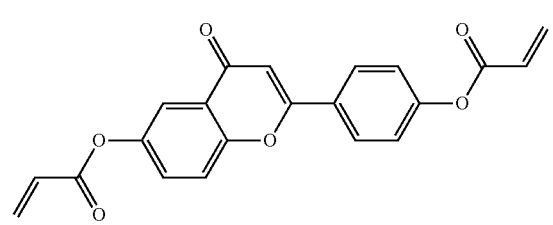 [SMILES: C=CC(=O)Oc1ccc(-c2cc(=O)c3cc(OC(=O)C=C)ccc3o2)cc1]

RM-60

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

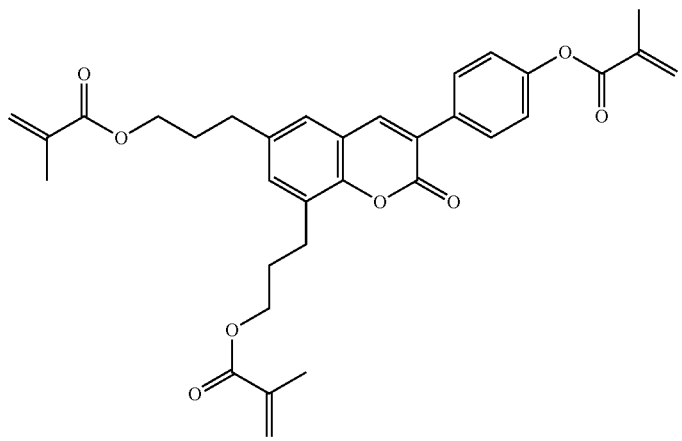 [SMILES: C=C(C)C(=O)OCCCc1cc(CCCOC(=O)C(=C)C)c2oc(=O)c(-c3ccc(OC(=O)C(=C)C)cc3)cc2c1]

RM-61

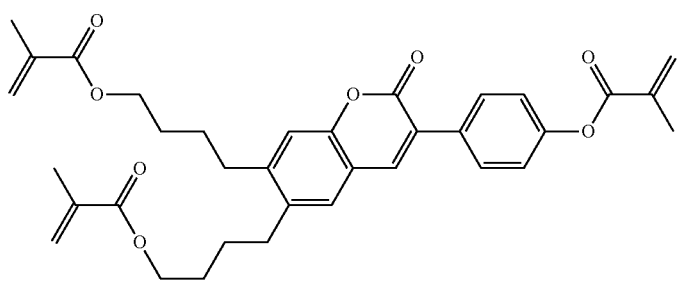 [SMILES: C=C(C)C(=O)OCCCCc1cc2cc(-c3ccc(OC(=O)C(=C)C)cc3)c(=O)oc2cc1CCCCOC(=O)C(=C)C]

RM-62

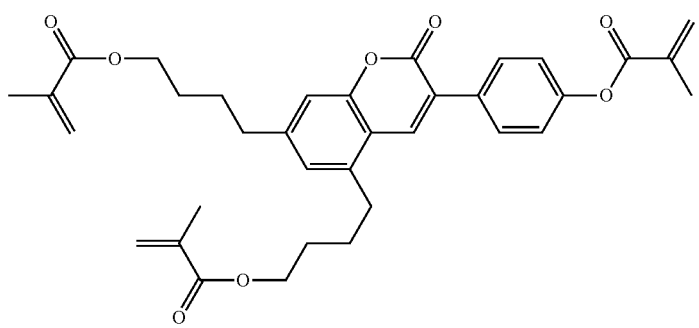 [SMILES: C=C(C)C(=O)OCCCCc1cc(CCCCOC(=O)C(=C)C)c2cc(-c3ccc(OC(=O)C(=C)C)cc3)c(=O)oc2c1]

RM-63

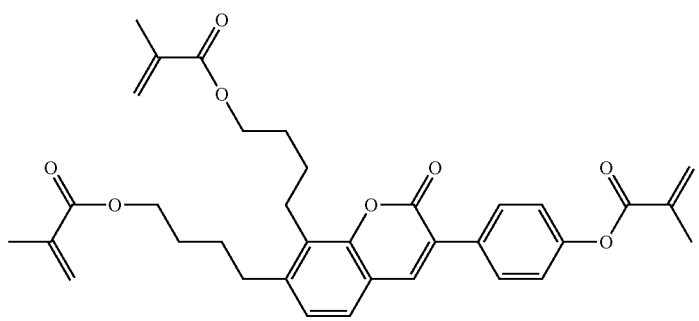 [SMILES: C=C(C)C(=O)OCCCCc1ccc2cc(-c3ccc(OC(=O)C(=C)C)cc3)c(=O)oc2c1CCCCOC(=O)C(=C)C]

RM-64

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

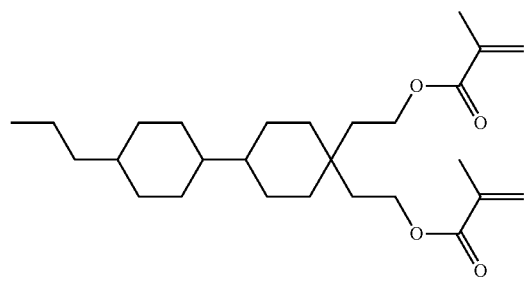 [SMILES: C=C(C)C(=O)OCCC1(CCOC(=O)C(=C)C)CCC(C2CCC(CCC)CC2)CC1]
RM-65

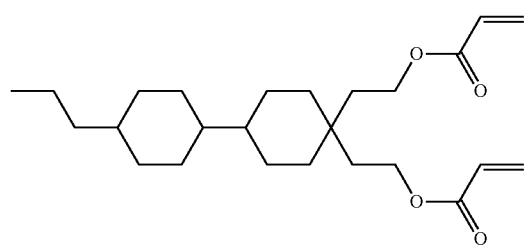 [SMILES: C=CC(=O)OCCC1(CCOC(=O)C=C)CCC(C2CCC(CCC)CC2)CC1]
RM-66

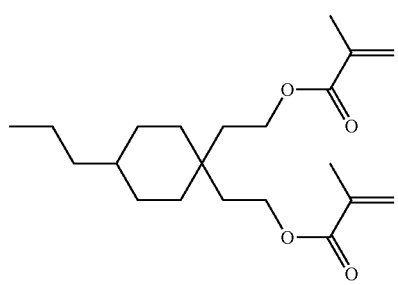 [SMILES: C=C(C)C(=O)OCCC1(CCOC(=O)C(=C)C)CCC(CCC)CC1]
RM-67

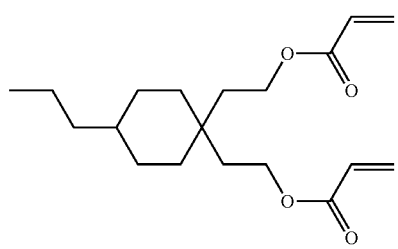 [SMILES: C=CC(=O)OCCC1(CCOC(=O)C=C)CCC(CCC)CC1]
RM-68

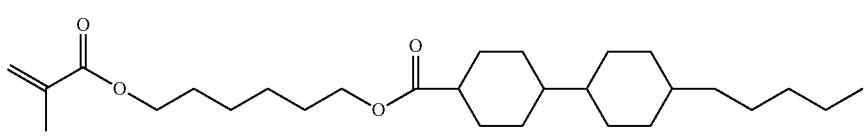
RM-69

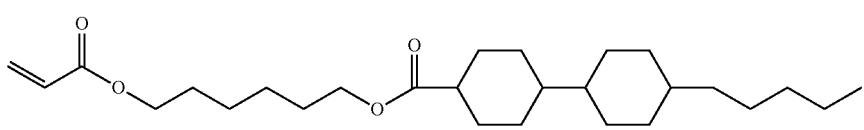 [SMILES: C=CC(=O)OCCCCCCOC(=O)C1CCC(C2CCC(CCCCC)CC2)CC1]
RM-70

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

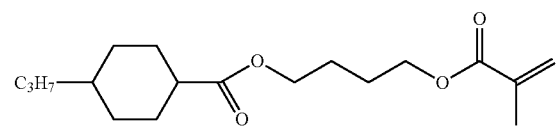

RM-71

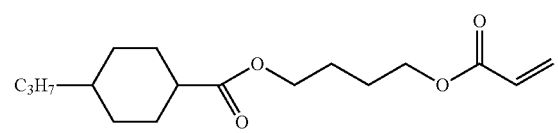

RM-72

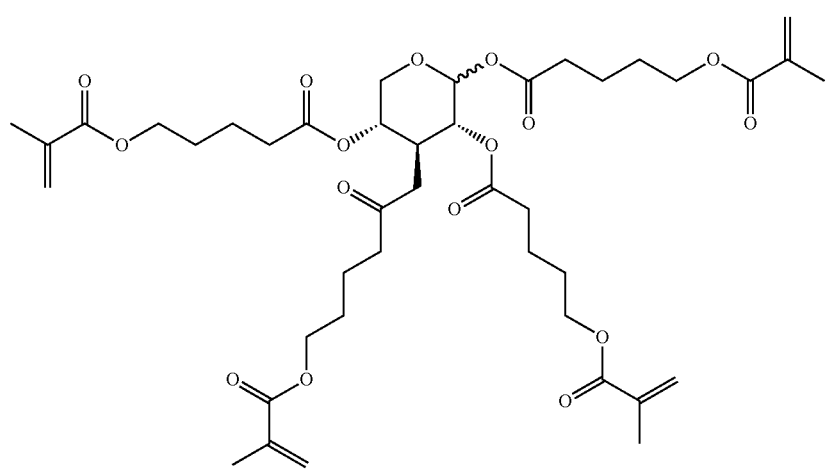 [SMILES: C=C(C)C(=O)OCCCCC(=O)C[C@H]1[C@H](OC(=O)CCCCOC(=O)C(=C)C)COC(OC(=O)CCCCOC(=O)C(=C)C)[C@@H]1OC(=O)CCCCOC(=O)C(=C)C]

RM-73

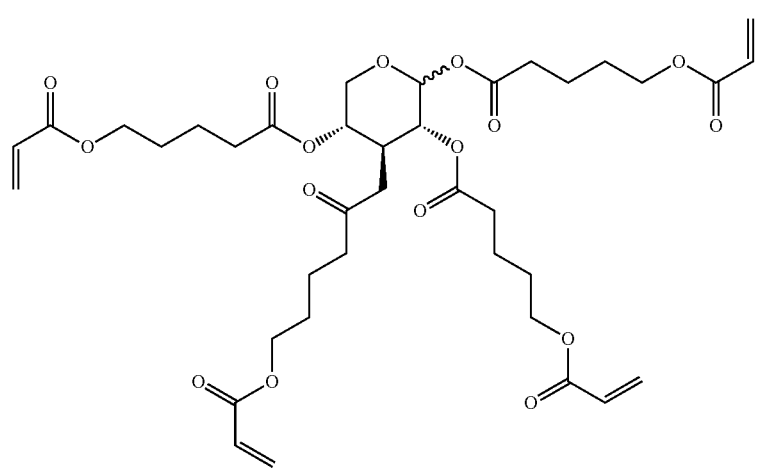 [SMILES: C=CC(=O)OCCCCC(=O)C[C@H]1[C@H](OC(=O)CCCCOC(=O)C=C)COC(OC(=O)CCCCOC(=O)C=C)[C@@H]1OC(=O)CCCCOC(=O)C=C]

RM-74

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

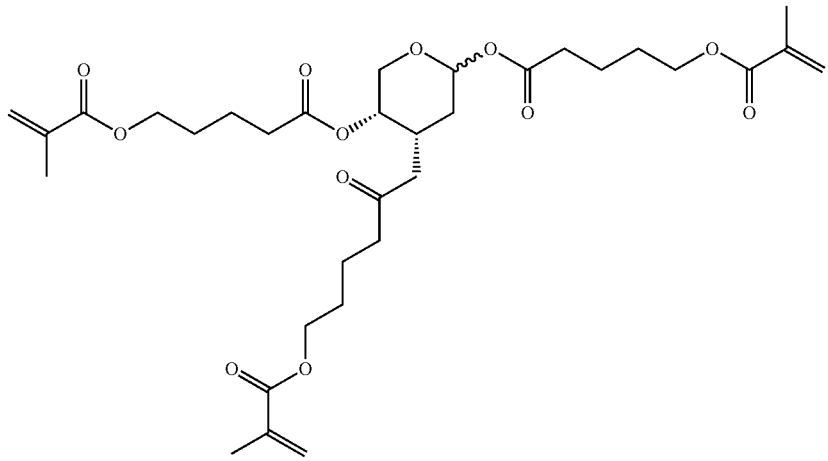 [SMILES: C=C(C)C(=O)OCCCCC(=O)C[C@H]1CC(OC(=O)CCCCOC(=O)C(=C)C)OC[C@H]1OC(=O)CCCCOC(=O)C(=C)C]

RM-75

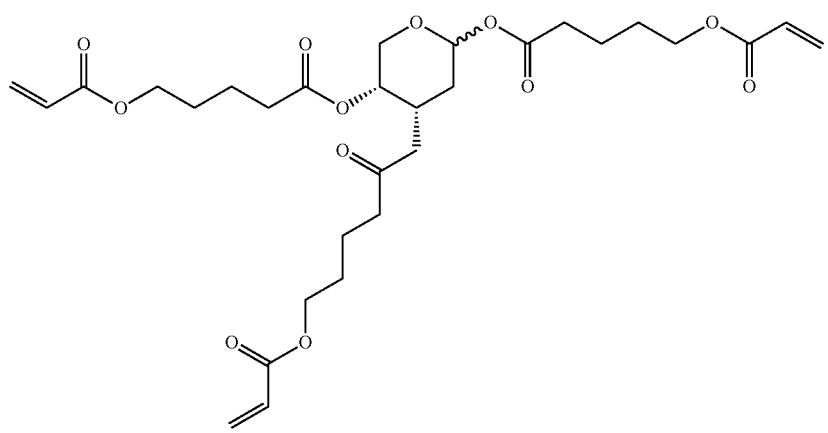 [SMILES: C=CC(=O)OCCCCC(=O)C[C@H]1CC(OC(=O)CCCCOC(=O)C=C)OC[C@H]1OC(=O)CCCCOC(=O)C=C]

RM-76

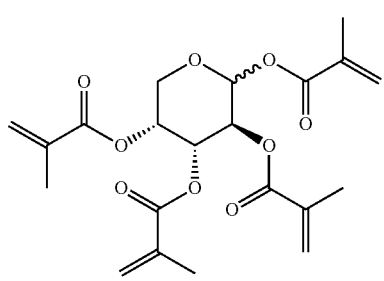 [SMILES: C=C(C)C(=O)OC1OC[C@@H](OC(=O)C(=C)C)[C@@H](OC(=O)C(=C)C)[C@@H]1OC(=O)C(=C)C]

RM-77

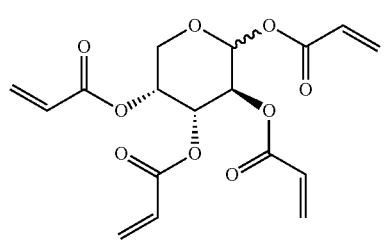 [SMILES: C=CC(=O)OC1OC[C@@H](OC(=O)C=C)[C@@H](OC(=O)C=C)[C@@H]1OC(=O)C=C]

RM-78

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

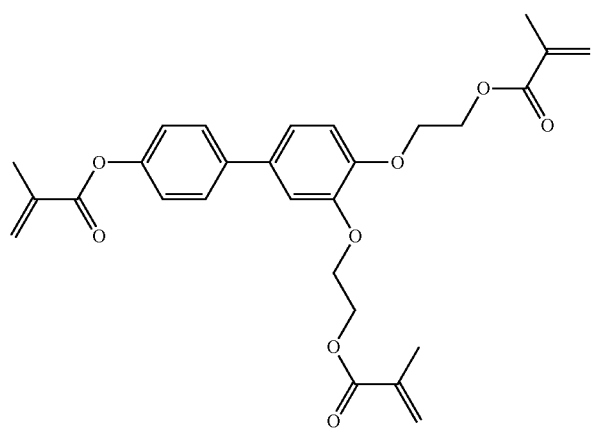

RM-79

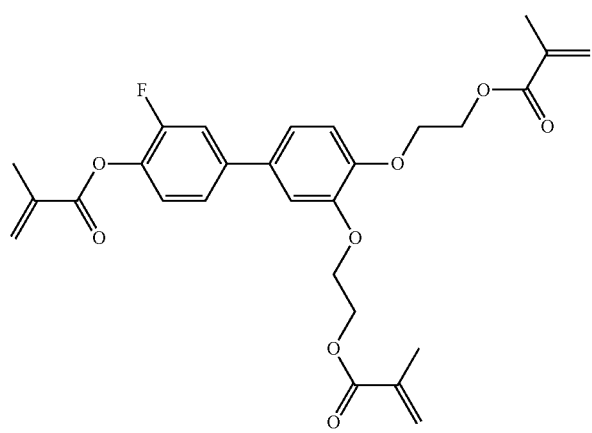 [SMILES: C=C(C)C(=O)OCCOc1ccc(-c2ccc(OC(=O)C(=C)C)c(F)c2)cc1OCCOC(=O)C(=C)C]

RM-80

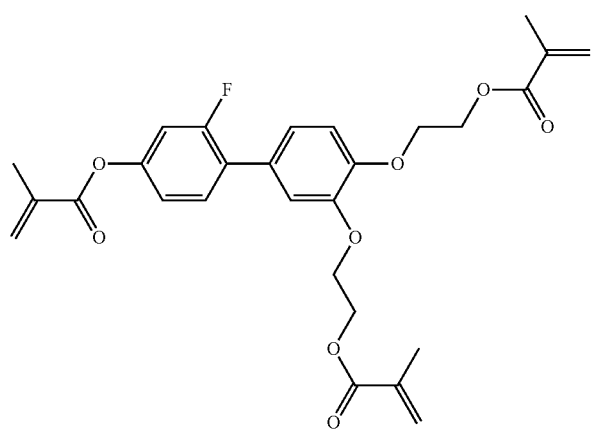

RM-81

TABLE E-continued

Table E shows illustrative compounds which can be used in the LC media in accordance with the present invention, preferably as reactive mesogenic compounds. If the mixtures according to the invention comprise one or more reactive compounds, they are preferably employed in amounts of 0.01-5% by weight. It may be necessary to add an initiator or a mixture of two or more initiators for the polymerization. The initiator or initiator mixture is preferably added in amounts of 0.001-2% by weight, based on the mixture. A suitable initiator is, for example, Irgacure (BASF) or Irganox (BASF).

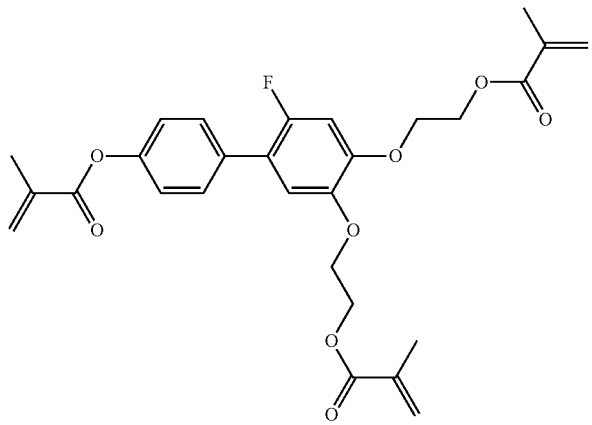 [SMILES: C=C(C)C(=O)OCCOc1cc(F)c(-c2ccc(OC(=O)C(=C)C)cc2)cc1OCCOC(=O)C(=C)C]

RM-82

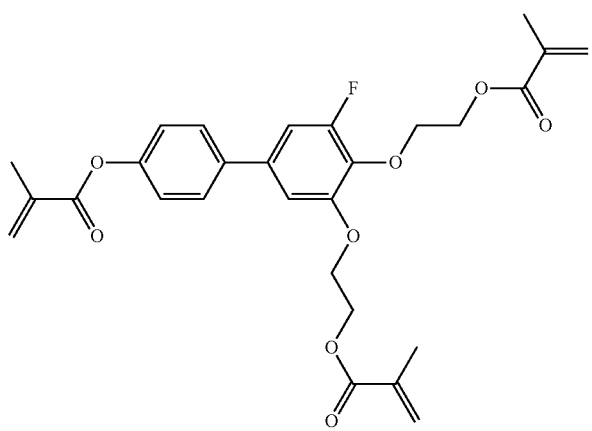 [SMILES: C=C(C)C(=O)OCCOc1cc(-c2ccc(OC(=O)C(=C)C)cc2)cc(F)c1OCCOC(=O)C(=C)C]

RM-83

In a preferred embodiment, the mixtures according to the invention comprise one or more polymerizable compounds, preferably selected from the polymerizable compounds of the formulae RM-1 to RM-83. Media of this type are particularly suitable for PS-VA, PS-FFS and PS-IPS applications. Of the reactive mesogens indicated in Table E, compounds RM-1, RM-2, RM-3, RM-4, RM-5, RM-11, RM-17, RM-35, RM-41, RM-61 and RM-80 are particularly preferred.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. EP 14003014.9, filed Sep. 2, 2014, are incorporated by reference herein.

EXAMPLES

The following working examples are intended to explain the invention without restricting it.

Synthesis Examples

"Conventional work-up" means: water is added if necessary, the mixture is extracted with methylene chloride, diethyl ether, methyl tert-butyl ether (MTBE) or toluene, the phases are separated, the organic phase is dried and evaporated, and the product is purified by distillation under reduced pressure or crystallization and/or chromatography.

Synthesis of 2-ethyldecanedioic acid bis(2,2,6,6-tetramethylpiperidin-4-yl) ester (1)

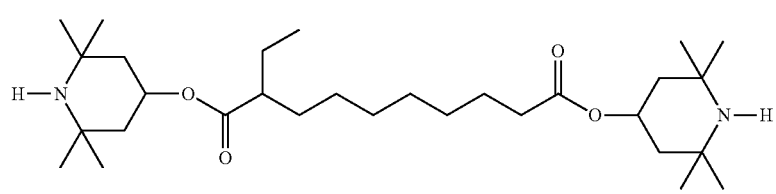

1

1) Synthesis of 2-ethoxycarbonyl-2-ethyldecanedioic acid diethyl ester A

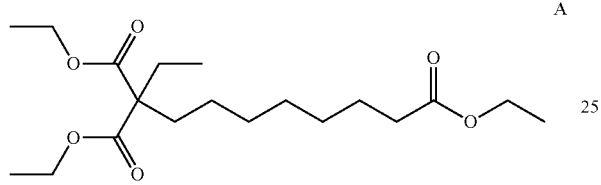

A 194.0 ml (1.035 mol) of diethyl malonate are initially introduced in 775.0 ml of tetrahydrofuran (THF), and 497.7 ml (0.995 mol) of lithium diisopropylamide are added dropwise at room temperature (RT). During this addition, the reaction solution warms to 45° C. It is allowed to cool to 30° C., and 200.0 g (796.3 mmol) of 8-bromooctanoic acid ethyl ester, dissolved in 515.0 ml of THF, are added dropwise. The reaction mixture is then warmed to 60° C. and stirred for 56 h. It is allowed to cool to RT, water is carefully added, and the mixture is subsequently carefully neutralized using dilute hydrochloric acid. The reaction product is extracted with methyl tert-butyl ether (MTB ether), dried over sodium sulfate, filtered and evaporated. The crude product formed is reacted further directly without further purification.

2) Synthesis of 2-carboxy-2-ethyldecanedioic acid B

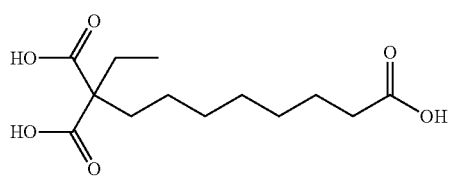

B 358.0 g (676.1 mmol, 67%) of the carboxylic acid ester crude product A are dissolved in 2300 ml of ethanol, and 363.0 ml (3.92 mol, 32%) of sodium hydroxide solution are added. The reaction mixture is stirred under reflux for 16 h. When the reaction is complete, the reaction mixture (a precipitate forms) is treated slowly with water (the precipitate dissolves) and carefully acidified to pH=1 using 10% HCl. The reaction product is extracted with MTB ether. The combined organic phases are evaporated, and the water still present is separated off azeotropically with toluene. The crude product formed is employed in the next synthesis step without further purification.

3) Synthesis of 2-ethyldecanedioic acid C

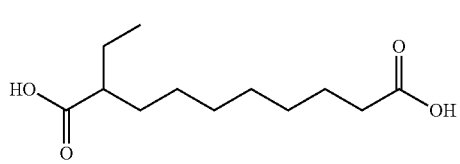

C 242.0 g (68.3%, 602.5 mmol) of the carboxylic acid B are carefully heated to a bath temperature of 250° C. without solvent in a round-bottomed flask with distillation bridge and receiver under an oil-pump vacuum (12 mbar). From 160° C., the oil-pump vacuum drops to about 70 mbar (elimination of $CO_2$), and a readily volatile component distils into the receiver. When the evolution of gas is complete, the vacuum reaches 15 mbar again. The crude product formed is subsequently distilled at 0.4-0.5 mbar and a top temperature of 192-198° C. The distillate obtained is then dissolved in 100 ml of ethanol and 100 ml of sodium hydroxide solution (32%) and stirred at 40° C. for 4 h (residues of monoester are cleaved here). The ethanol is subsequently separated off by means of distillation in vacuo, and the residue is mixed with water and carefully acidified using 400 ml of HCl (10%). The reaction product is extracted with MTB ether, dried over sodium sulfate, filtered and evaporated, giving 105 g of the product in a purity of 97.1%, which is employed in the next synthesis step without further purification.

$^1$H NMR (500 MHz, $CDCl_3$)

δ=0.93 ppm (t, 7.45 Hz, 3H, $CH_3$), 1.30 (s, 8H, $CH_2$), 1.72-1.42 (m, 6H, $CH_2$), 2.28 ($m_c$, 1 H, $CH_{tert}$(O)OH), 2.35 (t, 7.4 Hz, 2H, $CH_2C(O)OH$), 10.73 ($S_{(broad)}$, 2H, C(O)OH).

4) Synthesis of bis(2,2,6,6-tetramethyl-4-piperidinyl-1-oxyl)-2-ethyldecanedioic acid E

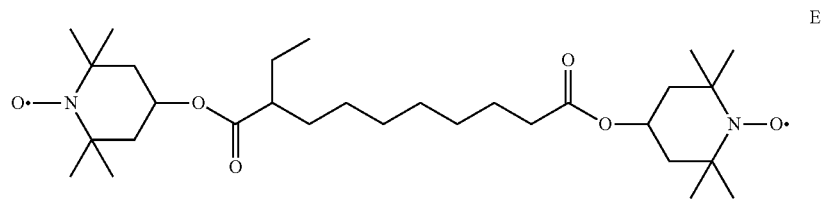

108.9 g (457.8 mmol) of the carboxylic acid C, 236.5 g (1.373 mol) of 4-hydroxy-2,2,6,6-tetramethylpiperidin-1-oxyl (free radical) and 5.59 g of 4-(dimethylamino)pyridine are dissolved in 700 ml of dichloromethane and cooled to 2° C.-5° C. A solution of 297.5 g (1.442 mol) of N,N'-dicyclohexylcarbodiimide in 300 ml of dichloromethane is then added dropwise. The cooling bath is subsequently removed, and the reaction mixture is stirred at room temperature (RT) for 16 h. When the reaction is complete, 86.6 g (686.8 mmol) of oxalic acid dihydrate are carefully added, and the mixture is stirred at RT for one hour. The reaction mixture is filtered through a frit with suction and filtered directly through 4 l of silica gel with dichloromethane (DCM)/MTB ether (9:1). The reaction product obtained is recrystallized twice from well degassed acetonitrile/water (4:1) at +3° C. with stirring, giving 133 g of the product in a purity of 99.8% (HPLC).

MS (EI) 539.5 [M+H$^+$]

5) Synthesis of 2-ethyldecanedioic acid bis(2,2,6,6-tetramethylpiperidin-4-yl) ester 1

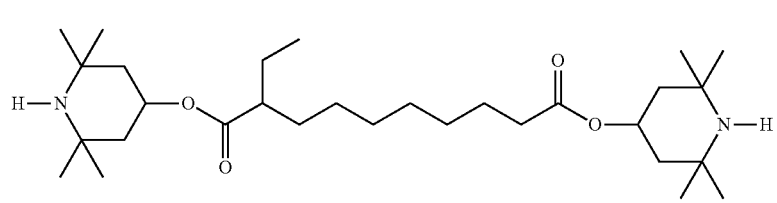

133.0 g (246.4 mmol) of the free radical E are dissolved in 1.33 l of tetrahydrofuran and reduced to the amine using 33.0 g of sponge nickel catalyst (watery, Johnson-Matthey) under a hydrogen pressure of 5 bar at 50° C. for 83.8 h. The crude product obtained is recrystallized from degassed heptane (1:10) at −10° C. The product obtained is subsequently filtered through 1 l of silica gel with MTB ether (removal of residual free radical) and MTB ether/ethanol (1:1). The product obtained is recrystallized from heptane (1:10) at −10° C. and filtered off with suction, giving 83.2 g of the desired product as a white solid in a purity >99.5% (HPLC and GC).

$^1$H NMR (500 MHz, CDCl$_3$)

δ=0.89 ppm (t (superimposed), 7.46 Hz, 5H, CH$_3$, 2×NH), 1.20-1.07 (2×s (superimposed), 16H, CH$_3$, CH$_2$), 1.36-1.2 (2×s (superimposed), 20H, CH$_3$, CH$_2$), 1.54-1.38 (m, 2H), 1.65-1.54 (m$_c$, 4 H), 1.91 (dd, 12.8, 4.08 Hz, 4H), 2.21 (m$_c$, 1 H, CHC(O)O), 2.27 (t, 7.46 Hz, 2H, CH$_2$C(O)O), 5.21 (m$_c$, 2 H, CHOC(O)).

The following compounds can be prepared analogously:

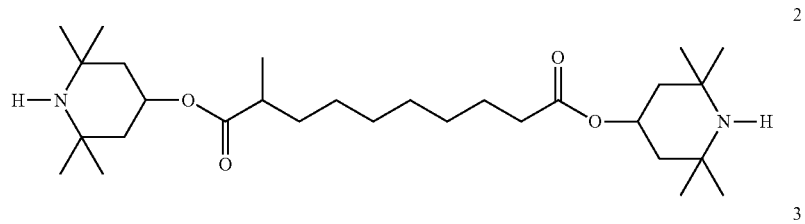
2

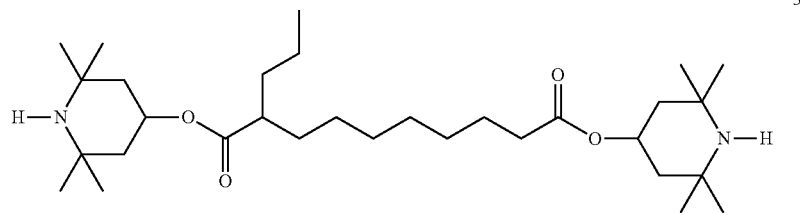
3

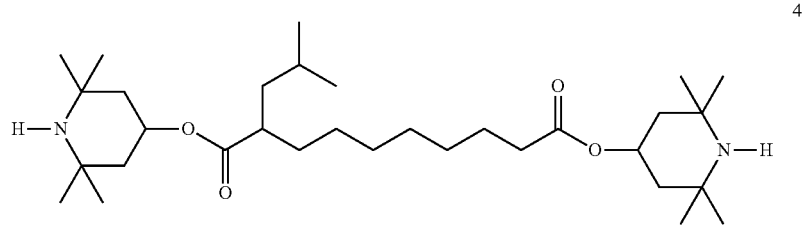
4

Mixture Examples

The following mixtures M1 to M3 are prepared.

Example M1

| | | | |
|---|---|---|---|
| CC-3-V | 32.00% | Clearing point [° C.]: | 85.0 |
| CC-3-V1 | 11.00% | $\Delta n$ [589 nm, 20° C.]: | 0.1089 |
| CC-3-2V1 | 4.50% | $\Delta\varepsilon$ [kHz, 20° C.]: | +15.3 |
| PP-1-2V1 | 2.00% | $\gamma_1$ [mPa · s, 20° C.]: | 89 |
| CCP-3OCF3 | 7.50% | $K_1$ [20° C.]: | 14.4 |
| CCP-5OCF3 | 1.50% | $K_3$ [20° C.]: | 15.1 |
| PUQU-3-F | 1.50% | $V_0$ [V]: | 1.01 |
| APUQU-2-F | 7.00% | | |
| APUQU-3-F | 7.00% | | |
| PGUQU-3-F | 3.00% | | |
| PGUQU-4-F | 8.00% | | |
| PGUQU-5-F | 2.00% | | |
| DPGU-4-F | 5.00% | | |
| DGUQU-4-F | 8.00% | | |

Example M2

| | | | |
|---|---|---|---|
| CC-3-V | 26.50% | Clearing point [° C.]: | 94.5 |
| CC-3-V1 | 10.00% | $\Delta n$ [589 nm, 20° C.]: | 0.1035 |
| CC-3-2V1 | 6.50% | $\Delta\varepsilon$ [kHz, 20° C.]: | +17.2 |
| CCP-V2-1 | 10.00% | $\gamma_1$ [mPa · s, 20° C.]: | 109 |
| APUQU-2-F | 8.00% | $K_1$ [20° C.]: | 15.8 |
| APUQU-3-F | 9.00% | $K_3$ [20° C.]: | 16.6 |
| PGUQU-3-F | 3.00% | $V_0$ [V]: | 1.00 |
| CDUQU-3-F | 8.00% | | |
| DPGU-4-F | 4.00% | | |
| DGUQU-4-F | 8.00% | | |
| DGUQU-2-F | 3.00% | | |
| PGU-4-T | 2.00% | | |

Example M3

| | | | |
|---|---|---|---|
| CY-3-O2 | 12.00% | Clearing point [° C.]: | 86.5 |
| CY-3-O4 | 2.00% | $\Delta n$ [589 nm, 20° C.]: | 0.1092 |
| CY-5-O2 | 12.00% | $\Delta\varepsilon$ [kHz, 20° C.]: | -4.2 |
| CCY-3-O1 | 6.00% | $\gamma_1$ [mPa · s, 20° C.]: | 155 |
| CCY-3-O2 | 8.00% | $K_1$ [20° C.]: | 14.6 |
| CCY-4-O2 | 8.00% | $K_3$ [20° C.]: | 16.6 |
| CPY-2-O2 | 9.00% | $V_0$ [V]: | 2.08 |
| CPY-3-O2 | 9.00% | | |
| PYP-2-3 | 5.00% | | |
| CC-3-V1 | 5.00% | | |
| CC-3-V | 19.00% | | |
| BCH-32 | 5.00% | | |

Voltage Holding Ratio—Light Stability (Sun)

Firstly, the stability of the voltage holding ratio of the respective test mixture itself, of a further sample of this mixture to which the indicated amounts of the compound TINUVIN®770 have been added, and of a further sample of this mixture to which the indicated amounts of compound 1 from Example 1 have been added is determined after 5 min at 100° C., at 1 V and 60 Hz (VHR (initial)). The resultant mixtures are investigated for their light stability (sun) in a test cell having an alignment material for planar alignment and flat ITO electrodes. In order to determine the VHR as a function of the sunlight stability, a lamp which emits the wavelength spectrum of sunlight is used. The test is carried out at 20° C., and the irradiation duration corresponds to 30 min. The voltage holding ratio is determined after 5 minutes at a temperature of 100° C., 1 V and 60 Hz (VHR (sun)). The results are summarized in the following tables. For other measurement conditions, see table.

Mixture M1

| Stabilizer | Conc. (ppm) | VHR (initial) | VHR (sun) |
|---|---|---|---|
| — | — | 96.4 | 72.4 |
| TINUVIN ®770 | 100 | 98.0 | 89.3 |
| TINUVIN ®770 | 500 | 98.0 | 85.7 |
| TINUVIN ®770 | 1000 | 97.8 | 85.9 |
| COMPOUND (1) | 100 | 97.6 | 88.7 |
| COMPOUND (1) | 500 | 97.6 | 82.9 |
| COMPOUND (1) | 1000 | 97.6 | 78.4 |

Mixture M2

| Compound | Conc. (ppm) | VHR (initial) | VHR (sun) |
|---|---|---|---|
| — | — | 95.9 | 72.2 |
| TINUVIN ®770 | 100 | 97.2 | 82.9 |
| TINUVIN ®770 | 500 | 96.8 | 76.4 |
| TINUVIN ®770 | 1000 | 96.9 | 74.7 |
| COMPOUND (1) | 100 | 96.5 | 81.5 |
| COMPOUND (1) | 500 | 96.1 | 75.5 |
| COMPOUND (1) | 1000 | 96.4 | 71.3 |

Mixture M3 (Room Temperature, 10 Hz)

| Stabilizer | Conc. (ppm) | VHR (initial) | VHR (sun) |
|---|---|---|---|
| — | — | 97.1 | 90.2 |
| TINUVIN ®770 | 100 | 99.1 | 96.7 |
| TINUVIN ®770 | 500 | 99.0 | 98.8 |
| TINUVIN ®770 | 1000 | 98.8 | 97.2 |
| COMPOUND (1) | 100 | 98.9 | 96.8 |
| COMPOUND (1) | 500 | 98.7 | 96.9 |
| COMPOUND (1) | 1000 | 98.4 | 96.3 |

Mixture M3

| Stabilizer | Conc. (ppm) | VHR (initial) | VHR (sun) |
|---|---|---|---|
| — | — | 65.8 | 54.5 |
| TINUVIN ®770 | 100 | 70.0 | 69.3 |
| TINUVIN ®770 | 500 | 69.5 | 70.7 |
| TINUVIN ®770 | 1000 | 72.2 | 70.7 |
| COMPOUND (1) | 100 | 69.4 | 70.2 |
| COMPOUND (1) | 500 | 69.5 | 70.2 |
| COMPOUND (1) | 1000 | 69.8 | 67.8 |

VHR—Light Stability (Backlighting)

Firstly, the stability of the voltage holding ratio of the respective test mixture itself, of a further sample of this mixture to which the indicated amounts of the compound TINUVIN®770 have been added, and of a further sample of this mixture to which the indicated amounts of compound 1 from Example 1 have been added is determined after 5 min at 100° C., at 1 V and 60 Hz (0 h). The resultant mixtures are investigated for their light stability (backlighting) in a test cell having an alignment material for planar alignment and flat ITO electrodes. In order to determine the VHR as a function of the light stability in connection with backlighting, sealed test cells having a commercially available backlighting unit are tested. The irradiation duration corresponds to max. 1000 h. After the time intervals indicated, the voltage holding ratio is in each case determined after 5 minutes at a temperature of 100° C., 1 V and 60 Hz. The results are summarized below in the following tables:

| Stabilizer | Conc. (ppm) | 0 h | 48 h | 168 h | 336 h | 504 h | 744 h | 1000 h |
|---|---|---|---|---|---|---|---|---|
| Mixture M1 | | | | | | | | |
| — | — | 95.4 | 81.5 | 69.0 | 65.1 | 62.7 | 61.4 | 59.7 |
| TINUVIN ®770 | 100 | 97.8 | 95.9 | 90.8 | 86.5 | 82.9 | 79.3 | 76.8 |
| TINUVIN ®770 | 500 | 97.5 | 95.7 | 92.6 | 89.9 | 87.4 | 85.0 | 82.5 |
| TINUVIN ®770 | 1000 | 97.3 | 96.0 | 93.9 | 90.9 | 88.5 | 86.5 | 84.8 |
| COMPOUND (1) | 100 | 97.9 | 95.8 | 91.3 | 87.7 | 85.4 | 82.7 | 79.3 |
| COMPOUND (1) | 500 | 97.5 | 96.0 | 93.4 | 91.0 | 88.6 | 84.6 | 82.0 |
| COMPOUND (1) | 1000 | 97.4 | 96.5 | 93.7 | 90.6 | 88.0 | 85.4 | 82.4 |
| Mixture M2 | | | | | | | | |
| — | — | 94.9 | 84.3 | 74.2 | 68.9 | 66.4 | 64.4 | 62.8 |
| TINUVIN ®770 | 100 | 96.7 | 95.6 | 92.1 | 89.7 | 88.0 | 83.9 | 81.7 |
| TINUVIN ®770 | 500 | 96.7 | 95.8 | 93.1 | 90.7 | 89.1 | 87.4 | 85.5 |
| TINUVIN ®770 | 1000 | 96.6 | 96.3 | 94.7 | 92.5 | 91.0 | 89.4 | 87.8 |
| COMPOUND (1) | 100 | 96.1 | 94.6 | 90.7 | 87.4 | 85.1 | 83.5 | 81.6 |
| COMPOUND (1) | 500 | 96.0 | 94.7 | 91.9 | 89.4 | 87.7 | 86.4 | 84.8 |
| COMPOUND (1) | 1000 | 95.5 | 94.7 | 91.6 | 88.9 | 87.1 | 85.5 | 84.2 |

VHR—Heat Stability

Firstly, the stability of the voltage holding ratio of the respective test mixture M1 itself, of a further sample of this mixture to which the indicated amounts of the compound TINUVIN®770 have been added, and of a further sample of this mixture to which the indicated amounts of compound 1 from Example 1 have been added is determined after 5 min at 100° C., at 1 V and 60 Hz (initial). The resultant mixtures are investigated for their heat stability in a test cell having an alignment material for planar alignment and flat ITO electrodes. In order to determine the VHR as a function of the heat stability, sealed test cells are stored in a conventional laboratory heating cabinet at 100° C. for 120 h, and the voltage holding ratio is in each case determined after 5 minutes at a temperature of 100° C., 1 V and 60 Hz (VHR (heat, 120 h)). The results are summarized below in the following table:

Mixture M1

| Stabilizer | Conc. (ppm) | VHR (initial) | VHR (heat, 120 h) |
|---|---|---|---|
| — | — | 96.2 | 92.5 |
| TINUVIN ®770 | 100 | 97.7 | 97.5 |
| TINUVIN ®770 | 500 | 97.9 | 96.0 |
| TINUVIN ®770 | 1000 | 97.6 | 95.0 |
| COMPOUND (1) | 100 | 97.4 | 95.8 |
| COMPOUND (1) | 500 | 97.5 | 95.5 |
| COMPOUND (1) | 1000 | 97.4 | 94.1 |

Low-Temperature Stability 5 ml glass vials are filled with 1 g of the respective test mixture M1 to M3 and stored in a temperature chamber at various temperatures. The samples are investigated daily for the phase stability.

The results are summarized below in the following table:

| Mixture | Temp. | Without Stabilizer | 1000 ppm of Tinuvin 770 | 1000 ppm of compound (1) |
|---|---|---|---|---|
| M1 | −20° C. | 792 h | 168 h | 528 h |
| M2 | −20° C. | — | 96 h | 240 |
| M3 | −20° C. | — | 192 h | 1000 h |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A medium comprising one or more compounds of formula I in a concentration in the range from 1 ppm to 5,000 ppm,

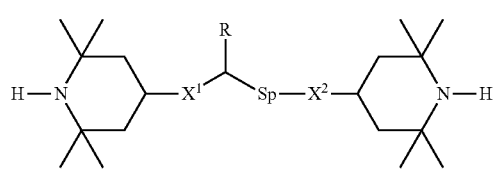

I in which $X^1$ is —O—, —(CO)—O—, —O—(CO)—, —O—(CO)—O—, —NH—, or —NH—(CO)—, $X^2$ is —O—, —(CO)—O—, —O—(CO)—, —O—(CO)—O—, or —NH—(CO)—, Sp denotes straight-chain alkyl having 1 to 20 C atoms, also cycloalkyl, cycloalkylalkyl or alkylcycloalkyl, where one or more —$CH_2$— groups in all these groups may each be replaced by —O— in such a way that no two O atoms in the molecule are connected directly to one another, and R denotes straight-chain or branched alkyl having 1 to 10 C atoms, also cycloalkyl, cycloalkylalkyl or alkylcycloalkyl, where one or more —$CH_2$— groups in all these groups may each be replaced by —O— in such a way that no two O atoms in the molecule are connected directly to one another.

2. The medium according to claim 1, wherein said one or more compounds of formula I are selected from compounds of formulae IA to IE,

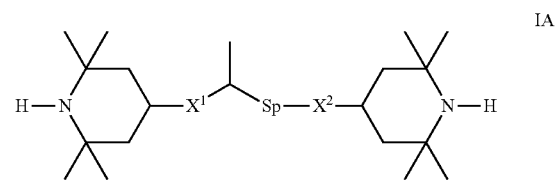

IA

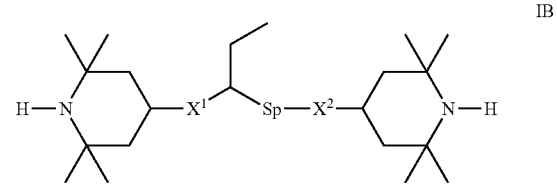

IB

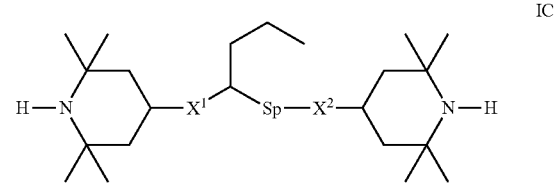

IC

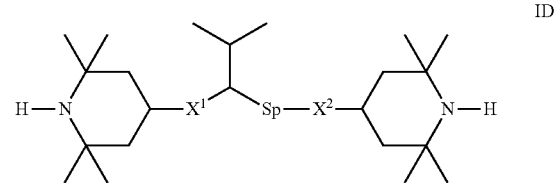

ID

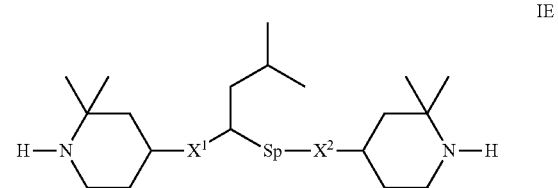

IE in which $X^1$, $X^2$, and Sp have one of the meanings indicated in claim 1.

3. The medium according to claim 1, wherein said one or more compounds of formula I are selected from the compounds of formulae IA-1 to IE-1 and IA-2 to IE-2, IA-1
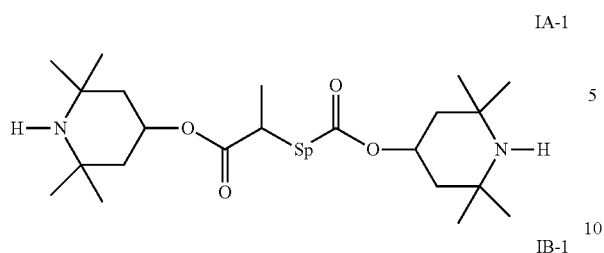

IB-1
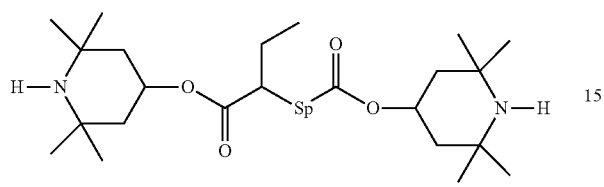

IC-1
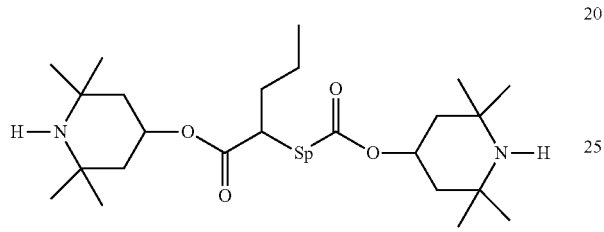

ID-1
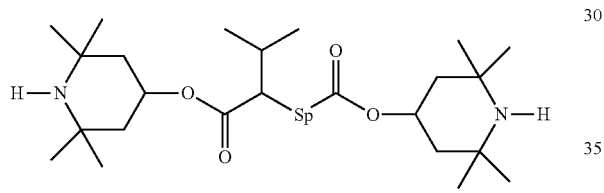

IE-1
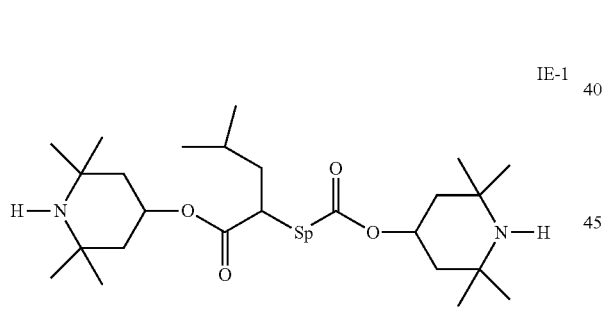

IA-2
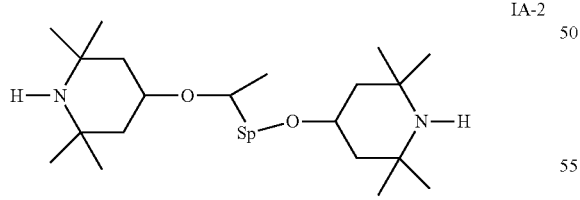

IB-2
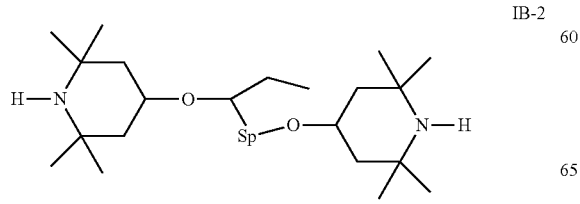

IC-2
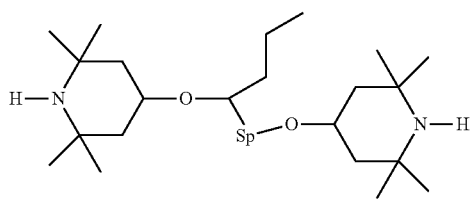

ID-2
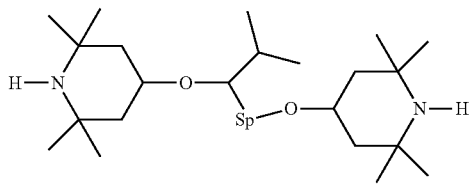

IE-2
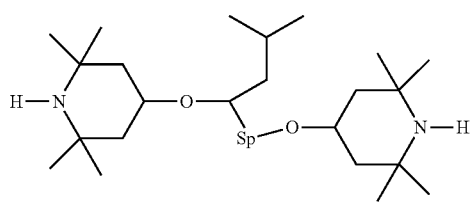

in which Sp has one of the meanings indicated in claim 1.

4. The medium according to claim 1, further comprising one or more compounds of formulae II and/or III,

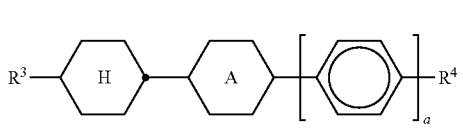 II

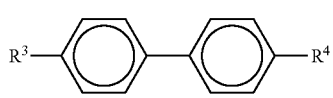 III in which

A denotes 1,4-phenylene or trans-1,4-cyclohexylene, a is 0 or 1, $R^3$ denotes alkenyl having 2 to 9 C atoms, and $R^4$ denotes an alkyl or alkoxy radical having 1 to 15 C atoms, where, in addition, one or more $CH_2$ groups in these radicals may each be replaced, independently of one another, by —C≡C—, —$CF_2$O—, —CH=CH—,

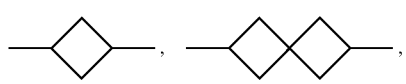

—O—, —CO—O— or —O—CO— in such a way that O atoms are not linked directly to one another, and in which, in addition, one or more H atoms may each be replaced by halogen.

5. The medium according to claim 1, further comprising one or more compounds of formulae D1, D2, D3, D4 and/or D5,

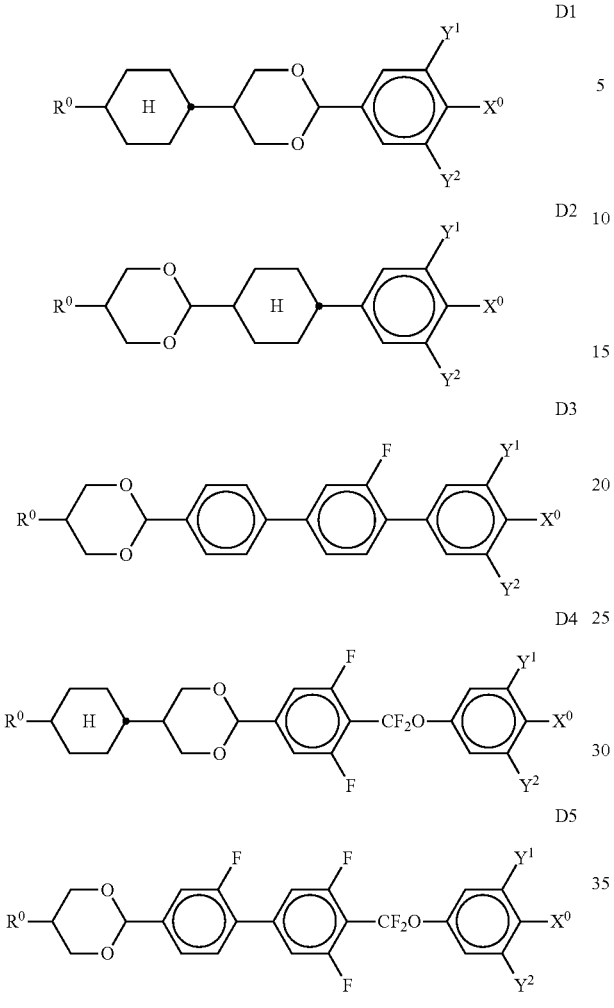

in which
- R⁰ denotes an alkyl or alkoxy radical having 1 to 15 C atoms, where, in addition, one or more CH$_2$ groups in these radicals may each be replaced, independently of one another, by —C≡C—, —CF$_2$O—, —CH=CH—,

—O—, —CO—O— or —O—CO— in such a way that O atoms are not linked directly to one another, and in which, in addition, one or more H atoms may each be replaced by halogen,
- X⁰ denotes F, Cl, a mono- or polyfluorinated alkyl or alkoxy radical having 1 to 6 C atoms, a mono- or polyfluorinated alkenyl or alkenyloxy radical having 2 to 6 C atoms, and
- Y$^{1-2}$ each, independently of one another, denote H or F.

6. The medium according to claim 1, further comprising one or more compounds of formulae Y-1, Y-2, Y-3 and/or Y-4,

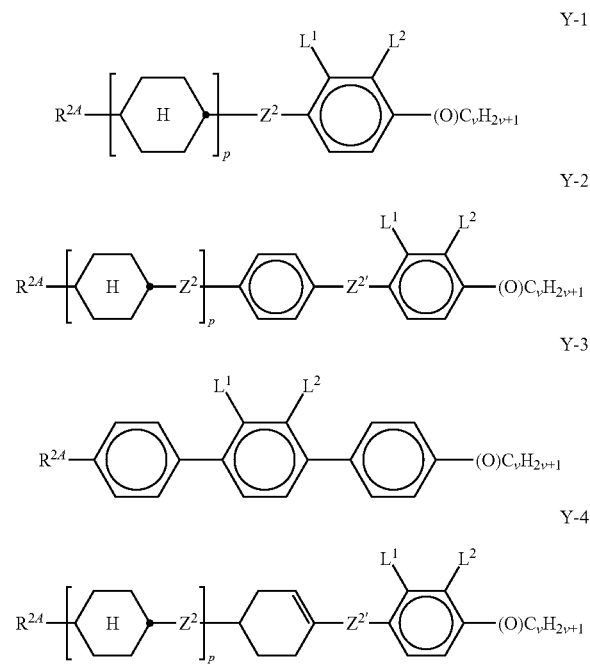

in which
- R$^{2A}$ denotes H, an alkyl or alkoxy radical having 1 to 15 C atoms, where, in addition, one or more CH$_2$ groups in these radicals may each be replaced, independently of one another, by —C≡—, —CF$_2$O—, —CH=CH—,

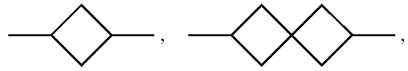

—O—, —CO—O— or —O—CO— in such a way that O atoms are not linked directly to one another, and in which, in addition, one or more H atoms may each be replaced by halogen,
- L$^1$ and L$^2$ each, independently of one another, denote F, Cl, CF$_3$ or CHF$_2$,
- Z$^2$ and Z$^{2'}$ each, independently of one another, denote a single bond, —CH$_2$CH$_2$—, —CH=CH—, —CF$_2$O—, —OCF$_2$—, —CH$_2$O—, —OCH$_2$—, —COO—, —OCO—, —C$_2$F$_4$—, —CF=CF— or —CH=CHCH$_2$O—,
- p denotes 0, 1 or 2,
- q denotes 0 or 1,
- (O)C$_v$H$_{2v+1}$ denotes OC$_v$H$_{2v+1}$ or C$_v$H$_{2v+1}$, and
- v denotes 1 to 6.

7. The medium according to claim 1, wherein said medium further comprises a compound of formula IIa-1

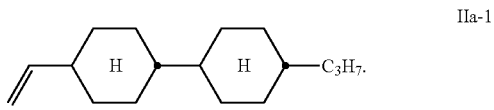

8. The medium according to claim 1, further comprising one or more polymerizable compounds.

9. A process for the preparation of a medium according to claim 1, comprising:
mixing one or more compounds of formula I with at least one further mesogenic compound and optionally with one or more additive(s) and/or one or more polymerizable compounds.

10. A method of generating an electro-optical effect comprising applying a voltage across a medium according to claim 1.

11. An electro-optical liquid-crystal display containing a medium according to claim 1.

12. The medium according to claim 4, wherein $R^4$ denotes alkyl having 1 to 12 C atoms or alkenyl having 2 to 9 C atoms.

13. The medium according to claim 1, wherein $X^1$ and $X^2$ each, independently of one another, denote —O—, —(CO)—O— or —O—(CO)—.

14. The medium according to claim 1, wherein Sp denotes straight-chain alkyl having 1 to 15 C atoms where one or more —$CH_2$— groups may each be replaced by —O— in such a way that no two O atoms in the molecule are connected directly to one another.

15. The medium according to claim 1, wherein Sp denotes straight-chain alkyl having 1 to 10 C atoms where one or more —$CH_2$— groups may each be replaced by —O— in such a way that no two O atoms in the molecule are connected directly to one another.

16. The medium according to claim 1, wherein R denotes straight-chain or branched alkyl having 1 to 7 C atoms.

17. The medium according to claim 1, wherein $X^1$ and $X^2$ each, independently of one another, denote —O—, —(CO)—O— or —O—(CO)—, Sp denotes straight-chain alkyl having 1 to 15 C atoms where one or more —$CH_2$— groups may each be replaced by —O— in such a way that no two O atoms in the molecule are connected directly to one another, and R denotes straight-chain or branched alkyl having 1 to 7 C atoms and.

18. The medium according to claim 1, wherein said one or more compounds of formula I are selected from the following compounds:

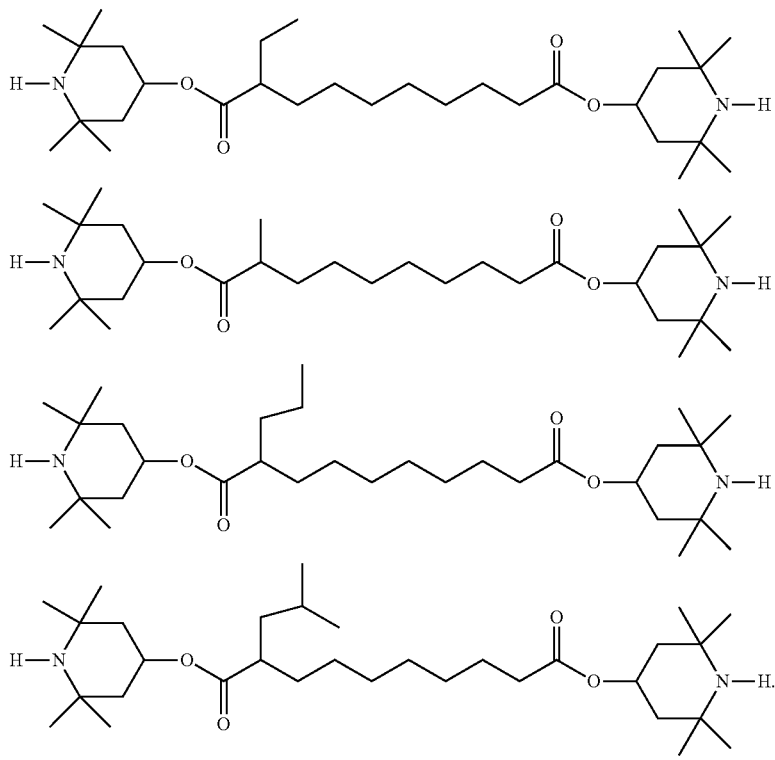

19. The medium according to claim 4, wherein one or more compounds of formula I are of formula I is selected from the following compounds:

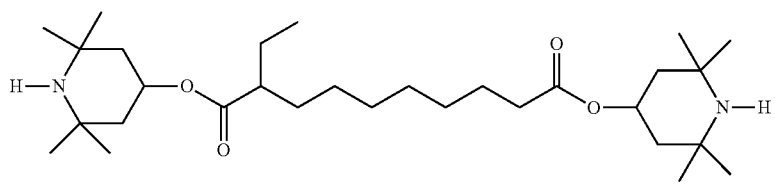

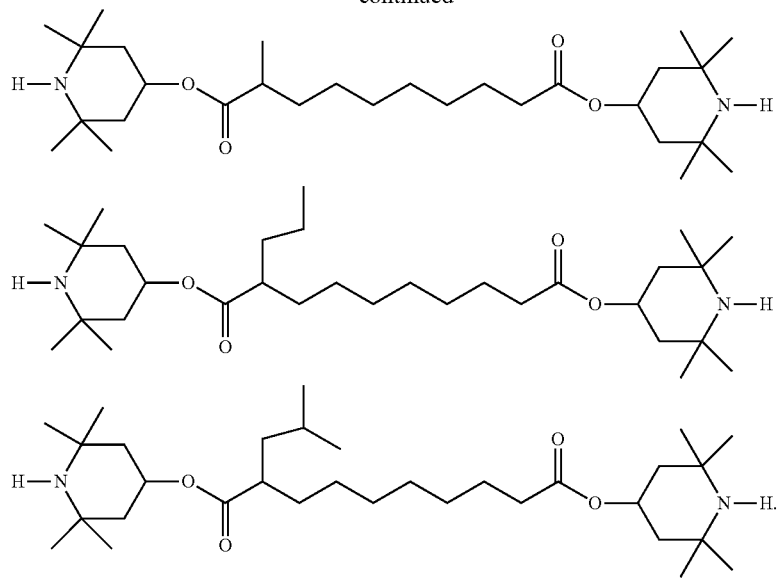

20. The medium according to claim 1, wherein $X^1$ and $X^2$ are each, independently of one another, —(CO)—O— or —O—(CO)—.

21. The medium according to claim 1, wherein $X^1$ and $X^2$ are identical.

22. The medium according to claim 1, wherein Sp denotes straight-chain alkyl having 1 to 20 C atoms.

23. The medium according to claim 1, wherein Sp denotes straight-chain alkyl having 1 to 15 C atoms.

24. The medium according to claim 1, wherein Sp denotes straight-chain alkyl having 1 to 10 C atoms.

25. The medium according to claim 1, wherein R denotes straight-chain or branched alkyl having 1 to 7 C atoms.

26. The medium according to claim 1, wherein R denotes straight-chain or branched alkyl having 1 to 4 C atoms.

27. The medium according to claim 1, wherein said medium is a liquid-crystalline medium having a nematic phase and said one or more compounds of formula I are present in said medium in a concentration in the range from 1 ppm to 2,000 ppm.

28. The medium according to claim 1, wherein said medium is a liquid-crystalline medium having a nematic phase and said one or more compounds of formula I are present in said medium in a concentration in the range from 1 ppm to 1,000 ppm.

29. The medium according to claim 1, wherein said medium is a liquid-crystalline medium having a nematic phase and said one or more compounds of formula I are present in said medium in a concentration in the range from 1 ppm to 500 ppm.

30. The medium according to claim 1, wherein R is ethyl, propyl, butyl, pentyl, hexyl or heptyl.

31. A method of generating an electro-optical effect comprising applying a voltage across a medium comprising one or more compounds of formula I in a concentration in the range from 1 ppm to 5,000 ppm,

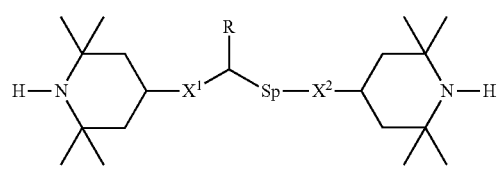

in which
$X^1$ and $X^2$ each, independently of one another, denote —O—, —(CO)—O—, —O—(CO)—, —O—(CO)—O—, —NH—, —NY$^{O1}$— or —NH—(CO)—,
$Y^{O1}$ denotes alkyl having 1 to 12 C atoms,
Sp denotes straight-chain alkyl having 1 to 20 C atoms, also cycloalkyl, cycloalkylalkyl or alkylcycloalkyl, where one or more —CH$_2$— groups in all these groups may each be replaced by —O— in such a way that no two O atoms in the molecule are connected directly to one another, and
R denotes straight-chain or branched alkyl having 1 to 10 C atoms, also cycloalkyl, cycloalkylalkyl or alkylcycloalkyl, where one or more —CH$_2$— groups in all these groups may each be replaced by —O— in such a way that no two O atoms in the molecule are connected directly to one another.

32. An electro-optical liquid-crystal display containing a medium comprising one or more compounds of formula I in a concentration in the range from 1 ppm to 5,000 ppm,

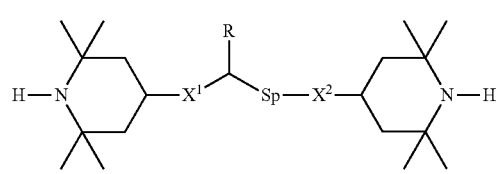

in which

X$^1$ and X$^2$ each, independently of one another, denote —O—, —(CO)—O—, —O—(CO)—, —O—(CO)—O—, —NH—, —NY$^{01}$— or —NH—(CO)—, Y$^{01}$ denotes alkyl having 1 to 12 C atoms, Sp denotes straight-chain alkyl having 1 to 20 C atoms, also cycloalkyl, cycloalkylalkyl or alkylcycloalkyl, where one or more —CH$_2$— groups in all these groups may each be replaced by —O— in such a way that no two O atoms in the molecule are connected directly to one another, and R denotes straight-chain or branched alkyl having 1 to 10 C atoms, also cycloalkyl, cycloalkylalkyl or alkylcycloalkyl, where one or more —CH$_2$— groups in all these groups may each be replaced by —O— in such a way that no two O atoms in the molecule are connected directly to one another.

33. A medium comprising one or more compounds of formulae IA-1 to IE-1 and IA-2 to IE- in a concentration in the range from 1 ppm to 5,000 ppm,

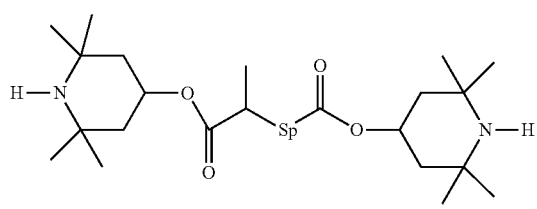

IA-1

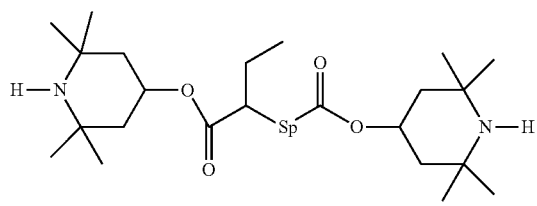

IB-1

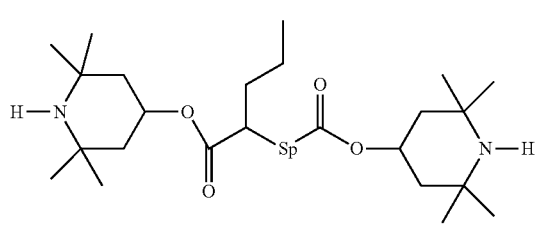

IC-1

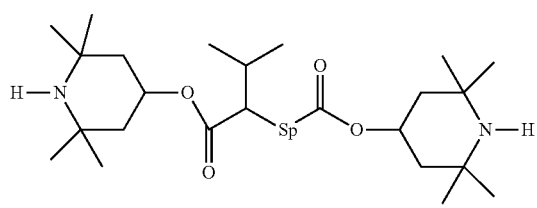

ID-1

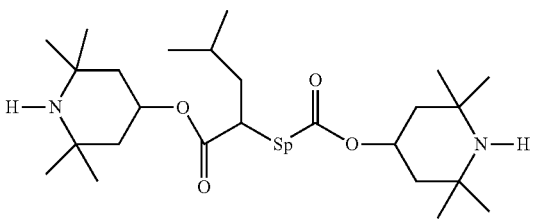

IE-1

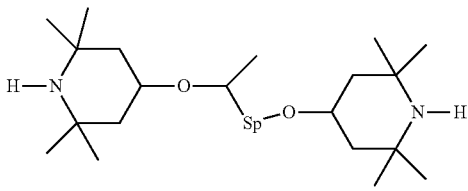

IA-2

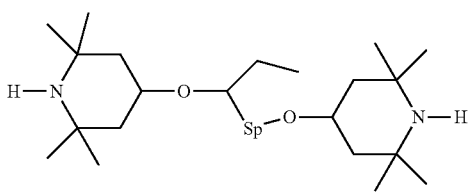

IB-2

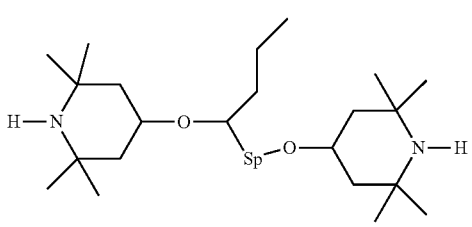

IC-2

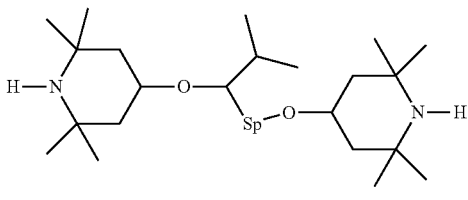

ID-2

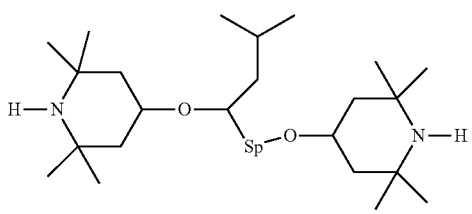

IE-2

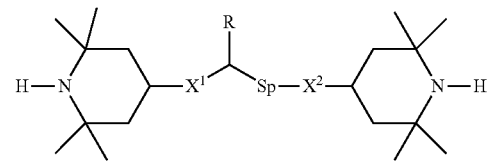

I wherein Sp denotes straight-chain alkyl having 1 to 20 C atoms, also cycloalkyl, cycloalkylalkyl or alkylcycloalkyl, where one or more —CH$_2$— groups in all these groups may each be replaced by —O— in such a way that no two O atoms in the molecule are connected directly to one another.

* * * * *